United States Patent [19]
Gruenert et al.

[11] Patent Number: 6,010,908
[45] Date of Patent: Jan. 4, 2000

[54] GENE THERAPY BY SMALL FRAGMENT HOMOLOGOUS REPLACEMENT

[75] Inventors: Deiter C. Gruenert, Mill Valley, Calif.; Karl Kunzelmann, Wildtal, Germany

[73] Assignee: The Regents of the University of California, Oakland, Calif.

[21] Appl. No.: 08/487,799

[22] Filed: Jun. 7, 1995

Related U.S. Application Data

[63] Continuation-in-part of application No. 08/409,544, Mar. 24, 1995, abandoned, which is a continuation of application No. 07/933,471, Aug. 21, 1992, abandoned.

[51] Int. Cl.$^7$ .............................. C12N 5/10; C12N 15/63
[52] U.S. Cl. ........................ 435/463; 435/325; 435/366; 435/371
[58] Field of Search ................................. 435/172.3, 325, 435/366, 371, 455, 463; 536/23.1; 800/2

[56] References Cited

U.S. PATENT DOCUMENTS 4,950,599  8/1990  Bertling ............................... 435/172.3

OTHER PUBLICATIONS

Marita Gareis, Petra Harrer, Wolf M. Bertling, "Homologous Recombination of Exogenous DNA Fragments with Genomic DNA in Somatic Cells of Mice"Cell. Mol. Biol. (1991) 37:191–203.

Wolf M. Bertling, Marita Gareis, Valentina Paspaleeva, Andreas Zimmer, Jeorge Kreuter, Eberhard Nurnberg, and Petra Harrer, Use of Liposomes, Viral Capsids, and Nanoparticles as DNA Carriers; Biotechnol. Applied Biochem. (1991) 13:390–405

Eric Alton & Duncan Geddes, A mixed message for cystic fibrosis gene therapy, Nature Genetics, vol. 8, pp. 8–9, Sep. 1994.

James J. Logan et al, Cationic lipids for reporter gene and CFTR transfer to rat pulmonary epithelium, Gebe Therapy 2, pp. 38–49, 1995.

Eric J. Sorscher et al, Gene Therapy for Cystic Fibrosis Using Cationic Liposome Mediated Gene Transfer: A Phase I Trial of Safety and Efficacy in the Nasal Airway, Human Gene Therapy, 5:1259–1277, Oct. 1994.

James M. Wilson et al, Gene Therapy of Cystic Fibrosis Lung Disease Using E1 Deleted Adenoviruses: A Phase I Trial, Human Gene Therapy 5:501–519, 1994.

Natasha J. Caplen et al, Liposome–mediated CFTR gene transfer to the nasal epithelium of patients with cystic fibrosis, Nature Medicine, vol. 1, No. 1, Jan. 1995.

Richard M. Boucher et al, Gene Therapy for Cystic Fibrosis Using E1–Deleted Adenovirus: A Phase I Trial in the Nasal Cavity, Human Gene Therapy 5:516–639, 1994.

Mitchell J. Goldman et al, Gene therapy in a xenograft model of cystic fibrosis lung corrects chloride transport more effectively than the sodium defect, Nature Genetics, vol. 9, Feb. 1995.

Joe Palca, The Promise of a Cure, Discover, pp. 79–86, Jun. 1994.

Joseph Zabner et al, Adenovirus–Mediated Gene Transfer Transiently Correct the Chloride Transport Defect in Nasal Epithelia of Patients with Cystic Fibrosis, Cell, vol. 75, pp. 207–216, Oct. 22, 1993.

Terrence R. Flotte et al, An improved system for packaging recombinant adeno–associated virus vectors capable of in vivo transduction, Gene Therapy 2, pp. 29–37, 1995.

Gene therapy for cystic fibrosis, Nature Medicine, vol. 1, No. 3, pp. 182–184, Mar. 3, 1995.

Deborah Erickson, Genes to Order, Scientific American, pp. 112–114, Jun. 1992.

James M. Wilson, Vehicles for gene therapy, Nature, vol. 365, pp. 691–692, Oct. 21, 1993.

Sambrook et al., eds. in "Molecular Cloning: A Laboratory Manual", 2nd ed., 1989. Cold Spring Harbor Laboratory Press,, N.Y. pp. 16.30–16.55, 1989.

Shesely et al., 1991, Proceedings of the National Academy of Science, USA (Abstract Only).

Vega, 1991, Human Genetics, 87:245–253.

Cline, 1985, Pharm. Ther. 29:69–92.

*Primary Examiner*—George C. Elliott
*Assistant Examiner*—Robert Schwartzman
*Attorney, Agent, or Firm*—Hana Verny

[57] ABSTRACT

A method for gene therapy using small fragment homologous replacement. The method introduces small fragments of exogenous DNA into regions of endogenous genomic DNA virtually homologous to the exogenous DNA. The exogenous DNA fragments contains sequence modification that correct mutations in the endogenous DNA or introduce mutations that alter cellular or an infecting pathogen phenotype.

13 Claims, 18 Drawing Sheets

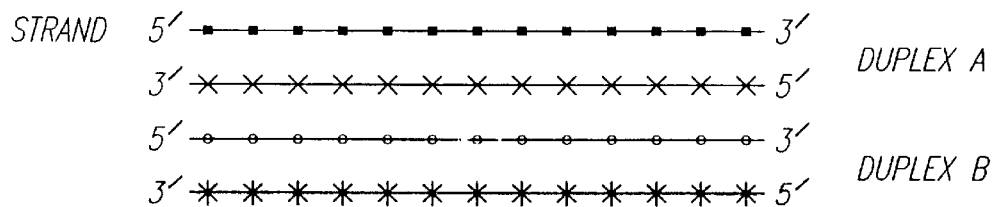
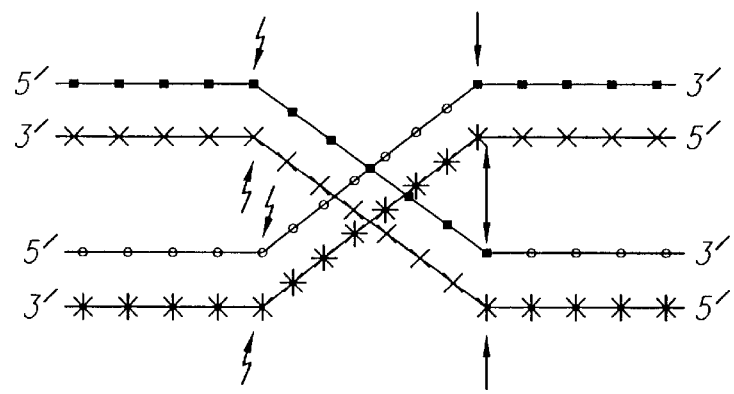
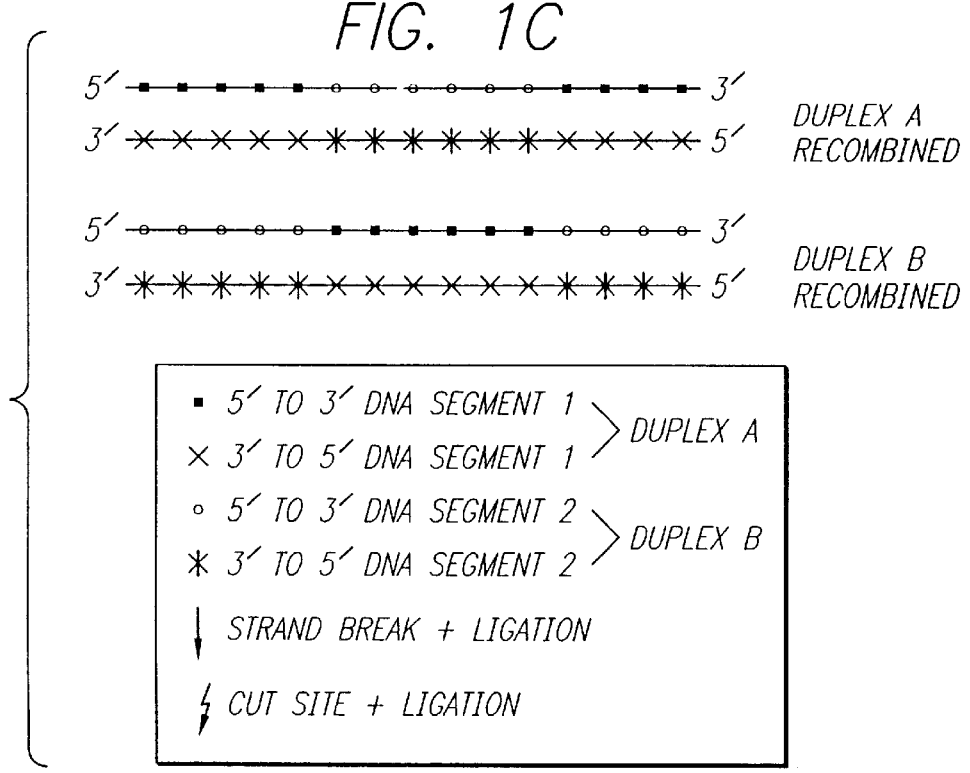

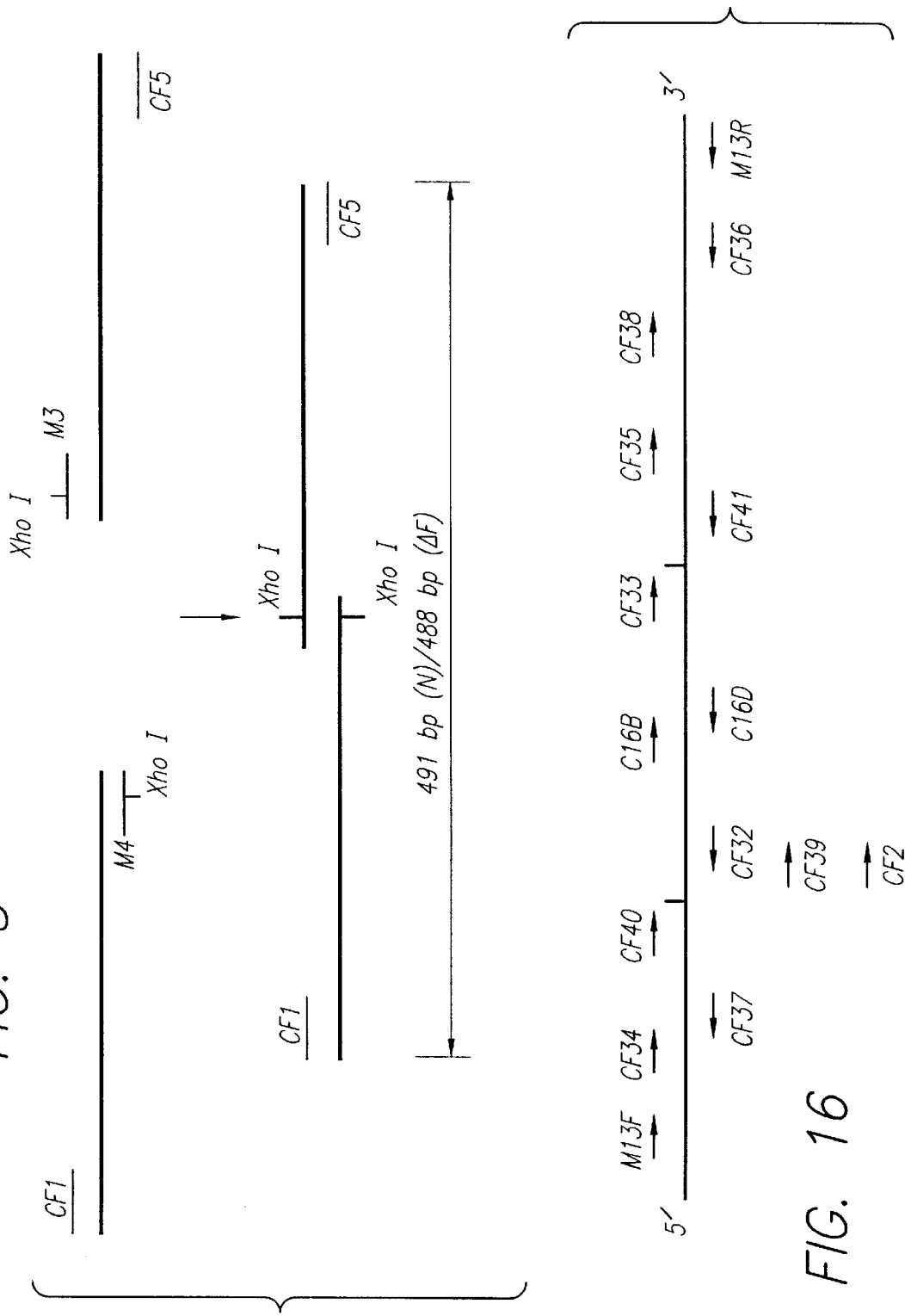

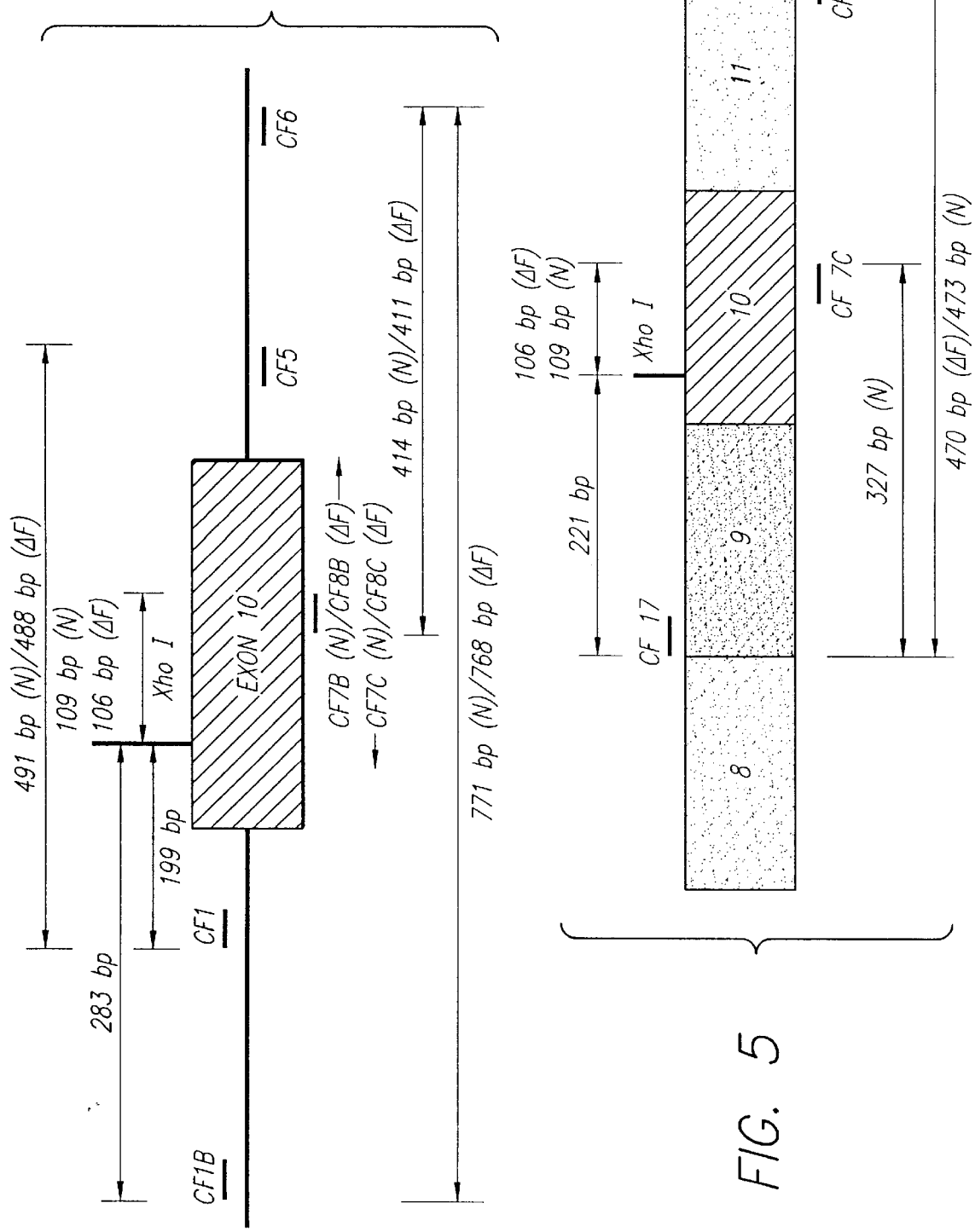

FIG. 20
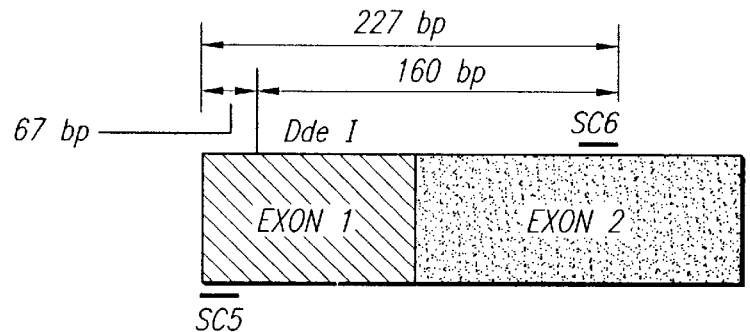
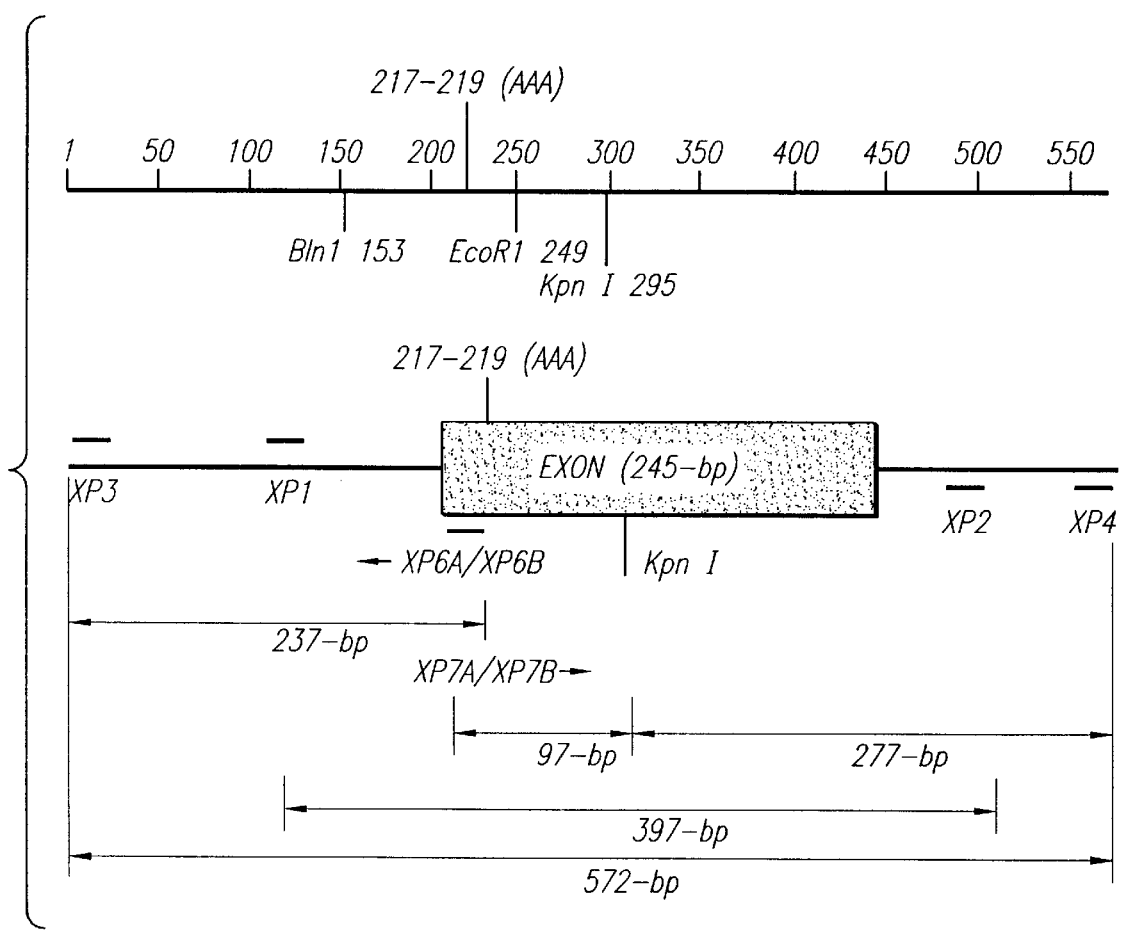
FIG. 21

FIG. 22
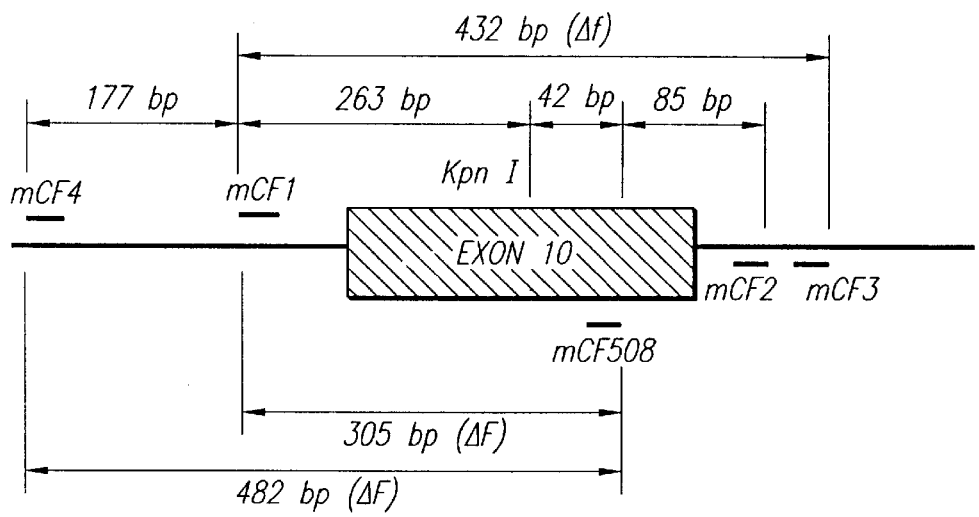
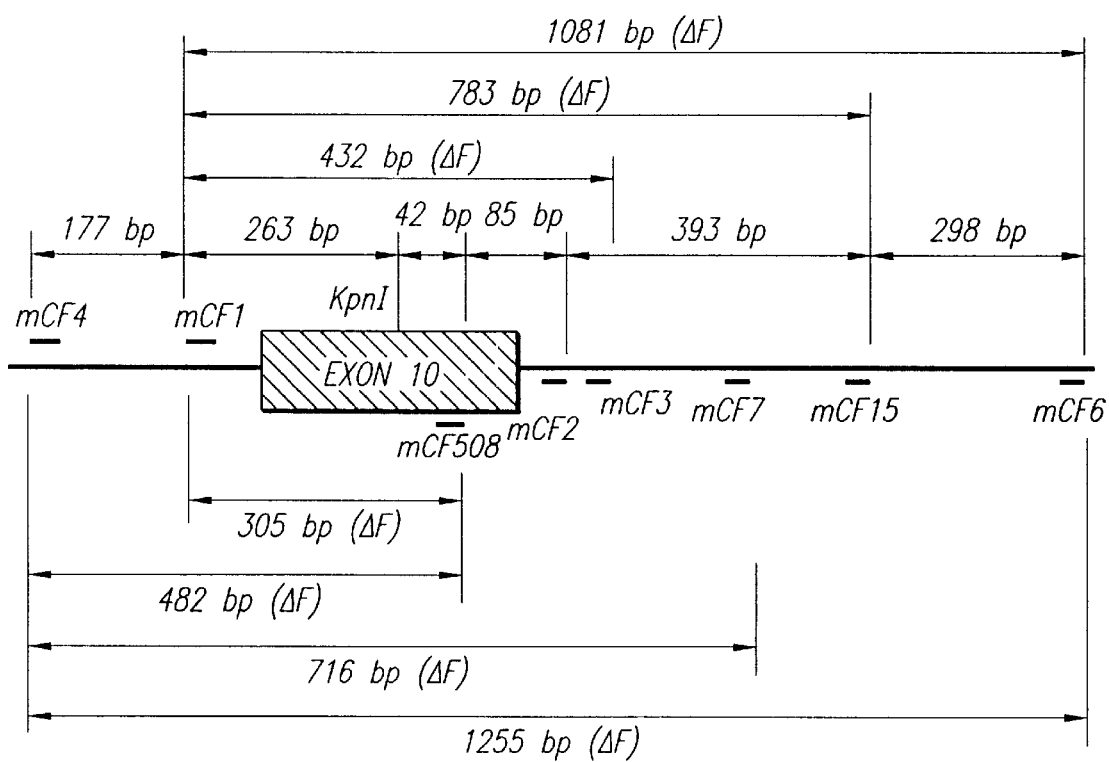
FIG. 23

FIG. 27
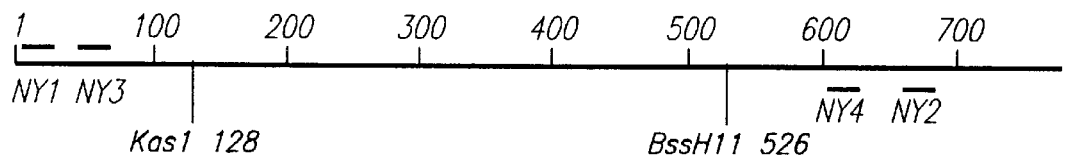
FIG. 28
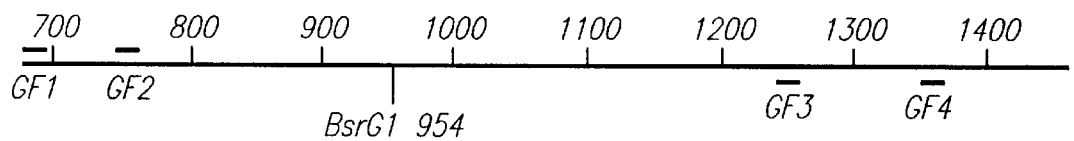
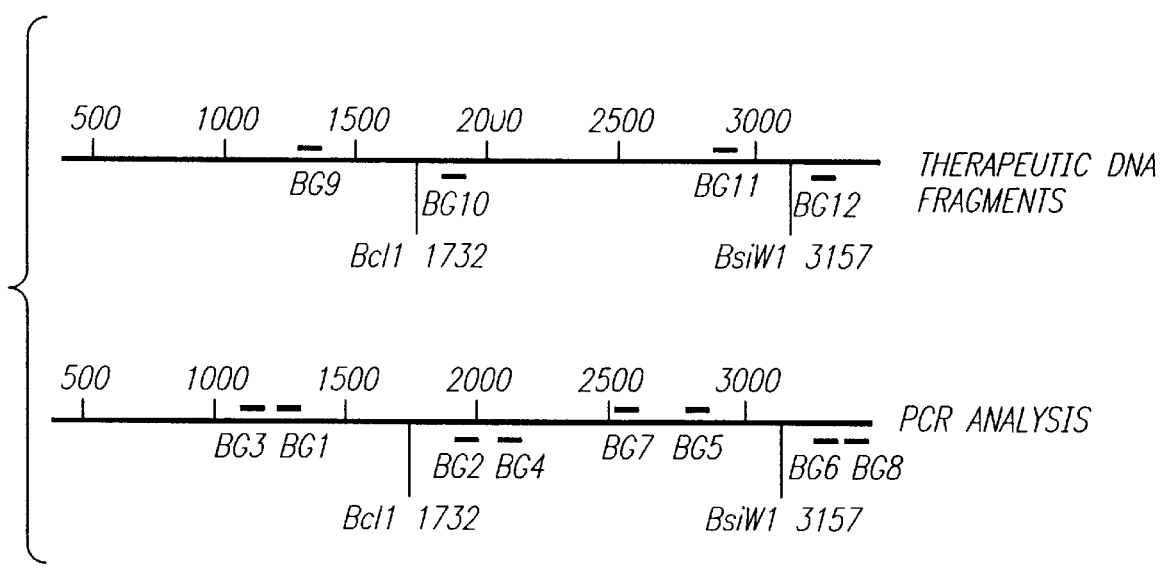
FIG. 29

FIG. 30A

```
GAATTCCAGC CAGACGTGAT GGCGGGTGCC CGTAGTCCCA GCTACTCGGG AGGCTGAGGC    60
AGGAGAATGG CGTGAACCCA GGAGGCAGAA CTTGCAGTGA GCCGAGATCG CGCCACTGCA   120
CTCTAGCCTG GGTGACAGAG TGAGACTCTG TCTCTAAATA AATAAATAAA TAAATAAATA   180
AATAAATAAA ATCAGTGCTT TTTCTTCCTC TGCTACCTCC TTTCCTTCTA CTCAGTTTTA   240
GTCAGTAGTA TTATCTTTTT TCAGATTTAT CTTTGTATTG TTAAATCTGC TTATGCTTCT   300
ATTACTTTAT TTATTAGCTT TAAATGATAC CTTTTGACTT TCAGCTTTTC TTAATAAAGC   360
AATCAGCAAA TTTCCTTTAC ACTCCACACT TATACCCCAT TTCCTTTGTT TGTTTATTTG   420
GTTTTTACTT CTAACTTTTC TTATTGTCAG GACATATAAC ATATTTAAAC TTTGTTTTTC   480
AACTCGAATT CTGCCATTAG TTTTAATTTT TGTTCACAGT TATATAAATC TTTGTTCACT   540
GATAGTCCTT TTGTACTATC ATCTCTTAAA TGACTTTATA CTCCAAGAAA GGCTCATGGG   600
AACAATATTA CCTGAATATG TCTCTATTAC TTAATCTGTA CCTAATAATA TGAAGGTAAT   660
CTACTTTGTA GGATTTCTGT GAAGATTAAA TAAATTAATA TAGTTAAAGC ACATAGAACA   720
GCACTCGACA CAGAGTGAGC ACTTGGCAAC TGTTAGCTGT TACTAACCTT TCCCATTCTT   780
                                        cactgtagct gtactacctt ccat
CCTCCAAACC TATTCCAACT ATCTGAATCA TGTGCCCCTT CTCTGTGAAC CTCTATCATA   840
ctcctc....
ATACTTGTCA CACTGTATTG TAATTGTCTC TTTTACTTTC CCTTGTATCT TTTGTGCATA   900

GCAGAGTACC TGAAACAGGA AGTATTTTAA ATATTTTGAA TCAAATGAGT TAATAGAATC   960

TTTACAAATA AGAATATACA CTTCTGCTTA GGATGATAAT TGGAGGCAAG TGAATCCTGA  1020

GCGTGATTTG ATAATGACCT AATAATGATG GGTTTTATTT CCAGACTTCA CTTCTAATGA  1080

TGATTATGGG AGAACTGGAG CCTTCAGAGG GTAAAATTAA GCACAGTGGA AGAATTTCAT  1140

TCTGTTCTCA GTTTTCCTGG ATTATGCCTG GCACCATTAA AGAAAATATC ATCTTTGGTG  1200

TTTCCTATGA TGAATATAGA TACAGAAGCG TCATCAAAGC ATGCCAACTA GAAGAGGTAA  1260

GAAACTATGT GAAAACTTTT TGATTATGCA TATGAACCCT TCACACTACC CAAATTATAT  1320

ATTTGGCTCC ATATTCAATC GGTTAGTCTA CATATATTTA TGTTTCCTCT ATGGGTAAGC  1380

TACTGTGAAT GGATCAATTA ATAAAACACA TGACCTATGC TTTAAGAAGC TTGCAAACAC  1440

ATGAAATAAA TGCAATTTAT TTTTTAAATA ATGGGTTCAT TTGATCACAA TAAATGCATT  1500

TTATGAAATG GTGAGAATTT TGTTCACTCA TTAGTGAGAC AAACGTCCTC AATGGTTATT  1560

TATATGGCAT GCATATAAGT GATATGTGGT ATCTTTTTAA AAGATACCAC AAAATATGCA  1620

TCTTTAAAAA TATACTCCAA AAATTATTAA GATTATTTTA ATAATTTTAA TAATACTATA  1680
GCCTAATGGA ATGAGCATTG ATCTGCCAGC AGAGAATTAG AGGGGTAAAA TTGTGAAGAT  1740
ATTGTATCCC TGGCTTTGAA CAAATACCAT ATAACTTCTA GTGACTGCAA TTCTTTGATG  1800
CAGAGGCAAA ATGAAGATGA TGTCATTACT CATTTCACAA CAATATTGGA GAATGAGCTA  1860
```

FIG. 30B

```
ATTATCTGAA AATTACATGA AGTATTCCAA GAGAAACCAG TATATGGATC TTGTGCTGTT    1920
CACTATGTAA ATTGTGTGAT GGTGGGTTCA GTAGTTATTG CTGTAAATGT TAGGGCAGGG    1980
CAATATGTTA CTATGAAGTT TATTGACAGT ATACTCCAAA TAGTGTTTGT GATTCAAAAG    2040
CAATATCTTT GATAGTTGGC ATTTGCAATT CCTTTATATA ATCTTTTATG AAAAAAATTG    2100
CAGAGAAAGT AAAATGTAGC TTAAAATACA GTATCCAAAA AAATGGAAAA GGGCAAACCG    2160
TGGATTAGAT AGAAATGGCA ATTCTTATAA AAAGGGTTGC ATGCTTACAT GAATGGCTTT    2220
CCATGTATAT ACTCAGTCAT TCAACAGTTT TTTTTTTAGA GCCCCATCCT TATTTTTTAT    2280
ACACTTTGAG AGCATAATGA AAAGAAAAGC TACCTGCAAA AGTTTTGGAC TTACCTCAAA    2340
GAGGATATAC TACATTCCTC AAAAGGCCTT CTTCCAGGAA TAGTATTTCA TAACCTGGAG    2400
GTTGGAAAAA TCTGGATTAG TTACAAAAAA ATCTGAGTGT TTCTAGCGGA CACAGATATT    2460
TGTCTAGGAG GGGACTAGGT TGTAGCAGTG GTAGTGCCTT ACAAGATAAA TCATGGGCTT    2520
TATTTACTTA CGAGTGGAAA AGTTGCGGAA GGTGCCTTAC AGACTTTTTT TTTGCGTTAA    2580
GTATGTGTTT TCCCATAGGA ATTAATTTAT AAATGGTGGT TTGATTTCCT CAAGTCAACC    2640
TTTAAAAGTA TATTTAGCCA AAATATAGCT TAAATATATT ACTAGTAATA AATTTAGTAC    2700
TGTGGGTCTC TCATTCTCAA AATGAGCATT TACTAATTTC TGAACACTGT GCTAGGTCCT    2760
GGGAATACCA AATTGAATAA GACATAGTCT ATTTTTCTGA AGGGTTTATA GCAGAGTCCC    2820
ATAATGAAAA AAGGAGAAGA GGGAATTC                                       2908
```

GENE THERAPY BY SMALL FRAGMENT HOMOLOGOUS REPLACEMENT

This is a continuation-in-part application of the continuation application Ser. No. 08/409,544 filed on Mar. 24, 1994, abandoned, which is a continuation of the application Ser. No. 07/933,471 filed on Aug. 21, 1992, abandoned.

This invention was developed at least partially with Government support under Grant Nos. DK39619 and HL42368 from the National Institutes of Health and a grant from the Cystic Fibrosis Foundation. The United States Government may have rights in this invention.

BACKGROUND OF THE INVENTION

1. Field of The Invention

The current invention concerns a novel type of gene therapy with small fragment homologous replacement. In particular, the invention concerns a method for introducing small fragments of exogenous DNA into regions of endogenous genomic DNA (cellular or an infecting pathogen) virtually homologous to the exogenous DNA. The exogenous DNA fragments contain sequence modifications that 1) correct mutations in the endogenous DNA or 2) introduce mutations that alter phenotype (cellular or of an infecting pathogen).

2. Background Art and Related Art Disclosures

Gene therapy as a means of treating human genetic disease has been brought into the forefront in recent years by its application for the treatment of a variety of diseases including adenosine deaminase deficiency (ADA) as described in *Transplantation Proc.*, 23:170 (1991) and cystic fibrosis (CF) as described in *Nature Med.*, 1:39 (1995), *Nature Genet.*, 8:42 (1994), and *Cell*, 75:207 (1993).

Other human diseases which are potential targets for gene therapy include but are not limited to thalassaemias, sickle-cell anemia, xeroderma pigmentosum, Fanconi's anemia, ataxia telangiectasia, and muscular dystrophy.

Cystic fibrosis (CF) is one of the diseases in which cDNA based gene therapy has been already proposed and studied. CF is an inherited disease afflicting about 1 in 2500 caucasian live births. The individuals afflicted with CF have a mean life expectancy of about 28 years. CF is characterized primarily by defective regulation of cAMP dependent chloride ion transport, most notably across the apical membranes of epithelial cells. CF results in a debilitating loss of respiratory and pancreatic function; the primary cause of death being an opportunistic *Pseudomonas aeruginosa* infection of the airways. The disease is associated with mutations in the cystic fibrosis transmembrane conductive regulator (CFTR) gene.

Isolation and characterization of the CFTR gene described in *Science*, 245:1059 and 1066 (1989) has been crucial for understanding the biochemical mechanism(s) underlying CF pathology. A mutation in exon 10 resulting in 3-bp, in-frame deletion eliminating a phenylalanine at codon 508 (ΔF508) of CFTR protein, has been found in about 70% of all North American CF chromosomes (*PNAS (USA)*, 87:8447 (1991).

Genetic complementation by gene replacement/conversion has been applied to alter the expression of endogenous mutant genes in cell lines. The CFTR cDNA has been transfected into cystic fibrosis cells to attempt complementation. While the CF phenotype was corrected with wild type CFTR cDNA by complementation, the transfection of the cDNA, however, does not actually correct the defective CFTR gene sequence. Introduction of an expression vector carrying the CFTR cDNA to attain complementation also does not ensure the effective regulation of the CFTR gene.

The use of a full-length wild type CFTR cDNA permits genetic complementation to occur and corrects the defective phenotype corresponding to mutations on CFTR (*Cell*, 68:143–155(1992)). The cAMP-dependent chloride ion transport defect associated with this and other CFTR gene mutations was corrected by introduction of wild type CFTR retrovirus-mediated cDNA into CF epithelial cells as described, for example, in *Cell*, 62:1227 (1990).

Correction of the defective Cl ion transport is the basis for all CF gene therapy strategies. CF gene therapy strategies have used adenovirus vectors for transfer into human nasal (*Cell*, 75:207 (1993) and lung airways (*Nature Genet.*, 8:42 (1991)). A study using liposomes was also carried out in the nasal mucosa of CF patients *Nature Med.*, 1:39 (1995). Each study demonstrated transient wtCFTR expression and correction of defective cAMP-dependent Cl transport.

*Nature Medicine*, 1:182 (1995); *Nature Genet*, 8:8 (1994) and *Nature*, 365:691 (1993) discuss pro and cons of cystic fibrosis gene therapy. More clinically oriented publications appear in *Nature Genet.* 9:126 (1995), *Human Gene Therapy*, 5:509 (1994), *Human Gene Therapy*, 5:1259 (1994); *Gene Therapy*, 2:29 (1995) and *Gene Therapy*, 2:38 (1995). These publications describe clinical trials and results of attempted gene therapy to correct cystic fibrosis using various delivery vehicles.

Numerous approaches have been proposed to facilitate gene therapy such as those described in *Science*, 244:1275 (1989), but at present all gene therapy clinical trials use cDNA-based DNA transfer strategies. Although cDNA-based gene therapy strategies have been shown to be relatively effective in the case of ADA, it is unclear whether a cDNA-based approach will be generally applicable for treatment of a broad spectrum of genetic disorders or whether it is even the optimal mode of gene therapy. Since the cDNA in the eukaryotic expression vector is under the regulation of a heterologous promoter/enhancer, it is expressed in a cell independent fashion and at levels that may not be appropriate for a given cell type.

Studies using recombinant viral vectors for gene therapy do not address concerns about host immune responses to prolonged or repeated exposure to the viral proteins. Liposome medicated gene therapy circumvents this issue, but like the viral approaches, it is cDNA-based, and does not assure cell-appropriate gene expression.

A potential drawback of cDNA approaches is expression and/or overexpression of gene's mRNA and production of protein in all cells with exogenous cDNA. There is evidence to suggest that under certain circumstances overexpression of a therapeutic cDNA can be toxic in vitro and in vivo (*Pediatr. Pulmonol. Suppl.*, 9:30A (1993)). Eukaryotic expression vectors carrying cDNA are independent of cellular regulatory systems controlling RNA and protein levels and the resulting cell-independent expression of a therapeutic cDNA may activate metabolic and physiologic feedback mechanisms that are not compatible with normal function and/or survival. Since these questions remain unanswered, it is unclear whether the cDNA-based gene therapy strategies will ultimately result in a normal in vivo phenotype in treated individuals or be optimal for gene therapy.

It would, therefore, be advantageous to have available a method which could circumvent cell inappropriate expression and possible pathological consequences of such expression.

There have been previous attempts to alter the genome by homologous recombination between DNA sequences residing in the chromosome and newly introduced exogenous DNA sequences. Until now homologous recombination strategies have been primarily based on the transfer of homologous sequence into genomic DNA through replacement and insertion vectors and have relied on positive/negative selection protocols or on intrachromosomal recombination for generation of homologous recombination cells. This approach allowed the transfer of modifications of the cloned gene into the genome of a living cell (*Science*, 244:1288 (1989) and *Int. J. Cell Clon.*, 8:80 (1990).

These existing, classical homologous recombination methods have not been efficient and this has been a major factor limiting the effectiveness of homologous recombination for gene therapy.

In the past, attempts to perform sequence-specific exchange of genomic DNA focussed on binding of oligonucleotides to desired sites in the DNA, and then on site specific cleavage of the genomic DNA. So far, only homopyrimidine or guanine-rich oligonucleotides have been successfully used with this technique.

Up to the present time, homologous recombination has therefore been generally limited in its application. Its primary application has been to the development of transgenic animals by introducing homologous recombination replacement and insertion vectors into mouse embryonic stem cells for gene inactivation and disruption experiments or for the correction of mutant genes in rodent cells (*Cell*, 56:313 (1990); *PNAS*, 86:8927 (1989); *PNAS*, 86:4574 (1989)).

This approach has not been successfully employed for gene correction in metabolically active human cells or in vivo given the disruption produced of intron sequences with selection markers. However, in vitro homologous recombination between two plasmids containing non-complementing, non-reverting deletions in an antibiotic resistance genes has been reported with extract from human cells (*Mol. Cell Biol.*, 5:714 (1985)).

Single strand DNA (ssDNA) oligonucleotide fragments were also utilized to correct a mutation in nonintegrated plasmid DNA co-transfected into human cells (*New Biologist*, 1:223 (1989)). This approach was able to correct a single 14 nucleotide insertion mutation and the mutant phenotype with a 40 base single strand oligonucleotide. However, it does not achieve or demonstrate that this exchange can occur in chromatin DNA, in that these ssDNA fragments were not shown to cause a change in the cell phenotype when genes are integrated into or are a component of genomic DNA.

Single-stranded DNA coated with rec A was shown to anneal to homologous DNA and form a presumed triplex structure known as a "D-loop" in vitro (*Science*, 238:645 (1987)). The homologous pairing of genomic DNA sequences with a homologous rec A coated ssDNA fragment was inferred from the protection afforded the genomic HeLa cell DNA by the restriction enzyme Eco RI (*Science*, 254:1494 (1991)). The D-loop structure, however, was found to be unstable in vitro and may not have a long half-life in metabolically active cells.

Recently, in the U.S. Pat. No. 4,950,599 a method for exchanging homologous DNA sequences in a cell using DNA fragments encapsulated in polyoma capsid, a protein coat of a virus particle was described. While this approach uses DNA fragments, it does not recognize the necessity or importance of intron sequences within the exogenous fragment. The DNA fragments used in an in vitro study into hypoxanthine guanine phosphoribosyl transferase (HPRT) defective hematopoetic cells contained only exon sequences *Mol. Cell Biochem.* 92:107 (1990). The frequency of homologous recombination on this systems was only on the order of $10^{-5}$ and was not enhanced with recA coating or whether the DNA fragment was single or double stranded. In addition, it was unclear to what extent the exogenous DNA fragments were able to induce reversion to HPRT positive phenotype without spontaneous homologous recombination. Furthermore, the use of polyoma virus capsid for delivery of the exogenous DNA fragments will not circumvent issues related to host immune response.

In view of these inefficient attempts to correct mutated genes, it is clear that there is a need for a different in situ method of correcting genetic defects by homologous replacement in mammalian cells, particularly in human cells.

It would therefore be extremely useful to have available a method which would circumvent or eliminate all or some of the above listed disadvantages.

It is therefore a primary object of the current invention to provide a targeted gene replacement, using relatively small genomic DNA fragments with noncoding sequences flanking the sequences to be altered to replace endogenous sequences that are virtually homogenous. As implemented, the invention will circumvent cell inappropriate expression and the physiological and metabolic complications that result.

When applied in vivo, the present method is useful for gene therapy treating human genetic diseases and for countering the deleterious effects of these diseases. In addition, when applied in vitro the method is suitable for ex vivo gene therapy as well as for producing transgenic animals or the treatment of infectious diseases.

SUMMARY OF THE INVENTION

One aspect of the current invention is a method for targeted small fragment homologous replacement (SFHR) of mutated gene sequences in vivo and in vitro.

Another aspect of the current invention is a method for targeted SFHR of mutated gene sequences using small wild type genomic DNA fragments that contain noncoding sequences flanking the sequences to be altered.

Another aspect of the current invention is a method for targeted SFHR of the mutated cystic fibrosis (CF) gene using small wild type CF transmembrane conductance regulator (CFTR) genomic DNA fragments that contain noncoding sequences flanking the sequences to be altered.

Yet another aspect of the current invention is a method for targeted SFHR of mutated dysfunctional sickle cell anemia gene using small wild type β-globin genomic fragments that contain noncoding sequences flanking the sequences to be altered.

Yet another aspect of the current invention is a method for targeted SFHR of mutated dysfunctional thalassaemias gene using small wild type α-and β-globin genomic DNA fragments that contain noncoding sequences flanking the sequences to be altered.

Still another aspect of the current invention is a method for targeted SFHR of mutated dysfunctional xeroderma pigmentosum Group G (XP-G) gene using small wild type (XP-G) genomic DNA fragments that contain noncoding sequences flanking the sequences to be altered.

Another aspect of the current invention is a new genomic DNA sequence of human CFTR gene exon 10 and flanking intron (noncoding) regions.

Another aspect of the current invention is the development of a CF transgenic mouse model with a defined mouse CFTR exon 10 mutation by SFHR using small fragments of genomic mouse CFTR carrying specific exon 10 mutations.

Another aspect of the current invention is a method for targeted SFHR of human immuno-deficiency virus (HIV) provirus using a cocktail of HIV DNA fragments that contain mutations in coding sequences that will inactivate the virus.

Another aspect of the current invention is an assay system for assessment of the frequency of homologous replacement using a selectable or reporter gene systems.

Another aspect of the current invention is a method for gene therapy of a disease associated with a mutated DNA fragment in a subject's target cells, said method comprising steps:

(a) identifying a mutation site within the gene controlling the disease;

(b) obtaining all exogenous type DNA fragment comprising a functional DNA sequence with flanking DNA sequences located upstream and downstream from the functional DNA sequence;

(c) administering to the subject the exogenous (wt) DNA fragment under conditions promoting homologous replacement, said conditions comprising:

i) the exogenous DNA fragment reaching and entering the subject's target cells;

ii) locating the first flanking DNA sequences;

iii) promoting annealing of the corresponding flanking sequences of the exogenous DNA to the mutated sequence; and iv) promoting homologous replacement of the exogenous DNA fragment and the mutated DNA under cellular conditions to produce functional target cells comprising the functional DNA sequence, able to substantially ameliorate the disease's symptoms.

Another aspect of this invention is an immortalized human cell line carrying two alleles of the corresponding defective cellular cystic fibrosis DNA and identified as CFTE29o-, and having an ATCC Accession No. CRL 11151.

Yet another aspect of this invention is a mammalian cell line provided with a genetic defect associated with a predetermined disease, the gene being substituted for the wild type by the method of the invention.

BRIEF DESCRIPTION OF DRAWINGS

FIG. 1 is a scheme illustrating a homologous recombination process naturally occurring in cells.

FIG. 3 is a diagrammatic representation of the generation of fragments 491 and 488 that contain wild type CFTR and mutated CFTR sequences and have a unique XhoI restriction site.

FIG. 4 is a schematic representation of the PCR analysis of genomic DNA amplifying the genomic locus containing the homologous region.

FIG. 5 represents a strategy for RT-PCR analysis of CFTR mRNA.

FIG. 16 is schematic diagram of primer locations for PCR amplification and sequencing reaction of the human CFTR exon 10 and flanking regions.

FIG. 20 is a schematic representation of the RT-PCR and Dde I restriction digestion analysis of 0-globin mKNA-derived cDNA.

FIG. 21 depicts Xeroderma pigmentosum group GXP-G gene restriction map surrounding the exon that contains the mutation defined as one cause of the XP-G phenotype.

FIG. 22 is a schematic representation of the PCR analysis of genomic DNA derived from embryonic stem cells transfected by electroporation with a 432 bp fragment.

FIG. 23 is a schematic representation of the PCR analysis of genomic DNA derived from embryonic stem cells transfected by electroporation with 783 bp or 1081 bp fragments.

FIG. 27 illustrates the cDNA sequence of the neomycin resistance gene (Neo) insert of the pcDNA3 plasmid with unique restriction enzyme site to be used to introduce mutations.

FIG. 28 illustrates the cDNA sequence of the green fluorescent protein (GFP) insert of the plasmid pGFP-N1 with unique restriction enzyme site to be used to introduce mutations.

FIG. 29 illustrates the wild type LacZ cDNA insert of plasmid pZeoLacZ encoding for the β-galactosidase (β-gal)

Figure 2:
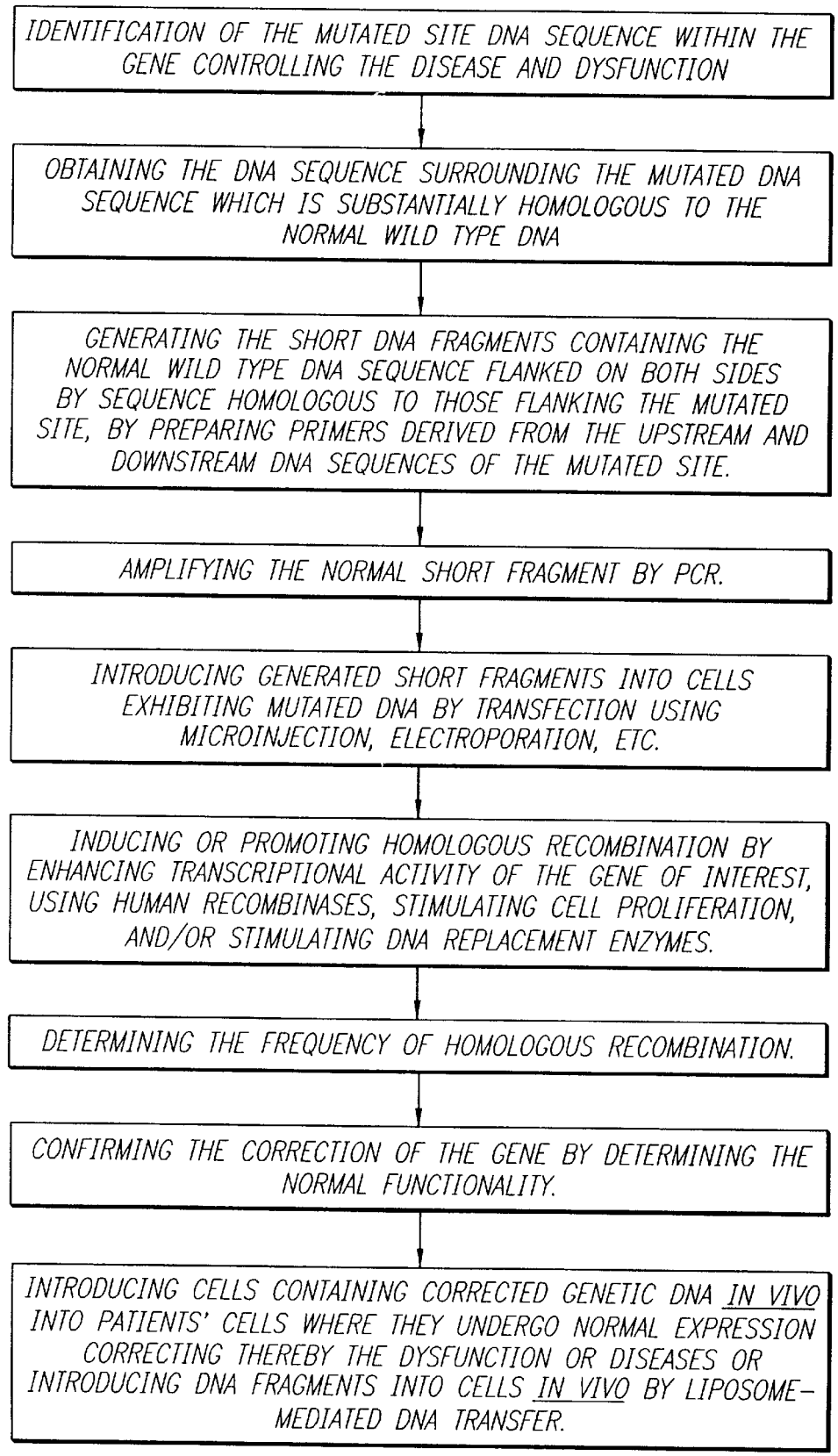
FIG. 2 is a scheme illustrating a method for in vivo and in vitro small fragment homologous replacement (SFHR).

gene with unique restriction enzyme site to be used to introduce mutations.

FIGS. 30A–30B show a new genomic DNA sequence of human CFTR gene exon 10 and flanking intron regions (SEQ ID NO:1).

DEFINITIONS

As used herein:

"Wild-type genomic DNA" means normal genomic DNA that does not contain a mutated site and is not associated with a disease or dysfunction.

"Mutated DNA" means altered DNA sequence within a gene that results in a phenotype abnormality and is manifested as a disease or dysfunction.

"Exogenous DNA" means the altering DNA used for changing by homogenous replacements, endogenous genomic sequences. This DNA can be wild type or mutant genomic DNA depending on the desired outcome.

"Endogenous DNA" means genomic sequence to be altered. This can either be cellular genomic DNA or pathogen genomic DNA. This DNA sequence is resident within a target cell.

"Gene therapy" means treatment of a patient suffering from a disease that results from the expression of genetic material that is mutated, i.e. its nucleotide sequence is different from the nucleotide sequence of a normal individual. Gene therapy thus means replacement of the dysfunctional gene with a functional gene.

DETAILED DESCRIPTION OF THE INVENTION

The current invention primarily concerns a method for utilizing small fragment homologous replacement (SFHR) of a specific region within genomic DNA. The SFHR method for gene therapy or development of transgenic animals is novel and has never before been described in this context.

Briefly, the method comprises identifying X-sequence within genomic DNA, obtaining and introducing (in vivo or in vitro) into cells that contain the given gene a population of small DNA fragments that contain both exon and flanking noncoding sequences. Small fragments of exogenous or DNA which are able to correct mutant genomic DNA sequences by homologous replacement, are expressed. The expressed exogenous DNA or mRNA and protein leads to correction of the dysfunction caused by the mutated gene.

I. A Method for Gene Therapy with Homologous Replacement Using DNA Small Fragments This invention first and foremost concerns a method for in vivo and in vitro correction of genetic defects caused by mutations within the gene controlling a disease or dysfunction. Correction of such mutations is called gene therapy.

The method of the invention utilizes small fragments homologous replacement as an alternative to gene complementation with cDNA disclosed previously. The method is superior to cDNA complementation because it produces a complete replacement of a defective DNA sequence and maintains the sequential integrity of a gene. Moreover, the present method places an exogenous normal functional DNA sequence under the regulation of the endogenous gene promoter and ensures that the gene is expressed at appropriate levels in the cells. None of these effects are accomplished by complementation techniques utilized up to the present time.

The present method may be practiced in vitro, ex vivo or in vivo, depending on the application.

Briefly, once a gene mutation is identified, a small DNA fragment is prepared and comprises a normal DNA sequence for replacement of the region in the gene that contains the mutation. Substitution of the normal (exogenous) for abnormal (endogenous) DNA sequence is conducted, the frequency of homologous replacement is optimized, the occurrence of homologous replacement is detected, and normal functionality is assayed.

DNA or RNA segments isolated from transfected cells are amplified by the polymerase chain reaction (PCR). Appropriate allele-specific oligonucleotide primers for conducting the PCR permit specific synthesis of recombinant and unaltered cellular DNA fragments. These fragments are separated and identified by gel electrophoresis, and the presence of recombined genomic cDNA is confirmed by hybridization with oligonucleotide probes specific for exogenous wild type or mutant sequences. Recombinant cells produced by SFHR are tested for the requisite phenotypic defects, such as, in case of cystic fibrosis, altered chlorine transport associated with the CF gene defect.

Typically, gene therapy according to the invention is achieved by obtaining the small wt (normal) DNA fragments generated by PCR primers that define the region of homology containing the mutated site. The fragments can then be tested in vitro for their ability to substitute the mutated site with the incoming wt normal DNA fragment. In addition, cells are tested for their ability to express the mRNA and for their ability to correct the dysfunction and to restore the normal function of the cell. Upon verification of homologous replacement of the mutated sequence in vitro, these small fragments are introduced in vivo as recombinant cells into an animal. The fragments can be introduced, uncoated or coated with recombinase complexed with liposomes or dendrimers for delivery. The route of introduction is either by any parenteral or any other acceptable route, such as by inhalation of an aerosol containing fragments formulated in liposomes or dendrimer vehicles.

Under conditions promoting annealing and recombination, the mutated site is replaced with the small fragments of normal wt DNA sequence. Conditions that could potentially enhance homologous replacement include, but are not limited to, stimulation of DNA synthesis, activating transcription of the gene of interest with proteins that activate regulatory elements found associated with a given gene (eg., with the promoter/enhancer regions), or by activating cellular DNA repair pathways through damaging DNA. The deleted mutated site is then metabolized within the cell and excreted into the blood stream and out of the body.

Genetic alterations in accordance with this invention, are attained with transformed cell lines and with non-transformed cells, including both germ line cells and somatic cells in vivo and in vitro.

The gene therapy method of this invention may be conducted with a functional DNA sequence that comprises a wild-type genotype lacking the defective sequence causing the disease. Other corrections include insertion of functional DNA sequences other than normal wild-type DNA, which will permit at least quasi normal cell function or at least have beneficial therapeutic consequences for the patient. Although it does not cure it completely, this type of gene therapy alleviates the most crippling forms of a disease. The basis for the success of this invention is the fact that homologous recombination is a process that occurs naturally in the cells.

The principle of naturally occurring homologous recombination is illustrated in FIG. 1. Generally, homologous recombination consist of three steps. First, the DNA segment 1—which is double stranded and the DNA Segment 2—which is also double stranded and genetically similar in that it contains regions that are homologous to segment 1 as seen in FIG. 1A. In the next step, one or both strands (5' to 5' and 3' to 3') of each DNA segment break and attach to the other DNA segment strand at a ligation site (□). The site on the DNA single strand where piece of the DNA bends from its original strand is called branch site (◇). For the last step the branch site is cut and ligated to the other duplex to form recombinant DNA strand within each original double stranded DNA. The recombinant strand consists of the original DNA up to branch site (◇) and from the ligation site (□). Inserted between them is the fragment of DNA from the other duplex strand, which in turn, contains the DNA fragment from the first DNA duplex strand.

The method for the therapy according to the invention comprises several steps.

Step 1 involves identification of the gene controlling the normal function and the dysfunction observed in disease and particularly the identification of the difference in the nucleotide sequences of the normal and dysfunctional gene.

Gene identification and sequencing methods are numerous and known in the art. Any suitable method, such as cleaving using site-specific restriction, nucleus molecular cloning, radioactive labeling, enzymatic replication method and dideoxy method can be used for this purpose. Typically, the sequence of many genes have been identified and are in the public domain. In addition, there are genomic libraries available that contain and make accessible already identified genes and their nucleotide sequences. However, it is occasionally necessary to determine sequences not previously known.

Site of the mutation is derived from the difference between the normal (wild type) sequence and the sequence obtained from the individual suffering from the disease controlled by that particular gene. For example, the most common mutation of the cystic fibrosis transmembrane conductance regulator (CFTR), ΔF508, is found in exon 10, the mutation causing sickle cell anemia is caused by an A to T transversion in the sixth codon of the human β-globin gene resulting in a glutamine to valine substitution in the protein, and the mutation causing xeroderma pigmentosum is due to a deletion of an A in a run of AAA of the exon containing the mutation.

Step 2 involves obtaining wild type DNA sequences homologous to the site of the mutation but which do not contain the mutation.

To this effect primers, short complementary oligonucleotides are synthesized and are typically derived from the sequence of the nucleotides upstream and downstream from the mutation site. Primers are of about 10–50 b.p. preferably about 20 b.p. Primers are used for generation of short DNA fragments to replace mutated genomic sequences, for assaying DNA to ascertain if homologous replacement has occurred and mRNA expression of the DNA that has undergone homologous replacement and to differentiate between wild type (normal) and mutated sequences.

The synthesis of the short homologous DNA fragment may be conducted by methods known in the art, such as the isolation and separation of a wild-type DNA fragment by cleavage with restriction endonucleases, PCR amplification, de novo oligonucleotide synthesis, and/or combinations of enzyme restriction and ligation to produce deletions, additions or the like.

Typically, the normal short fragment to be used as the replacement for mutated sequence is generated by PCR amplification from, for example, a plasmid carrying the appropriate sequence. The plasmid can be verified by restriction enzyme mapping, where restriction enzyme cleavage sites define boundaries of the homologous region. To obtain a short homologous fragments, the plasmid is propagated and digested with restriction enzymes that allow the insert to be isolated, for example, by electrophoresis on a agarose gel. The insert may contain additional sequences, such as 5' and 3' intron sequences. The PCR amplification using primers leads to generation of the small homologous fragment needed for replacement of the mutated site.

PCR amplification is well known in the art and specific conditions needed for the PCR amplification of various life fragments is within skills of the artisan.

Generated short fragments may be coated with a recombinase such as, for example, rec A protein which promotes DNA strand exchange, or with other eukaryotic recombination promoting proteins.

Thus generated short homologous fragments are then introduced into appropriate cells.

Step 3 involves introduction of the short genomic DNA fragments generated in step 2 into cells by transfection using any suitable method.

The cells are, for example, transfected with the DNA fragments comprising the altering DNA sequence and flanking DNA sequences that comprise noncoding DNA by methods such as electroporation, (*Annual Rev. Respir. Dis.,* 138:965–8 (1988)), microinjection according to *Mol. and Cell Biol.,* 2:1372 (1982), complexing the DNA with a lipid layer according to *PNAS* (*USA*), 84:7413 (1987) *ANAS* (*USA*) 90:893–897 (1993) or in a dendrimer (Bioconjugate Chem 4:85–93 (1993).

Step 4 involves confirmation of successful homologous recombination in vitro or in vivo.

Whether or not homologous recombination has occurred may be determined as described below and in the examples by testing a specific function of the cells which have been modified, by analyzing the cellular DNA and/or RNA of the altered cell, by enzyme restriction of the cellular DNA or by immunohistochemical analysis of a gene product expressed by the cells.

Detailed description of these steps is in Sections III and IV.

II. Target Genes for Therapy by Small Fragments Homologous Replacement

The present invention is intended to correct defects associated with genetic human diseases, such as cystic fibrosis, thalassaemias, sickle cell anemia, Fanconi's anemia, retinitis pigmentosa, Xeroderma pigmentosa, ataxia telangiectasia, Bloom's syndrome, retinoblastoma, Duchenne's muscular dystrophy, Tay-Sach's disease, and the like. The method may also be used to alter the DNA sequences of cells with other genetic defects such as cancer. The method only requires that a normal DNA sequence be known or that a normal wild-type DNA fragment be available to provide functional DNA sequences. Other DNAs may be used in this method so as to produce an alteration in cellular DNA with an associated modification of the gene function.

The gene therapy method according to the invention may be utilized to correct a wide variety of genetic diseases, somatic mutations, and pathogen sequences whether nuclear, mitochondrial, or cytoplasmic. Thus, also within the contemplated applications of this invention is the alteration of DNA sequences associated with diseases in animals, or of human genetic diseases originating from animals, where there is present in the human body a genetic material originating from another source.

Genes and the mutation sites for diseases have been in most cells identified and the mutation sites sequences determined. For example, the gene that gives rise to cystic fibrosis, encoding CF transmembrane conductance regulator (CFTR) contains more than 500 mutations that give rise to CF. The most common is a 3-bp, in frame deletion eliminating a phenylalanine at codon 508 (ΔF508). This deletion causes disturbance of chloride transport across epithelial membrane primarily resulting in diseases of gastrointestinal and respiratory systems. Typically, it causes chronic obstructive pulmonary disease, exocrine pancreatic insufficiency and abnormally high sweat electrolytes.

A sickle cell anemia β-globin gene is mutated at the sixth amino acid from the amino terminus of the β chain by replacement of glutamic acid with valine. The sickle cell hemoglobin contains the alteration in the β-globin primary structure which places an aberrant hydrophobic amino acid on the surface of the protein, causing deoxygenated hemoglobin to aggregate, resulting in alteration in the red blood cells shape and impedance of blood flow through capillaries and small venules.

Thalassaemias, the human genetic diseases, are caused by a failure to synthesize adequate amounts of hemoglobin α or β polypeptides. In several thalassaemias, mutations that create stop codons in the middle of the coding sequence prevent completion of the translation of mRNA, in others, mutations prevent normal intron splicing and therefore result in untranslatable mRNAs. Thalassaemias result in chronic microcytic anemias characterized by defective hemoglobin synthesis and ineffective erythropoiesis.

In xeroderma pigmentosum, complementation group G (XP-G, a 245 bp exon, contains a deletion of an adenosine (A) in a run of three adenosine (AAA) of bp 19–21 of the exon. This deletion leads to xeroderma pigmentosum, an inherited disorder in which afflicted individuals are hypersensitive to sunlight, in particular, ultraviolet (UV) light. Exposure to UV light results in skin cancer due to defective DNA repair. In the case of XP-G this defect is associated with an abnormal endonucleus. In addition, XP is often associated with central nervous system (CNS) defects.

Retinoblastoma (Rb) gene involves chromosomal abnormality on chromosome 13 q 14 (the long arm) Retinoblastoma is a malignant abnormality that results from the loss of the Rb gene. Although this gene is normally found in 2 copies (one on each chromosome 13), certain individuals will have one or both copies of the Rb gene deleted. If both copies of the gene are deleted, the onset of malignancy happens rapidly. If one copy is deleted, then a secondary mutation event is required before malignancy occurs. The gene product is involved with regulation of cell proliferation and its loss eliminates the tight controls placed on cell diversion. In addition to retinoblastoma, a deleted or dysfunctional Rb gene has been associated with osteosarcomas and solid tumors in other organs.

There are numerous other genetic disorders and genes that lend themselves to the gene therapy protocols proposed in this invention. While the number of genes that could be altered by SFHR is large, a primary requirement will be knowledge of the DNA sequence that constitutes a given gene. When this information is known or obtained, the invention provides straight-forward method to design a SFHR gene therapy strategy that encompasses both the generation of the incoming therapeutic DNA and the analysis of the target cells after SFHR. In particular, inherited diseases that are the result of small mutation (eg., base changes, small deletions or insertions) are particularly amenable to gene therapy by SFHR. In addition to those diseases mentioned above, SFHR gene therapy could be applied to adenosine deaminase deficiency (ADA), Lesch Nyhan syndrome, Duchenes muscular dystrophy, and Fanconi's anemia, to mention a few. Furthermore, the SFHR gene therapy protocol could be applied to the treatment of certain infectious diseases.

In the treatment of infectious disease, the incoming exogenous DNA contains mutations that inactivate the pathogen by introducing these inactivating mutations into essential genes of the genome of the pathogen. Retroviral pathogens, such as HIV, the agents thought to be responsible for acquired immune deficiency syndrome (AIDS) and the hepatitus B virus are candidates for SFHR gene therapy of infectious diseases. These viruses rely on the integration of the proviral DNA into the cellular genome as part of their replicative cycle. The proviral DNA is the target for the incoming exogenous DNA fragments. A cocktail of fragments with inactivating mutations, that are homologous to several different essential genes within the viral genome is used to disrupt the integrity of the viral genome and the viruses ability to replicate.

Other infectious pathogens with DNA genomes as part of their replicative cycle can also be inactivated by SFHR regardless of whether these genomes are integrated into the host cell. Among these infectious pathogens are bacteria, mycoplasma, and DNA viruses.

III. Small Fragments for Homologous Replacement

A. The normal exogenous DNA fragment of the composition of the invention used for replacement of the mutated sequence may be a double-stranded DNA fragment, a single-stranded DNA fragment or complementary single-stranded DNA fragments. The selection of the exogenous DNA may depend on the source of the DNA, the method of amplification of the DNA and/or the experimental/clinical aim of the user of the method. Most preferably, double-stranded DNA and complementary single-stranded DNA is used.

The exogenous fragment is comprised of the sequence to be altered and flanking DNA. An integral part of this flanking DNA is noncoding DNA, i.e. DNA sequences that do not code for amino acids comprising the gene product of interest. The importance of these sequences for gene therapy by SFHR is that they serve as a buffer to protect the coding (exon) DNA from secondary deleterious mutations that occur during the process of homologous replacement.

The normal DNA fragment is optimally introduced uncoated or coated with a recombinase enzyme. The recombinase is preferably present in a ratio of about 1 protein molecule to every 3 bases. Other ratios, however, may also be used. When the DNA fragment is double-stranded the DNA is preferably denatured prior to contacting it with the recombinase. The recombinases are potentially useful to increase the frequency of pairing between the altering DNA fragment and the cellular DNA fragment to be altered. The enhanced pairing by recombinases is especially useful where the frequency of recombination is low. The use of recombinases is also beneficial to boost the frequency of recombination where biologically effective therapy requires the alteration of a high percentage of target cells.

The altering DNA sequence, as opposed to the altering DNA fragment, is that portion of altering fragment sequence within the altering DNA fragment that is different from that of the endogenous genomic DNA homologue. The altering sequence may comprise 1 to 2000 bases to lengths approaching that of the gene. Preferably, the altering DNA sequence is about 100 to 500 bases long, and more preferably the altering DNA sequence is about 1 to 99 bases long, permitting the alteration of small DNA sequences within the cellular DNA. The altering sequence is to be distinguished from the exogenous DNA fragment, in that the altering DNA is contained within the exogenous DNA fragment. The altering DNA is flanked by homologous sequences that define the region of homology. Moreover, the altering DNA sequence may, upon homologous replacement, result in no net change of cellular DNA size where altering DNA sequence possesses base conversions, in a net decrease of cellular DNA size where the altering DNA sequence possesses a deletion, or in an increase of cellular DNA site if it possesses an insertion. Longer or shorter fragment lengths are all suitable as long as annealing and homologous replacement occur.

B. Once the short homologous normal (exogenous) fragment is generated as described in Section A, it must be introduced into cells containing mutated genetic DNA and the homologous replacement must be successfully achieved. In this respect, such introduction is through the transfection wherein the method is practiced by contacting the normal DNA with cells at about 1 to 200 μg DNA/$10^6$ cells, preferably about 5 to 50 μg DNA/$10^6$ cells. The above DNA amounts and cells are contacted in a suitable aqueous solution at a concentration of about 0.1 μg/ml to 100 μg/ml of the DNA, preferably about 5 to 20 μg/ml of DNA. The proportion may vary depending on the cell type to be transfected, as well as the transfection delivery or administration method used.

When the method is practiced by microinjecting the DNA, about 10 to 100,000 DNA fragments, preferably about 1,000 to 10,000 DNA fragments, are microinjected into each cell nucleus. The DNA is delivered in a volume of about 0.1 to 100 femtoliters, preferably of about 1 to 10 femtoliters per cell nucleus.

During transfection, the cells are grown in an appropriate cell culture medium such as Eagle's minimal essential medium, LHC8e, Dulbecco's minimal essential medium or RPMI 1640, at about 32 to 40° C., preferably about 37° C. Where desirable or where components used for transfection so require, other media solutions may also be used. The incubation temperature may vary according to the requirements of the transfection method used but is generally in the range from about 32 to 40° C. The cells are incubated with the exogenous short DNA fragments for a period of about 1 to 21 days, to periods of great length, preferably about 2 to 14 days. Culture conditions which are selected to maximize cell growth rate generally also optimize homologous recombination.

C. Homologous recombination within the cells is achieved and promoted with various agents with which the fragments are either complexed or coated.

The exogenous short DNA fragments are coated, for example, with a recombinase enzyme selected from the group consisting of UVXS, Rec A, yeast recombinase, human recombinase, and RAD$^{51}$ yeast recombinases including DMC and HPPI for delivery into the cell. In alternative, the fragments are left uncoated, or complexed with a protein, such as gramicidin S or defensins, and then coated with a lipid in a proportion DNA/protein/lipid of about 1 μg: 0.5 μg–50 μg:1 nmol–500 nmol, preferably about 1 μg:1 μ–20 μg:10 nmol–250 nmol. The combination of the DNA with the lipid and protein components may be done in one step or by first contacting the DNA, whether coated with a recombinase or uncoated, with the protein, and thereafter adding the lipid.

The normal DNA fragment whether uncoated, coated or complexed is preferably delivered into the cell complexed with protein-lipid complexed, complexed a lipid layer or with a dendrimer or by electroporation or microinjection according to Examples 15–17.

When the altering DNA fragment is delivered into the cell by microinjection, the conditions shown in the examples are preferably utilized. However, other conditions known in the art may also be utilized.

The choice of the transfection method depends on the type of cell to be transfected, the frequency of recombination required and the number of cells to be transfected. Nuclear microinjection typically produces higher rates of transfection and thus requires a lesser DNA:cell ratio. As microinjection is a manipulative technique practiced with a relatively small number of cells, this technique is preferable to conserve scarce amounts of DNA. Other methods such as lipid or dendrimer complexes, lipid-protein complexes and electroporation require higher DNA concentrations per set number of cells. These methods, while somewhat less efficient, are particularly applicable when large numbers of cells are being transfected since the cells need not be individually manipulated. The DNA-lipid, DNA-dendrimer, and lipid-DNA-protein complex transfection techniques are especially applicable to in vivo transfection. Using the DNA complex transfection, the DNA is protected from degradation. Therefore, because less cell lethality is encountered, the method is compatible with intracorporeal injection or administration.

IV. Homologous Replacement in Specific Diseases

Homologous replacement according to the invention has been tested, successfully achieved and a correction of a disfunction in cystic fibrosis has been observed. Other diseases subject to the same treatment are sickle cell anemia and xeroderma pigmentosum group G.

The correction of a genetic defect by the gene therapy according to a method of the invention is exemplified herein for the cystic fibrosis. Cystic fibrosis disease is corrected by substitution, with a normal 491 base pair DNA fragment, of the defective DNA sequence containing the ΔF508 mutation of the genomic DNA of a CF cell line, found in exon 10 (192 bp) and in the 5'(163 bp) and 3'(136 bp) flanking introns. This substitution is attained by small fragment homologous replacement. The immortal cell line used was a cystic fibrosis (CF) line derived from a tracheal epithelial cells homozygous for the ΔF508 mutation. This is a post crisis cell line that is defective in cAMP-dependent Cl$^-$ ion transport, secretes chloride in response to a calcium ionophore, and expresses CFTR mRNA.

The cells were prepared from CF tracheal epithelial cells from an autopsy specimen and were isolated uncultured by procedures described in *In Vitro Cell Dev. Biol.*, 26:411 (1990) and in *Am. J. Physiol. Lung Cell Mol. Physiol.*, 261:L485 (1991). A pure culture of primary airway epithelial cells was transfected by calcium phosphate precipitation with a linearized plasmid such as pSVori$^-$, as previously described in *PNAS (USA)*, 89:5171 (1992); or in *In Vitro Cell Dev. Biol.*, (1990), supra. The transfected cultures were grown in an appropriate medium at, 37° C. until cells with the desired growth characteristics appeared, according to *PNAS (USA)*, 85:9591 (1988) and *BioTechniques*, 5:740 (1987). The transformants were isolated by trypsinization and regrown using methods known in the art.

In preferred embodiment of the present composition, the altering DNA fragment is enveloped by a lipid layer, encapsulated by a lipid and a protein layer, or is completed as a DNA-dendrimer.

The DNA sequence to be corrected or altered comprises a mutated DNA sequence encoding the cystic fibrosis transmembrane conductance regulator (CFTR) protein and the altering DNA sequence comprises a functional (normal) allele of the CFTR gene. A wild type allele has been found to carry the normal nonmutated sequence and is therefore suitable for homologous recombination. Using available DNA libraries and the normal CFTR gene sequence, functional wild-type DNA fragments homologous to CF mutations can be prepared.

Numerous human epithelial CF cell lines, carrying the cystic fibrosis mutations have been transfected with small fragments of human genomic DNA that has been heat denatured before the transfection procedure. The CF cell lines that have been transfected with wild-type (wt) CFTR sequences include ΣCFTE29o-, CFPAC-1, and ΣCFNPE14o-. These CF cell lines have all been shown to be homozygous for the ΔF508 mutation. In addition, nonCF human epithelial cells (both transformed and primary) have been transfected with genomic DNA fragments containing the ΔF508 mutation.

The cells have been transfected by microinjection, electroporation, and liposome or dendrimer—DNA complexes according to examples. The cells were assayed for the presence of incoming DNA sequences at the appropriate genomic locus, for the expression of CFTR mRNA containing incoming exon sequences, and for the functional correction of the CF cAMP-dependent ion transport defect.

The additional studies include transfection of primary nonCF and transformed nonCF and CF epithelial cells with fragments of genomic DNA containing either wt or ΔF508 CFTR sequences and a unique restriction site introduced by site directed mutagenesis. The restriction site (Xho I) contains a silent mutation in exon 10 that does not alter the amino acid sequence or the wild-type CFTR protein sequence. This restriction enzyme site allows for an additional verification of the homologous exchange. Fragments with the Xho I restriction enzyme site were cloned into the pCR II vector designed for incorporating PCR amplification products. The fragments were generated by PCR site directed mutagenesis outlined in FIG. 3. The sequences used for generating the fragment with the Xho I restriction site were based on the published data.

FIG. 3 shows diagrammatic representation of the generation of fragments 491 (N) and 488 (ΔF) that contain wtCFTR and Δ508 CFTR sequences, respectively. The fragments contain a second mutation in exon 10 (a G>C conversion at base pair 197 of the 491 bp fragment) that gives rise to an Xho I cut site. This mutation is in the third base of codon 11 (in exon 10) and does not change the amino acid determined by this codon. The M3 primer is a 21 base sense (+) oligonucleotide (5'-GATTATGGGAGAACTCGAGCC-3') (SEQ ID NO:84) that has been generated with the G>C conversion at base 197 and comprises bases 182–202 of the sense strand of the 491 bp fragment. The M4 primer is a 21 base antisense (−) oligonucleotide (5'-ACCCTCTGAAGGCTCGAGTTC-3') (SEQ ID NO:85) that has a C>G conversion at base 197 of the antisense strand and comprises bases 212–192 of the antisense strand of the 491 bp fragment. The initial amplification with CF1/M4 and M3/CF5 gives fragments that are 212 and 310 bp, respectively for the wtCFTR sequences. For ΔF508 CFTR the fragments are CF1/M4 (212 bp) and M3/CF5 (307 bp), since the ΔF508 mutation deletes bases 293–295 of the 491 bp wtCFTR fragment. Restriction digestion of the 491 bp or 488 bp fragments with Xho I yields digestion fragments of 199 bp and 292 or 289 bp, respectively.

The strategy for PCR and restriction digest analysis of genomic DNA and CFTR MRNA following transfection with the fragment carrying the Xho I restriction site is indicated in FIGS. 4 and 5. The primer pairs used for PCR analysis were designed to be specific for the genomic locus in the region of exon 10 that contains the homologous region. Primers indicated in FIGS. 4 and 5 are defined in Table 1.

TABLE 1

Sequences of Primers and Oligonucleotides

| CF 1 | (S) | 5'-GCAGAGTACCTGAAACAGGA-3' | SEQ ID NO. 2 |
| CF1B | (S) | 5'-CCTTCTCTGTGAACCTCTATCA-3' | SEQ ID NO. 3 |
| CF5 | (A) | 5'-CATTCACAGTAGCTTACCCA-3' | SEQ ID NO. 4 |
| CF6 | (A) | 5'-CCACATATCACTATATGCATGC-3' | SEQ ID NO. 5 |
| CF7B | (S) | 5'-CCATTAAAGAAAATATCATTGG-3' | SEQ ID NO. 6 |
| CF8B | (S) | 5'-CCATTAAAGAAAATATCATTGG-3' | SEQ ID NO. 7 |
| CF7C | (A) | 5'-ATAGGAAACACCAAAGATGA-3' | SEQ ID NO. 8 |
| CF8C | (A) | 5'-ATAGGAAACACCAATGATAT-3' | SEQ ID NO. 9 |
| CF9 | (S) | 5'-ACTTTAAAGCTGTCAAGCCGTG-3' | SEQ ID NO. 10 |
| CF14 | (A) | 5'-CTGTATTTTGTTTATTGCTCCAA-3' | SEQ ID NO. 11 |
| CF 17 | (S) | 5'-GAGGGATTTGGGGAATTATTTG-3' | SEQ ID NO. 12 |
| CF 22 | (A) | 5'-CTTGCTAAAGAAATTCTTGCTC-3' | SEQ ID NO. 13 |
| oligo N | (A) | 5'-CACCAAAGATGATATTTTC-3' | SEQ ID NO. 14 |
| oligo ΔF | (A) | 5'-AACACCAATGATATTTTCTT-3' | SEQ ID NO. 15 |
| C16B | (B) | 5'-CTTTTCCTGGATTATGCCTGGCAC-3' | SEQ ID NO. 16 |

The nucleotide sequence of CFTR DNA primers as described above were derived from published data. Sense (S) and antisense (A) primers are as indicated. The sense DNA strand codes for mRNA.

FIG. 4 is a schematic representation of the PCR analysis of genomic DNA that is intended to insure amplification from the genomic locus encompassing the homologous region defined by the incoming DNA fragment. Primers CF1B and CF6 (Table 1) are outside the region of homology and amplify only DNA derived from genomic DNA around the region of homology. Primers CF7B and CF8B are sense (+) allele specific primers for wt and ΔF508 CFTR sequences, respectively. In combination with CF6 (−) these primers give rise to a fragment that is either 414 bp or 411 bp that represent the presence of wt or ΔF508 CFTR sequences, respectively. The CF7C and CF8C primers are antisense (−) and are allele-specific for wt and ΔF508 CFTR sequences, respectively. In conjunction with the sense (+) primer, CF1B they amplify fragments that are 391 bp or 389 bp wt- or ΔF508-specific, respectively. The restriction analysis with Xho I of the CF1B/CF7C or CF8C amplification product gives rise to two different restriction fragments of 283 bp and 109 bp (N) or 106 bp (ΔF). If a secondary amplification is carried out with primers CF1/CF7C or CF8C, then the restriction fragments will be 199 bp and 109 bp (N) or 106 bp (ΔF).

FIG. 5 is a schematic representation of the PCR analysis of genomic DNA illustrating strategy for RT-PCR analysis of CFTR mRNA by spanning intron/exon boundaries. The resultant mixture of 473 bp (N) or 470 bp (ΔF) fragments was then purified and reamplified by allele-specific PCR with primers CF17/CF7C OR CF17/CF8C. The resultant 330 BP (n) OR 327 BP (ΔF) fragments were digested with Xho I to determine if the genomic locus which has undergone homologous replacement is transcribed. The restriction fragments were either 221 bp and 109 bp (nonCF) and 221 bp and 106 bp (ΔF508).

FIG. 6 is an analysis of CFTR DNA from CF cells transfected with 491 nucleotide DNA fragments in the dendrimer-DNA complex.

FIG. 6 is PCR amplification of the CF1B/CF6 product and autoradiographic analysis of the DNA transferred to Gene Screen Plus filters and hybridized with $^{32}$P-labeled oligo N and oligo ΔF probes. The DNA in each lane is as follows: lane 1 control CFNPE14o- cell DNA; lane 2, DNA from CFNPE14o- cells transfected with uncoated DNA fragments; lane 3, DNA from CFPE14o- cells transfected with rec A coated DNA; lane 4, H$_2$O; lane 5, DNA from nonCF (N/N) lymphocytes; lane 6, DNA from ΔF508 homozygote (ΔF/ΔF) lymphocytes; lane 7, ΔF508 heterozygote (Δ/N) lymphocytes. Densitometric analysis compared the relative hybridization efficiency of the oligo N (a) and oligo ΔF (B) probe to the heterozygote (N/Δ) lymphocyte DNA and N/ΔF lymphocytes (lanes g and i) indicated the presence of wtCFTR sequences. Analysis for ΔF508 sequences indicated their presence in all samples except the control N/N lymphocyte DNA (lane g). No wtCFTR sequences were indicated in control nontransfected and mock-transfected (lanes b, c, and d) or the ΔF/ΔF lymphocyte (lane h) DNA. A 123-bp marker was used (lane a) and H$_2$O controls were in lane j in all cases. Primers were as in FIG. 7.

Hybridization of the 771/768-bp DNA fragments with allele-specific normal (oligo N) or ΔF508 (oligo ΔF) probes indicated wtCFTR sequences at exon 10 genomic locus from ΣCFNPE14o-cell cultures transfected via the Starburst dendrimer-DNA complex as seen in FIG. 6. Densitometric analysis indicated a replacement frequency of 7% for non-rec A coated cells and 3% for cells transfected with rec A-coated DNA. The intensity of the oligo N probe was 1.1> that of the oligo ΔF as determined from hybridization to the PCR products generated from amplification of heterozygote lymphocyte DNA (lane 7). The values for the oligo Δ were multiplied by 1.1 for normalization. Because there was a smear of background hybridization by the oligo N probe to the product of the amplification of DNA from nontransfected control cells, this background was subtracted from the autoradiographic signal detected following hybridization with the oligo N probe. The relative frequency of the wtCFTR in the population of 771/768-bp fragments was determined as (DN−DB)/(Dn−DB)+DΔF, where DN is the densitometric value for the oligo N hybridization, DB is the densitometric value for the background hybridization of the oligo N probe, and DΔ is the normalized densitometric value for the oligo ΔF hybridization.

Figure 7A:
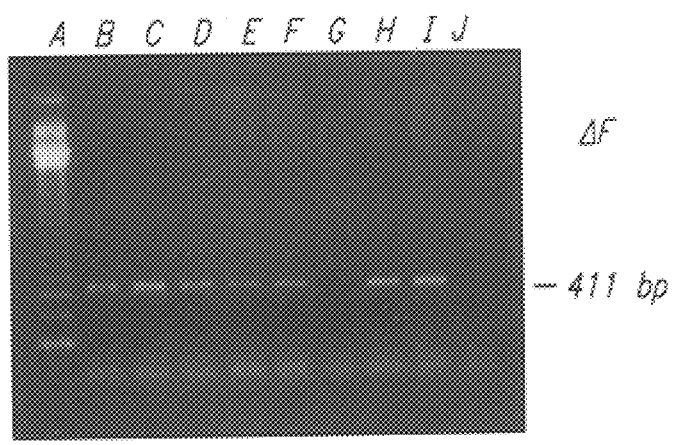
FIGS. 7A–7B are allele-specific PCR analysis using primers CF7B/CF6(N) or CF8B/CF6(ΔF).
Figure 7B:
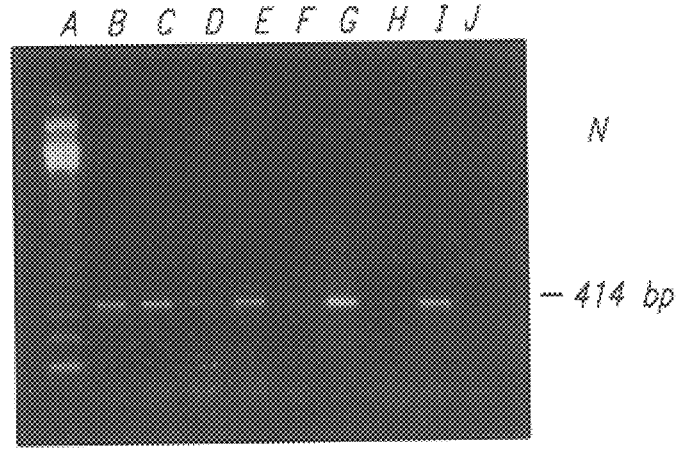

FIG. 7 shows allele-specific PCR analysis (using primers CF7B/CF7 (N) or CF8B/CF7 (ΔF). FIG. 7 is an analysis of ΣCFTE29o- cells transfected either with the Starburst™ dendrimer-DNA complex (lanes b and c) or the gramicidin S-DNA-lipid complex (lanes d and e). DNA was either uncoated (lanes b and d) or coated with rec A (lanes c and e). In FIG. 7A isolated DNA was amplified using primers CF8B/CF6 (top) and in FIG. 7B using primers CF7B/CF6 (bottom). Control samples were of DNA from (lane f), ΣCFTE/con; (lane g), nonCF (N/N) lymphocytes; (lane h), ΔF508 homozygote (Δ/ΔF) lymphocytes; (lane i), ΔF508 heterozygote (Δ/N) lymphocytes; and lane j, H20. Wild-type CFTR sequences were only detected in the samples from transfected cells, and in the N/N and ΔF/N lymphocyte DNA samples.

Figure 8A:
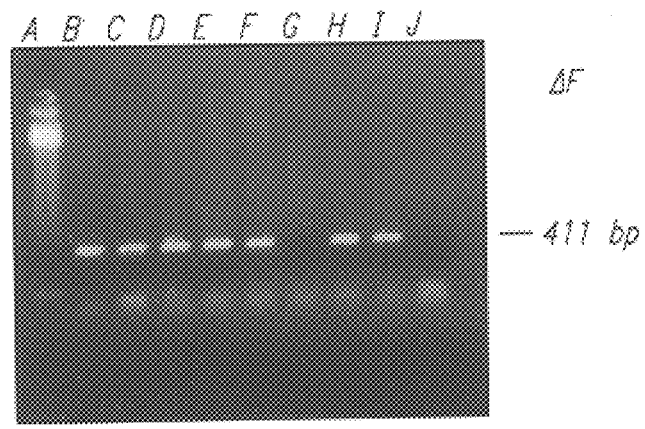
FIG. 8 is allele specific PCR analysis of CFPAC-1 cells transfected with rec A coated and uncoated 491 base fragments.
Figure 8B:
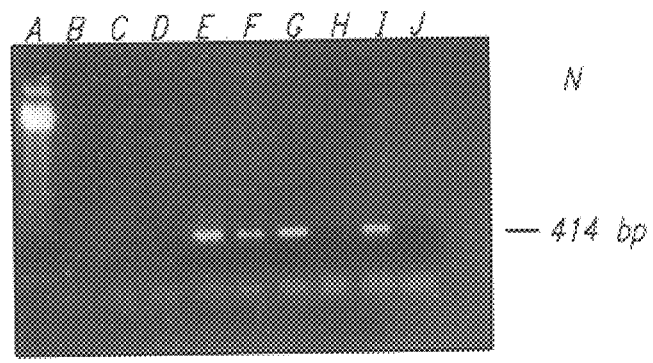

FIG. 8 shows allele-specific PCR analysis of CFPAC-1 cells transfected with rec A coated and uncoated 491 base fragments using the Starburst™ dendrimer-DNA complex to introduce the homologous DNA into the cells. PCR analysis of CFPAC-1 DNA from control nontransfected (lane b) and mock-transfected without DNA (lanes c and d). Cells transfected with fragment 9 (lanes e and f) and control DNA from the N/N and N/ΔF508 lymphocytes (lanes g and i) indicated the presence of wtCFTR sequences. Analysis for ΔF508 sequences indicated their presence in all samples except the control N/N lymphocyte DNA (lane g). No wtCFTR sequences were indicated in control nontransfected and mock-transfected (lanes b, c, and d) or the Δ/Δ lymphocyte (lane h) DNA. A 123-bp marker was used (lane a) and H20 controls were in lane (j) in all cases. Primers were as in FIG. 7.

Where DNA from transfected ΣCFTE29o- cells as seen in FIG. 7 or CFPAC-1 cells, as seen in FIG. 8, were submitted to direct allele-specific PCR amplification of genomic DNA. Cells showed site-specific replacement of ΔF508. Cells transfected with gramicidin-S-DNA-liposome (ΣCFTE29o-) or dendrimer-DNA (ΣCFTE29o- an CFPAC-1) complexes were harvested at 3 and 10 days after transfection and the DNA was PCR analyzed with CF7B (N)/CF6 or CF8B (ΔF)/CF6. This allele-specific amplification indicates the presence of wtCFTR sequences in the transfected cells. The respective 414 (N) of 411-bp (ΔF) PCR products visualized by ethidium bromide staining from control DNA confirmed the specificity of the N and ΔF primer pairs.

Additional experiments with electroporation gramicidin S-DNA-lipid, or DNA-dendrimer transfection of the wtCFTR fragments also showed homologous replacement at the level of genomic DNA in treated CF cells.

Because the allele-specific PCR employed one primer within the region of homology, there was a concern that template switching might be responsible for detection of wtCFTR sequences at the appropriate genomic locus in mutant cells. To test the possibility that any 491 nucleotide ssDNA fragments remaining in the cell after 6 or more days might contribute to PCR amplification of the 414/411-bp fragment reconstruction experiments were used. High molecular weight genomic CFPAC/con DNA was incubated with a range of uncoated 491-base DNA fragments. The amounts of fragments varied from the equivalent of 106 copies of the 491 base fragment per cell (assuming 5 pg DNA per cell) to 0.1 copy per cell. Results are seen in FIG. 9.

Figure 9:
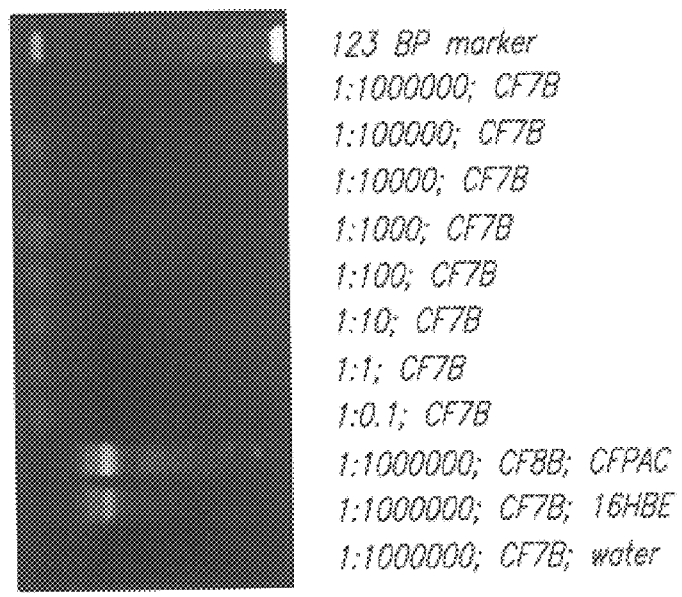
FIG. 9 illustrates reconstitution experiment with DNA nontransfected CFPAC-1 or 16HBE14o-cells mixed with 491 nucleotide wt CFTR fragment.

FIG. 9 illustrates reconstitution experiment with DNA from nontransfected CFPAC-1 or 16HBE14o- cells mixed with 491 nucleotide wtCFTR fragment used in targeted gene replacement. Fragments were mixed with cellular DNA at concentrations that reflect a range of fragments (106 to 10-1) per cell. PCR analysis was allele-specific and used primers CF7B/CF6 (N) or CF8B/CF6 (ΔF). Control amplifications were carried out in the presence of the equivalent of $10^6$ 491-nucleotide fragments per cell with the appropriate wt CFTR (16HBE14o- or ΔF (CFPAC-1) primers.

In no instance was spurious amplification of a 414 bp wtCFTR fragment detected. Amplification of the control DNA with the appropriate primer pair, such as for example, CFPAC DNA with CF8B/CF6 and 16HBE14o- DNA with CF7B/CF6) gave a PCR product at the correct molecular size. It also appeared that the presence of large excesses of the fragment did not interfere with the amplification of the appropriate product. Other reconstruction studies showed similar results with or without rec A coating.

While homologous recombination is a primary goal of the gene therapy, equally important is expression of corrected gene as mRNA. Only if such expression happens, the normal gene function is restored.

Figure 10:
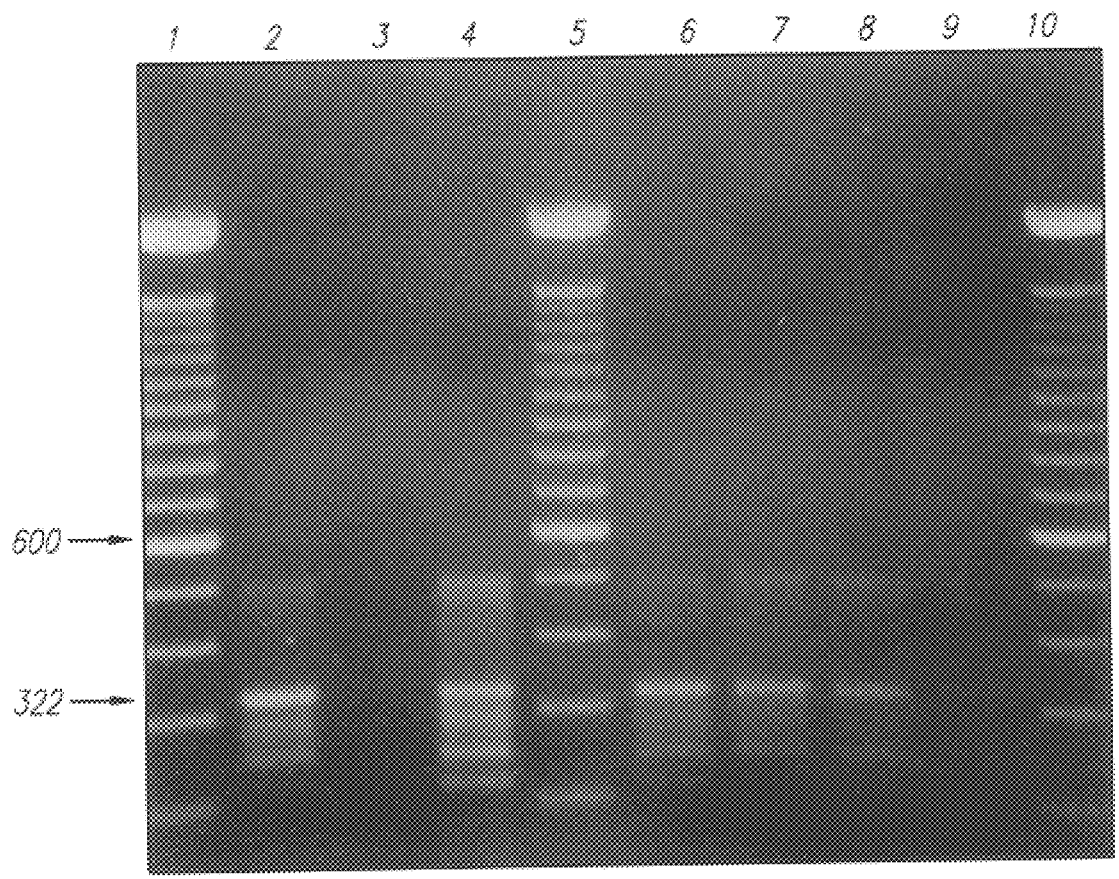
FIG. 10 is an autoradiographic analysis of DNA amplified from first-strand CFTR cDNA from ΣCFTE29o- cells.

FIG. 10 shows analysis of DNA amplified from first-strand CFTR cDNA from ΣCFTE29o- cells electroporated with rec A-coated 491-nucleotide fragments (lanes 6 and 7) or with rec A-coated or DNA fragments not coated with rec A, encapsulated as a gramicidin S-DNA-lipid complex (lanes 8 and 9, respectively). Cells were electroporated or transfected with the rec A-coated or uncoated 491 nucleotide fragments, and cytoplasmic RNA was isolated 7 days later. CFTR mRNA was reverse-transcribed into first-strand CFTR cDNA. The cDNA was amplified with CF17 (exon 9) primer and allele-specific primers for either normal (oligo N, 322-bp fragment) or mutant (ΔF,321-bp fragment) sequences. A 321-bp PCR fragment was produced in DNA from transfected ΣCFTE29o- cells when first-strand cDNA was amplified directly with the CF17/ΔF primer pair in control cells (lane 4). However, only control normal 16HBE14o- cells (lane 2) and electroporated and transfected cells (lanes 6–9) amplified with CF17/N produced a 322-bp band. No DNA product was observed when cDNA from ΣCFTE/con cells was amplified with the CF17/N primers (lane 3). Marker DNA (100-bp) is located in lanes 1, 5, and 10.

Results shown in FIG. 10 shows that corrected CFTR DNA has been expressed as mRNA and normal CFTR function has been restored. As seen in FIG. 10, allele-specific RT-PCR amplification of mRNA indicates that wtCFTR was transcribed in transfected cells. Amplification of genomic DNA was circumvented because the primers require amplification across intron/exon boundaries. Amplified cDNA from normal 16HBE14o- cells (lane 2) and experimentally transfected CF cells (lanes 6–9) yielded DNA fragments with the CF17/oligo N (322-bp). Amplified cDNA from ΣCFTE/con cells only showed a DNA fragment after amplification with the CF17/oligo ΔF (299-bp) (lane 4) but not with the CF17/oligo N primers (lane 3). Two separate electroporation experiments with the 491 nucleotide wtCFTR ssDNA fragments (lanes 6 and 7) showed the presence of wtCFTR mRNA. In addition, RNA from gramicidin S-DNA-lipid-transfected ΣCFTE29o- cells also contained wtCFTR mRNA whether or not the 491 nucleotide fragments were coated with rec A (lanes 8 and 9). Allele-specific Southern hybridization of the 322/321-bp amplification products with the $^{32}$p-labeled N oligonucleotide probe specifically hybridized to cDNA from all transfected cell cultures. No hybridization was detected ΣCFTE/con cells amplified with the CF17/ oligo N or CF17/oligo ΔF (data not shown). These analyses strongly suggest that genomic DNA was homologously replaced with the wp 491 nucleotide ssDNA fragments at the ΔF508 CFTR DNA locus, resulting in a corrected gene transcribed as wtCFTR mRNA. Determination of restoration of normal function of the corrected gene is seen in FIG. 11.

Figure 11:
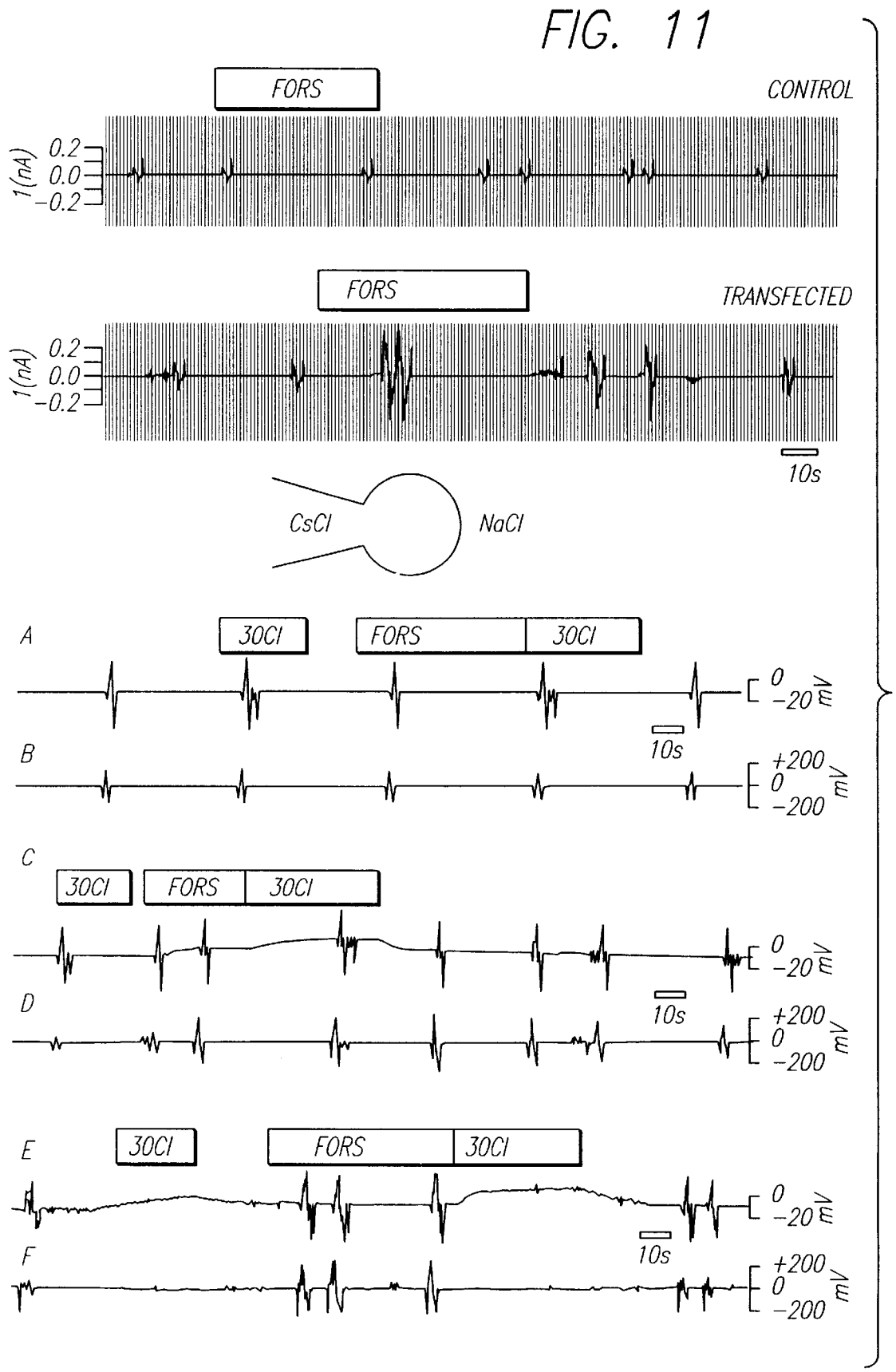
FIGS. 11A–11F show continuous recording measuring cAMP-dependent Cl current of nontransfected and transfected ΣCFTE29o- cells.

FIG. 11 shows continuous recording measuring cAMP-dependent Cl current of a nontransfected ΣCFTE29o- cells (upper panel) and those transfected with the wtCFTR 491 base fragments (lower panel). The cells were exposed to 10 μM forskolin (Fors) for the duration indicated by the box. The patch pipette contained CsCl to minimize the contribution of K⁺ currents the analysis. An increase in the amplitude of the deflection from the baseline (0.0 nA) indicates an increase in the cAMP-dependent Cl current. FIG. 11B shows continuous recordings of three different whole cell patch clamp experiments with ΣCFTE/con (control) (A, B), 16HBE14o- (C, D), ΣCFTE29o-/SD– (E, F) cells. The cell membrane potential in each experiment was measured continuously (A, C, E,; current clamp) and the whole cell current was measured in intervals by voltage clamping to ±30 mV (B, D, F). Forskolin (Fors; 10 μM) had no effect on the whole cell current of the ΣCFTE/con cells (A) and Cl conductance could not be detected by reduction of the bath Cl concentration to 30 mM (30Cl;B). In contrast Fors increased whole cell currents in 16HBE14o- (D) and in ΣCFTE29o-/SD– (F) cells. Moreover, after stimulation a significant increase in the membrane depolarization was observed following reduction of the bath Cl (30Cl; C, E) and indicates activation of Cl conductance. All effects were reversible.

Figure 6A:
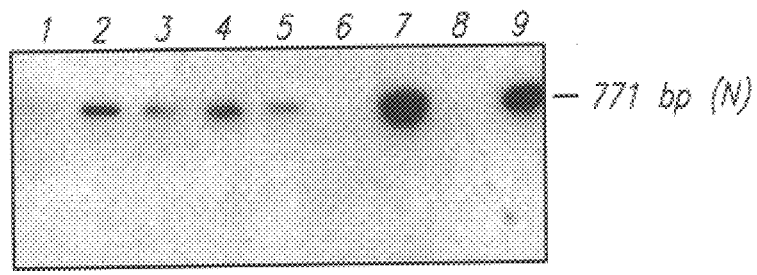
FIGS. 6A–6B are an autoradiographic analysis of CFTR DNA from CF cells transfected with 491 nucleotide DNA fragments in the dendrimer-DNA complex.
Figure 6B:
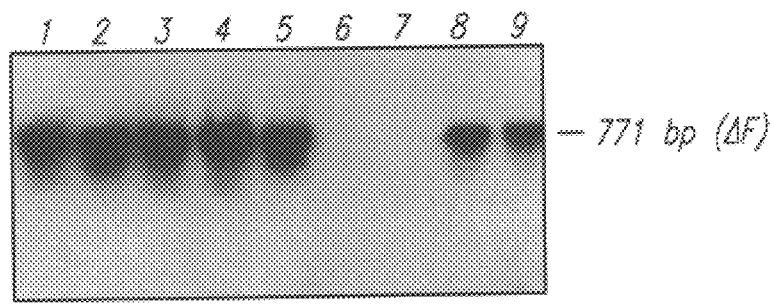

Patch clamp analysis of ΣCFTE29o- cells transfected with the gramicidin S-DNA-lipid (GS) or the dendrimer-DNA (SD) complex was carried out. The homologous DNA fragment was either uncoated (GS– or SD–) or rec A-coated (GS+ or SD+). This analysis revealed that a portion of the cells now responded to stimulation with forskolin (10 μM) with an increase in Cl conductance ($G_{Cl}$) (FIG. 6a). When compared to that seen in nonCF, 16HBE14o- (FIG. 6b, panel D, cells the level of $G_{Cl}$ was similar for the responding transfected cells (FIG. 6b, panel F), while the control nontransfected CF cells failed to show any increase in cAMP-dependent $G_{Cl}$ (FIG. 6b, panel B). In 21 experiments with ΣCFTE/con cells and in 71 of 78 experiments with transfected ΣCFTE29o- (GS–, GS+, SD–, SD+) cells, there was no increase in gcl following exposure to forskolin (ΣCFTE/T–). However, 7 of 78 experiments with transfected cells (9%) showed a forskolin-induced Cl conductance (ΣCFTE/T+) (Table 2).

TABLE 2

Breakdown of ΣCFTE29o- Patch Clamp Analysis

| ΣCFTE29o- | Control | GS/– | GS/+ | SD/– | SD/+ |
|---|---|---|---|---|---|
| Experiments (n) | 21 | 22 | 11 | 15 | 30 |
| Responses (n) | 0 | 3 | 0 | 1 | 3 |

ΣCFTE29o- cells transfected with either a gramicidin S-DNA-lipid (GS) or the Starburst™ dendrimer-DNA (SD) complex. The encapsulated 491-bp DNA fragment was either rec A coated (GS+, SD+) or uncoated (GS– or SD–). Each experiment represents the patch clamp analysis of a single cell. Responding cells are those that showed a Cl conductance and a change in membrane potential following stimulation with forskolin and a reduction in the bath NaCl concentration to 30 mM.

In these 7 positive experiments, forskolin reversibly induced an increase in the whole cell conductance as well as an increase in membrane depolarization (ΔPD) following reduction of the batch Cl concentration to 30 mM (Table 3) (FIG. 6b, panel E). Comparable increases in the whole cell Cl conductance were seen in ΣCFTE/con, ΣCFTE/T−, and ΣCFTE/+ cells after exposure to ionomycin (G Iono; 5×10−7 M) and hypotonically induced cell swelling (g Hypo) (Table 3).

TABLE 3

| Whole Cell Cl Transport Responses | | | |
|---|---|---|---|
| cAMP -Dep Cl Transport | ΣCFTE/con (n = 21) | ΣCFTE/T− (n = 71) | ΣCFTE/T+ (n = 7) |
| Gcon (nS) | 3.9 ± 0.8 | 4.4 ± 0.4 | 4.2 ± 0.9 |
| G For (nS) | 3.9 ± 0.8 | 4.5 ± 0.5 | 7.7 ± 1.5 |
| ΔPD(30 Cl) (mV) | 0.0 ± 0.0 | 0.1 ± 0.1 | 8.1 ± 1.3 |
| Ca + 2 -Dep Cl Transport | ΣCFTE/con (n = 6) | ΣCFTE/T− (n = 29) | ΣCFTE/T+ (n = 3) |
| Gcon (nS) | 2.7 ± 0.8 | 3.7 ± 0.5 | 2.1 ± 0.3 |
| Glono (nS) | 5.8 ± | | |

Cells were used for patch clamp within 1–4 days after plating. The bath perfusion rate was 20 ml/min and correspond to a bath exchange rate of twice per second. Standard bath solution contained (mM): NaCl, 145; $K_2HPO_4$, 0.4; $CaCl_2$, 1.3; $MgCl_2$, 1; d-glucose, 5. Pipette solution was (mM): $CsC_1$, 125; $Na_2PO_4$, 0.4; $NaH_2PO_4$, 1.6; EGTA, 1; $CaCl_2$, 0.5; $MgCl_2$, 1:D-glucose, 5; ATP, 1. The access conductance was controlled in each experiment within a range of 40–130 nS. Membrane voltages were recorded continuously using the current clamp mode of the patch clamp amplifier and whole cell current was measured in regular intervals by clamping the membrane voltage to ±30 mV in steps of 10 nV. Whole cell conductance ($G_{Cl}$) was calculated from the measured whole cell current (I) and the applied clamp voltage (Vc). All experiments were carried out at 37° C. $G_{Cl}$ was determined after stimulation by 10 $\mu$M forskolin ($G_{For}$), by 0.5 $\mu$M ionomycin ($G_{Iono}$), or by reducing the NaCl concentration in the bath to 72.5 $\mu$M for hypotonic cell swelling ($G_{Hypo}$). The Cl conductance of unstimulated control cells ($G_{con}$) was determined separately for each treatment. Increases in membrane depolarization were determined after reduction of the bath Cl concentration ($\Delta_{PD}$ 30 Cl). ΣCFTE/con are forskolin stimulated nontransfected control cells; ΣCFTE/T− are nonresponding, forskolin stimulated transfected cells; ΣCFTE/T+ are responding, forskolin stimulated control cells.

Results in this study demonstrate that (a) ΔF508 CF epithelial cells undergo homologous replacement at the CFTR mutation with small fragments of wtCFTR DNA, resulting in a corrected genomic ΔF508 locus; (b) rec A protein-coated and uncoated ssDNS fragments can be used in the transfection of cultured human cells; (c) cystic fibrosis ΔF508 mutations corrected in genomic DNA result in production of normal CFTR mRNA; and (d) CF cells corrected by homologous replacement display intact cAMP-dependent Cl transport.

The studies described here indicate that small 491 nucleotide ssDNA CFTR fragments find their genomic homologues when introduced into human airway epithelial cells and replace endogenous genomic DNA. The ΣCFTE29o-, CFNPE14o-, and CFPAC-1 cell lines have the same 3-bp ΔF508 mutation in all copies of the CFTR gene, and the appearance of wtCFTR sequences in the genomic DNA and mRNA of cells transfected with 491-nucleotide ssDNA can probably be attributed to homologous DNA replacement (FIG. 2, 3, 6, 7, and 9) and not to a PCR artifact such as template switching (FIG. 9). This is further supported by the restoration of cAMP-dependent Cl transport in a subpopulation of transfected cells (FIG. 11 and Tables 2 and 3). It is this subpopulation of cells with the cAMP-dependent Cl transport detected in patch clamp experiments that carries at least one wtCFTR allele at exon 10 locus effectively making them heterozygotes.

Evaluation of one possible PCR artifact tested whether the 491-nucleotide ssDNA fragments in the cells contribute to amplification of the 414-bp fragments. These reconstruction experiments indicated that nonrecombined 491-nucleotide ssDNA do not appear to participate in the generation of 414-bp fragments (FIG. 9). This finding indicates that template switching did not occur at the cell DNA-fragment ratios or under the amplification conditions used in the above studies. Moreover, PCR amplification of mRNA-derived first-strand cDNA and the restoration of cAMP-dependent Cl transport further reinforces the conclusion that homologous DNA replacement did, in fact, occur.

The reproducibility of these studies, both in the number of experiments and in the equivalent results from different gene transfer regimens, also supports the general conclusion that gene correction with small ssDNA fragments has occurred in the transfected cells. Homologous replacement was detected in one out of one microinjection experiment with rec A-coated DNA in three of three electroporation experiments with rec A-coated DNA, or in six of ten lipid-protein experiments and nine of 10 dendrimer experiments with either uncoated or rec A-coated DNA. Taken together, the results obtained in 19 separate experiments show that homologous replacement with relatively small DNA fragments (491 nucleotide ssDNA fragments) are useful for treatment of CF cells.

The patch clamp analysis shows that within a population of transfected CF cells there appears to be a significant subpopulation cells in which cAMP-dependent Cl transport defect has been corrected. In these experiments precautions were taken to reduce the contribution of $K^+$ currents to the whole cell current by having CsCl in the pipette filling solution. The continuous recording of cell membrane potential kept the cells at their own membrane potential and reduced artifacts due to cell swelling or voltage clamping. The increase in whole cell current in 7 of 78 forskolin treated cells and the depolarization due to the reduction of the bath Cl in each of the 7 responding cells, clearly shows that the current increase in the whole cell was due to activation of a Cl conductance. The apparent homologous replacement frequency of 9% is a maximum frequency in that it assumes that each responding cell represents a single homologous replacement event. However, the possibility that in cases where multiple responding cells were detected (GS− and SD+, Table 2), each responding cell may have been derived from a single cell in which homologous replacement occurred can not be ruled out. If this was the case, the responding cells would, in effect, reflect 3 separate honmologous replacement events and would indicate a frequency of −4% (3 in 74 cells). These values show close agreement with the calculation of frequency from the densitometric analysis of homologous replacement frequency (3–7%). In any event, the degree of homologous replacement and phenotypic correction is well within the range of 6–10% that appears to be sufficient for conversion of a CF epithelial monolayer to one with normal cAMP-dependent Cl transport properties as reported in *Nat. Genetics,* 2:2 (1992).

To confirm that homologous replacement happened, PCR analysis of the DNA from nonCF primary epithelial cells was investigated. Results are shown in FIGS. 12–15.

Figure 12:
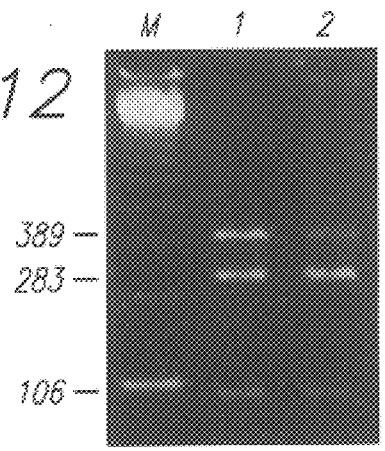
FIG. 12 illustrates restriction enzyme digestion analysis of the allele-specific amplification product generated with primers CF1B/CF8C from PCR amplification of DNA from nontransformed primary airway epithelial cells transfected with 4–88 base fragments containing the ΔF508 mutation and the XhoI restriction site.

FIG. 12 is restriction enzyme digestion analysis of the allele-specific amplification product generated with primers CF1β/CF8C. Primary nonCF airway epithelial cells were transfected with 488 base ssDNA fragments containing the ΔF508 mutation and an Xho I restriction enzyme site. PCR amplification of the DNA by primers CF1B/CF7C gave a product of 389 bp. When the amplification product was cut by Xho I, fragments of 283 and 106 bp were detected (lanes 1 and 2). DNA was isolated from cells transfected with rec A-coated (lane 1) and uncoated (lane 2) 488 base fragments. Cutting by Xho I is not 100%. This lack of complete digestion has been routinely observed in the cutting of PCR derived fragments.

FIG. 12 shows that using PCR analysis of the DNA from nonCF primary airway epithelial cells that the cells have undergone homologous replacement with a 488 nucleotide ΔF508 DNA fragment. Restriction enzyme analysis of the PCR product generated from the genomic exon 10 locus further shows that the exogenous fragment replaced the endogenous sequences.

Figure 13:
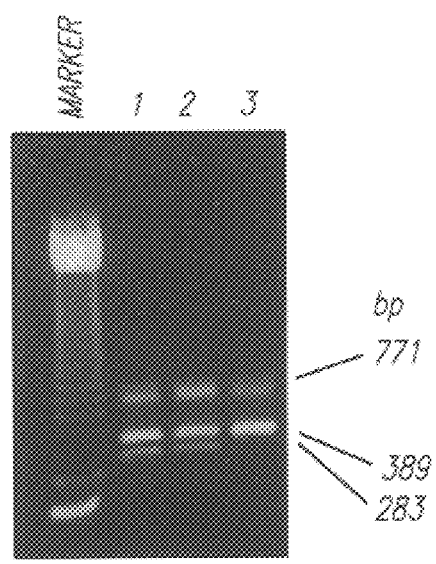
FIG. 13 shows analysis of DNA from transformed nonCF airway epithelial cells transfected with the 488 base fragments containing the ΔF508 mutation and the Xho I restriction site.

FIG. 13 is an analysis of transformed nonCF airway epithelial cells (16HBE14o-) transfected with the 488 base fragments containing the ΔF508 deletion and the Xho I restriction site. Cells were transfected with lipofectamine and then the DNA was isolated. PCR was first performed using primers CF1B/CF6. The mixed population of 771/768 bp fragments were then purified using Qiagen spin filters. Allele-specific PCR was then carried out on this mixed population with primers CF1B/CF8C to detect fragments in the population that contained the ΔF508 mutation. PCR fragments from post-transfection passage 1 (lane 1) and passage 2 (lane 2) cell DNA was digested with Xho I. Digestion of the 389 bp fragments indicated a 283 bp fragment at both passages. The second 106 bp fragment could not be visualized by ethidium bromide fluorescence. No restriction fragment was detected when control DNA (amplified with normal specific CF1B/CF7C primers) was exposed to Xho I digestion (lane 3).

FIG. 13, using analysis of DNA from a transformed nonCF airway epithelial cell line (16HBE14o-), shows that genomic exon 10 DNA was replaced with incoming ΔF508 DNA fragments.

Figure 14:
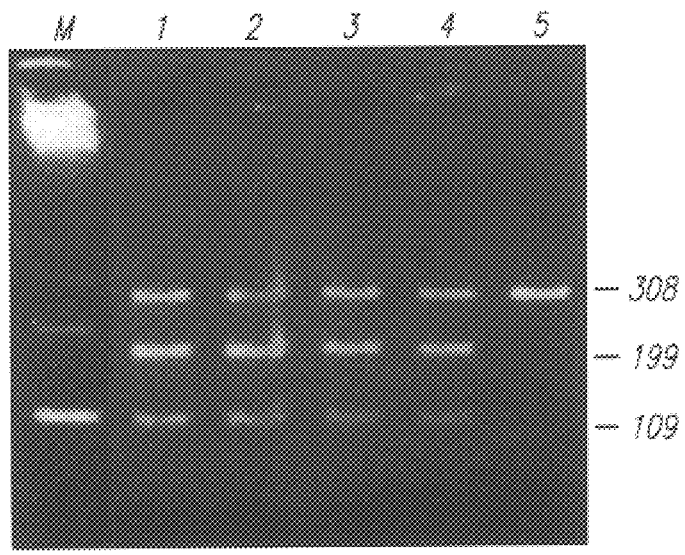
FIG. 14 shows PCR and restriction enzyme analysis of transformed CF airway epithelial cells transfected with the 491 base fragments containing wild type CFTR and the Xho I restriction site.

FIG. 14 shows PCFR and restriction enzyme analysis of transformed CF airway epithelial cells (ΣCFNPE14o-) transfected with the 491 base fragments containing wtCFTR and the Xho I restriction site. DNA from the cells was first amplified with primers CF1B/CF6 giving a mixed population of fragments (771/768 bp). These fragments were purified and then allele-specifically reamplified with primers CF1/CF7C (lanes 1–4) or with primers CF1/CF8C (lane 5). The PCR product from the second round of amplification was then digested with Xho I. Cells transfected with (lanes 1 and 3) or without (lanes 2 and 4) rec A coated DNA in gramicidin S-DNA-lipid (lanes 1 and 2) or dendrimer-DNA (lanes 3 and 4) complexes all showed cutting with Xho I resulting in 199 and 109 bp restriction fragments and a 308 bp undigested fragment (lanes 1–4) Fragments derived from control DNA did not cut when incubated with Xho I (lane 5).

Figure 15:
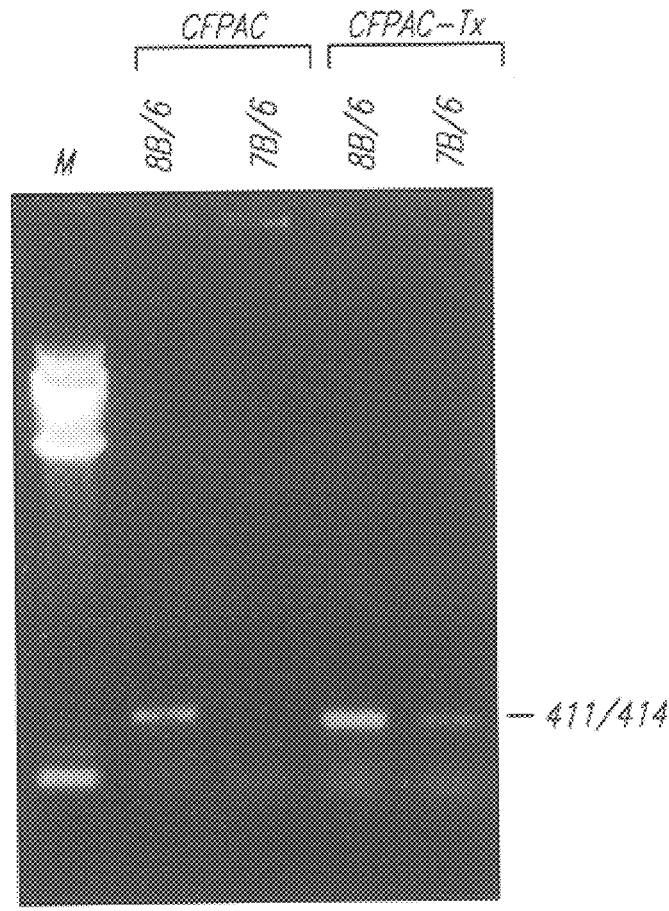
FIG. 15 is a PCR analysis of DNA from SFHR 491 base fragments transfected CFPAC cells that had been in culture for more than 6 months.

FIG. 15 is PCR analysis of DNA from SFHR (491 base fragments) transfected CFPAC cells (CFPAC-Tx) that had been in culture for more than 6 months still indicated the presence of wtCFTR sequences at the appropriate genomic locus. DNA was amplified with primers CF7B/CF6 (414 bp) and CF8B/CF6 (411 bp) for nonCF and ΔF508 sequences, respectively.

Allele-specific PCR analysis of transformed CF epithelial cells indicated that cells transfected with wt CFTR DNA fragments containing Xho I restriction enzyme site had undergone a homologous exchange at the genomic exon 10 locus (FIG. 14) and showed the presence of wtCFTR DNA after approximately 6 months of culture (FIG. 15). Allele-specific RT-PCR analysis of RNA from primary nonCF airway epithelial cells transfected with the 488 bp (ΔF) fragment also suggested that cells were expressing the mutant ΔF508 CFTR mRNA from restriction enzyme analysis of the PCR products.

In the process of development of the current invention, a 2,908-bp region of genomic DNA comprising exon 10 and flanking introns of the human cystic fibrosis transmembrane conductance regulator (CFTR) gene has been sequenced. A 30-bp sequence variation and three single base deletions were identified when comparing the new sequence seen in FIG. 30 (SEQ ID NO:1) and previously published sequence information.

Oligonucleotide primers based on previously published data and newly identified sequence were used for polymerase chain reaction (PCR) amplification. In the region of the 30-bp discrepancy, only the primer based on new sequence information was able to yield PCR products after amplification of cellular DNA or a fragment of genomic DNA contained in plasmid T6/20. This indicates that the published sequence may contain errors in the region of the 30-bp sequence variation. In addition, a 4-bp repeat sequence (TAAA)$_n$, was identified in a previously unsequenced region of intron 9. This repeat is dimorphic and exists in nine or ten copies on different chromosomes. Ten repeats, (TAAA)$_{10}$, were associated with chromosomes carrying the ΔF508 mutation found in 70% of all CF chromosomes. Nine repeats, (TAAA)$_9$, were associated with normal and/or non-ΔF508 chromosomes. This repeat might serve as an additional polymorphic marker for carrier detection, linkage analysis, or studies interested in the solution of chromosome 7.

Amplification of DNA fragments exon 10 and adjacent introns of the CFTR gene used PCR primers based on genomic DNA sequence of 831-bp in length, published in *Genomics,* 10:214 (1991). Primers sequences are shown in Table 4. Of several primers tested, primer CF2, derived from 5' end of the published DNA sequence (Table 4), was unproductive with any other downstream primers.

TABLE 4

| Primer Sequences (5'->3') | | |
|---|---|---|
| Primer | Sequence | |
| CF2(+) | ACTGTAGCTGTACTACCTTCCATC | SEQ ID NO. 17 |
| CF32(-) | GACAATTACAATACAGTGTGACAAG | SEQ ID NO. 18 |
| CF33(+) | GGGTTCATTTGATCACAATAAATGC | SEQ ID NO. 19 |
| CF34(+) | CAGCTTTTCTTAATAAAGCAATCAG | SEQ ID NO. 20 |
| CF35(+) | TGCAATTCTTTGATGCAGAGGCAA | SEQ ID NO. 21 |
| CF36(-) | AGAATGAGAGACCCACAGTACTAAA | SEQ ID NO. 22 |

TABLE 4-continued

Primer Sequences (5'->3')

| Primer | Sequence | | |
|---|---|---|---|
| CF37(-) | ATTCAGGTAATATTGTTCCCATGAG | SEQ ID NO. | 23 |
| CF38(+) | TATTGACAGTATACTCCAAATAGTG | SEQ ID NO. | 24 |
| CF39(+) | TAACCTTTCCCATTCTTCCTCCA | SEQ ID NO. | 25 |
| CF40(+) | TCTACTTTGTAGGATTTCTGTGAAG | SEQ ID NO. | 26 |
| CF41(-) | ATTCTCTGCTGGCAGATCAATGC | SEQ ID NO. | 27 |
| C16B(+) | GTTTTCCTGGATTATGCCTGGCAC | SEQ ID NO. | 28 |
| C16D(-) | GTTGGCATGCTTTGATGACGCTTC | SEQ ID NO. | 29 |
| M13F(+) | GTTTTCCCAGTCACGAC | SEQ ID NO. | 30 |
| M13R(-) | CAGGAAACAGCTATGAC | SEQ ID NO. | 31 |

Primers C16B and C16D have been previously reported in *Science*, 245:1073 (1989) and are also indicated in Table 1. Primers M13F and M134 are derived from the bacterial lacZ sequence. To generate a single stranded template for the sequencing reaction, either M13F(+) or M13R(-) primer was 5' end labeled with biotin and used in combination with non-biotin labeled M13F(+) or M13R(-) primer, accordingly, in the PCR. Primers were synthesized and redissolved in H$_2$O without further purification. (+)=sense primers; (-)=antisense primers.

To elucidate the underlying questions about potential sequence discrepancies, plasmid T6/20 which contains the exon 10 and intron regions was sequenced. The entire sequence of the ECO RI insert from T6/20 was determined using a fluorescent automated DNA sequencer. To ensure the accuracy of the nucleotide sequence, both strands of the insert were sequenced using the primers listed in Table 4. The relative position of each primer is indicated in FIG. 16.

FIG. 16 is a schematic diagram of primer locations (not to scale) for PCR amplification and sequencing reaction. Vertical lines represent the region of published DNA sequence (not to scale).

The overlapping sequence alignments were analyzed using the Gene Works software (Inteligenetics, Inc., Mountain View, Calif.). Sequence analysis seen in Sequence ID No.: 1 indicated that the CFTR Eco RI insert in plasmid T6/20 was 2908 bp in size.

Figure 17:
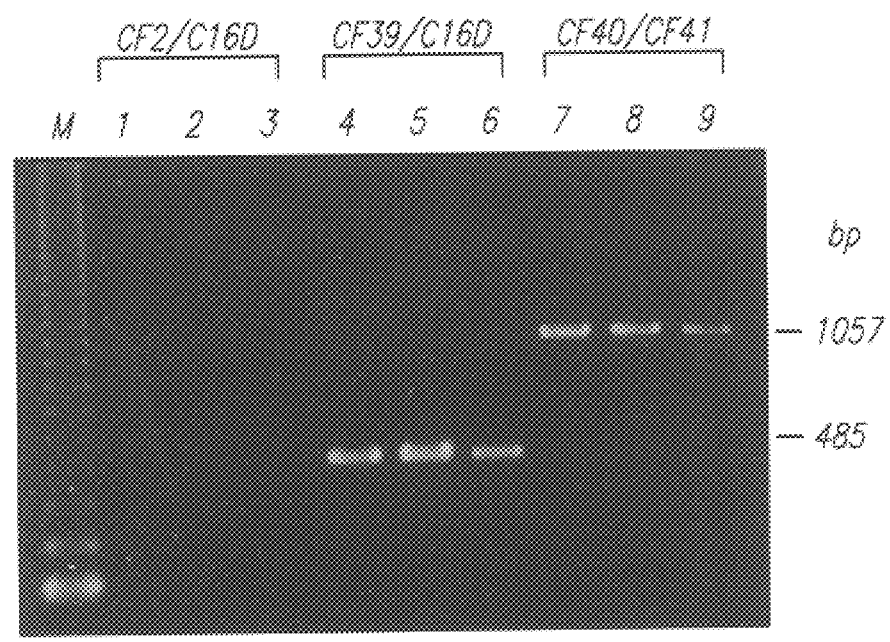
FIG. 17 is a PCR amplification used for verification of the new sequence.

A 30-bp nucleotide (nt) sequence discrepancy (nt 757–786) was revealed at 5' end of the published sequence in *Genomics*, 10:214 (1991). This result could account for the unsuccessful PCR associated with primer CF2, since the primer sequence was based on this 30-bp region as seen in FIG. 17. In addition to the 30-bp discrepancy, three single nt deletions were identified at the nt 818, 1548, and 1578, respectively when the published sequence was compared to the sequence information generated in this study. The single nt deletions probably resulted from the base compression commonly found as a consequence of manual sequencing.

SEQ ID. No. 1 is nucleotide sequence spanning exon 10 and adjacent intron regions of the human CFTR gene. The plasmid T6/20 (American Type Cell Culture) contains the exon 10 and flanking intron sequences as an Eco RI insert.

The entire sequence of the 2908 bp was determined using Prism DyeDeoxy Terminator Cycle Sequencing Kit (Perking-Elmer). The plasmid T6/20 DNA was prepared by the standard cesium chloride centrifugation isolation and purification.

Sequencing templates were either double stranded plasmid or single stranded plasmid DNA purified by streptavidin coated Dynalbeads for the biotin-labeled PCR products according to the manufacturer's recommendation (Dynal, Oslo, Norway). Sequencing primers are listed in Table 4, and the relative positions of each sequencing primer is shown in FIG. 16. The dye labeled sequence reactions were purified by passage through Centri-sep columns (Princeton Separations, Adelphia, N.J.), and analyzed by electrophoresis using Applied Biosystem Model 373A automated DNA sequencer on 6% polyacrylamide denaturing gels. The capital letters are the sequence data generated from this study. Lower case letters and dots represent the published data. The $(TAAA)_n$ repeat is underlined from nucleotide nt 155–190. The 30-bp sequence discrepancy is indicated by underlined lower case letters (nt 757–786) at the 5- end of the published data. Single nt deletions (nt 818, 1548, 1578, respectively) are indicated by dashes. The consensus RNA splice donor (AG) and acceptor (GT) sites surrounding the exon 10 (nt 1065–1256) are underlined.

FIG. 17 is PCR analysis of DNA fragments generated from the CFTR gene encompassing 2908 bp of exon 10 and adjacent introns. Human genomic DNA was prepared using standard protocols. ΣCFTE29o- is a human trachea epithelial cell line containing the homozygous CFTR ΔF508 mutation from a CF patient.

Verification of the sequence seen in FIG. 17 was carried out by PCR amplification with primers 1 based on the published sequence (CF2/C16D, lanes 1–3) compared to those based on our corrected sequence reported here (CF39/C16D, lanes 4–6), and) based on the previously unknown sequence now reported here (CF40/CF41, lanes 7–9).

PCR was carried out using 100 ng of cellular DNA or 1 ng of plasmid DNA. After initial denaturation at 94° C. for 5 minutes, reaction solutions were amplified for 30 cycles at 94° C./30 s, 60° C./30 s, and 72° C./90 s with a final extension of 5 minutes at 72° C. Negative controls without addition of DNA templates were included in parallel during PCR experiments to ensure there was no exogenous contamination. PCR products were analyzed on 1% agarose gel and visualized under the UV light. PCR primers used in each sample are indicated. The primer sequences are provided in Table 4. Lanes 1, 4, 7, T6/20 plasmid DNA; lanes 2, 5, 8, human lymphocyte DNA; lanes 3, 7, 9 ΣCFTE29o- DNA. M, a123 bp molecular weight ladder. The expected PCR fragment sizes in bp are indicated on the right.

DNA samples from the T6/20 plasmid (lanes 1, 4, and 7), nonCF lymphocytes (lanes 2, 5, and 8), and CF airway epithelial cells, ΣCFTE29o- (lanes 3, 6, and). No PCR products were detected when one primer based on the previously published sequence was used (lanes 1–3). Primers based on sequence data reported here were able to show PCR products from all DNA samples (lanes 4–9).

An expected 485-bp fragment was detected using primer CF39 and C16D in DNA samples isolated from non-CF human lymphocytes, ΣCFTE29o-, a trachea epithelia cell line derived from a CF patient homozygous for the ΔF508 mutation and from the plasmid T6/20 seen in FIG. 17. Similarly, PCR amplification with primers CF40/CF41, localized outside previously published sequence, was able to generate the expected 1057-bp fragment from the three DNA samples indicated above as seen in FIG. 17.

Upon inspection of the intron regions flanking exon 10, a 4-bp tandem sequence repeat $(TAAA)_n$ was identified in intron 9 from nt 155–190 (908-bp away from exon 10). Single sequence repeats (or microsatellite units) often show a high degree polymorphism useful in genotyping, linkage analysis, and screening for disease carriers. Since the CFTR is a large gene consisting of 27 exons dispersed along 250 kb of genomic DNA, intragenic polymorphisms were expected. Several polymorphic single sequence repeats in the CFTR gene have already been described in Genomics, 10:214 (1991). The most common single sequence repeats are dinucleotides, such as $(CA/TG)_n$ and $(TA)_n$. The (CA/TG) and TA dinucleotide repeats in intron 17b have been previously reported to be highly polymorphic for carrier detection and prenatal diagnosis of CF (Hum. Gent., 88:356 (1992). In addition, a 4-bp (GATT) tandem repeat in the flanking intron of exon 6 was described in Am. J. Hum. Genet., 48:223 (1991). The GATT-repeat element was found to exist in dimorphic forms of either 6 or 7 units.

The TAAA repeat has not previously been shown to be associated with CFTR. The 4-bp $(TAAA)_n$ identified in intron 9 in this study represents a microsatellite unit. This repeat was found to exist in nine or ten copies on different chromosomes by PCR screening using the primers flanking the repeat. Ten repeats of the $(TAAA)_{10}$ were linked to the ΔF508 chromosome (n=7). While nine repeats of the $(TAAA)_9$ were only associated with normal/non-ΔF508 chromosomes (n=9). While the functional role of the repeat elements remains to be defined, the $(TAAA)_n$ repeat is one of the most common repeats in the primate genome and is often a polymorphism associated with Alu repetitive elements. This repeat could therefore serve as an additional polymorphic genetic marker for carrier detection, linkage analysis, could assist in determining the evolution of the ΔF508 mutation, or could facilitate genotype/phenotype correlation analysis.

Comparison between human and mouse DNA sequences revealed that the two species share about 84% homology in the 192-bp exon 10 sequence. However, no sequence homologies were found between two species in the flanking intron regions.

Results of the studies outlined above confirm that by using the method of the invention, the dysfunction caused by CF gene mutation is successfully corrected.

Similarly, the other diseases were corrected using the current method. The second genetic disease to treat by SFHR is sickle cell anemia Classical sickle cell (SC) anemia is a devastating disease that afflicts as many as 1 in 64 backs in Africa and from 1 in 200 to 1 in 400 blacks in the United States. The disease is caused by an A to T transversion in the sixth codon of the human beta-globin gene resulting in a Glu to Val substitution in the protein. Phenotypically there is a polymerization of the hemoglobin that results in a myriad of pathologies which ultimately lead to the death of the individual. Numerous therapies have led to the amelioration of the photogenic effects attributed to the mutation, however, very little has been done in the way of gene therapy.

Primers used for generation of short homologous fragments and for analysis of homologous exchange are shown in Table 5.

TABLE 5

Sickle Cell Primers

| PRIMER | SEQUENCE | |
|---|---|---|
| SC1 (+) | 5'-TAGCAATTTGTACTGATGGTATG-3' | SEQ ID NO. 32 |
| SC2 (−) | 5'-TATACACAATTTAAGGCATTAG-3" | SEQ ID NO. 33 |
| SC3 (+) | 5'-CCCTGTGGAGCCACACCCTAGGGT-3' | SEQ ID NO. 34 |
| SC4 (−) | 5'-AACGATCCTGAGACTTCCACACT-3' | SEQ ID NO. 35 |
| SC5 (+) | 5'-ACATTTGCTTCTGACACAACTGTG-3' | SEQ ID NO. 36 |
| SC6 (−) | 5'-AGGGTTGCCCATAACAGCATCAG-3' | SEQ ID NO. 37 |
| SC-BA (−) | 5'-CTTCTCCTCAGGAGT-3' | SEQ ID NO. 38 |
| SC-BS (−) | 5'-CTTCTCCACAGGAGT-3' | SEQ ID NO. 39 |

Primers SC3 and SC4 are for the generation of DNA fragments to replace genomic β-globin sequences at the sickle cell (SS) locus (codon 6). Primers SC1 and SC2 are for analysis of homologous exchange at the SS locus in genomic DNA. Primers SC5 and SC6 will be used to assay mRNA expression of the DNA that has undergone homologous replacement. Primers SC-BA and SC-BS are allele-specific and differentiate between wild-type (SC-BA) and sickle (SC-BS) β-globin sequences. The (+) and (−) designate sense and antisense sequences, respectively.

Figure 18:
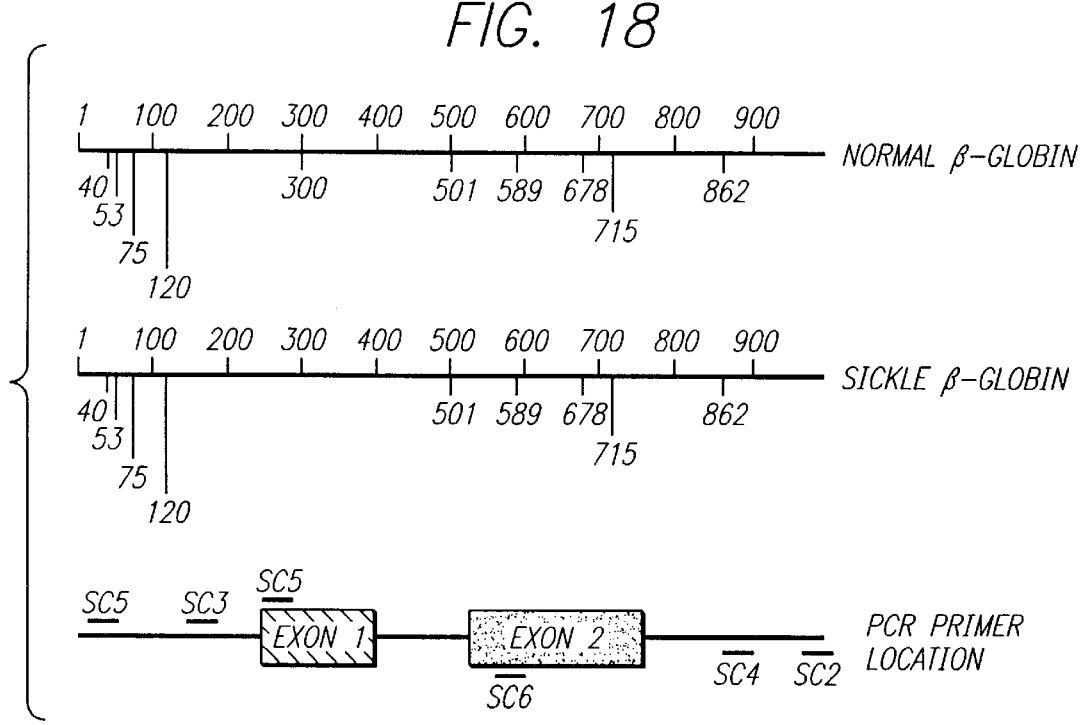
FIG. 18 depicts the Dde I restriction enzyme cleave site in the 990 bp normal and sickle human β-globin SC1/SC2 PCR amplification product.
Figure 19:
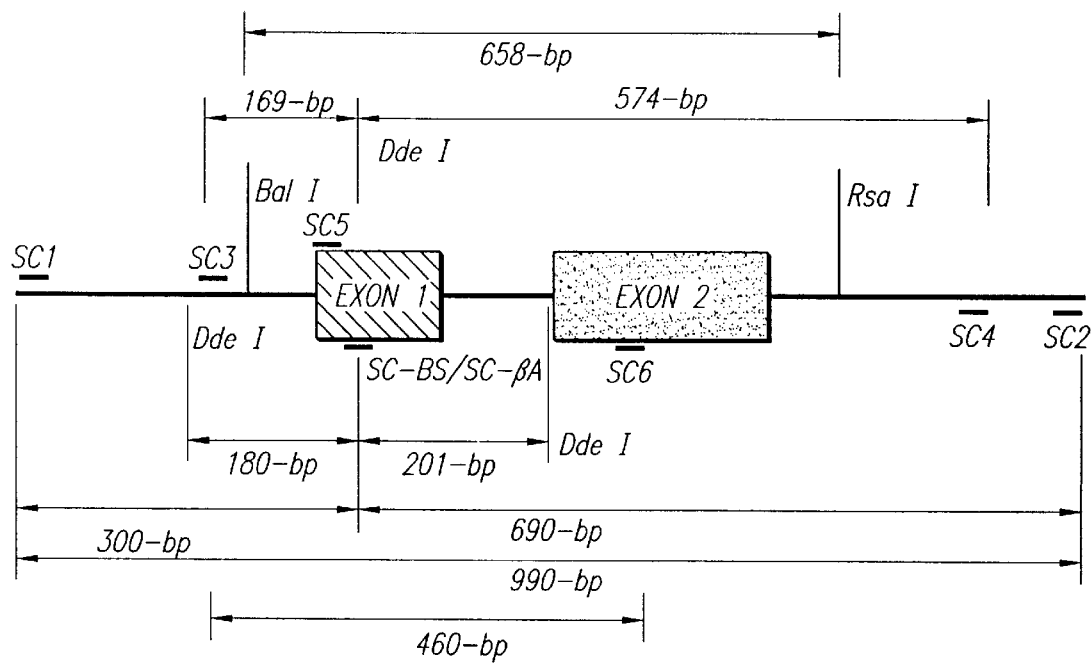
FIG. 19 is a schematic representation of the region in the human β-globin gene to undergo homologous replacement.

FIGS. 18–20 show restriction enzyme cleavage sites and the region in the human β-globin gene to undergo homologous replacement.

FIG. 18 depicts normal and sickle human β-globin SC1/SC2 fragment having 990 bp and shows the Dde I restriction enzyme cleavage sites in the 990 bp SC1/SC2 PCR amplification product. In comparing the restriction sites between the normal wild-type (wt) β-globin (SA) to the sickle β-globin (SS), the Dde I site at bp 300 is lost. The ssDNA should therefore yield a new restriction fragment of 381-bp.

FIG. 19 is a schematic representation of the region in the human β-globin gene undergoing homologous replacement. The Bal I and Rsa I restriction enzyme cleavage sites define that boundaries of one homologous region (657 bp) generated by restriction enzyme digestion. Primers SC3 and SC4 represent the boundaries of a second homologous fragment (743-bp) generated by PCR amplification. Primers SC1 and SC2 define a 990-bp fragment. The SC1.SC2 primers are outside the regions of homology. Digestion with Dde I of normal β-globin will yield multiple fragments as seen in FIG. 18. Dde I digestion of SS DNA yields a 381-bp fragment, while SA DNA has 180- and 201-bp fragments. Primers SC3/SC6 amplify genomic DNA and yield a fragment of 460-bp with 2 Dde I sites. One site with the sickle cell mutation disappears. The presence of β-$^S$ globin or normal globin is further determined by allele specific amplification with SC-β$^S$ and SC-β$^A$, respectively.

FIG. 20 shows PCR analysis of human β-globin DNA. FIG. 20 is a schematic representation of the RT-PCR and Dde I restriction digestion analysis of β-globin mRNA-derived cDNA. There is only one Dde I restriction site in the cDNA and its elimination will lead to a 227-bp fragment rather than the 67- and 160-bp fragments found in sickle cell anemia cells.

FIG. 20 confirms the conversion of normal, $B^A$-globin to the sickle cell, $B^S$-globin in cultured mouse erythroleukemia cells carrying human chromosome 11, and the correction of the SC mutation in a transgenic SC mouse model. The verification of success is carried out using PCR amplification of DNA and mRNA derived cDNA with allele-specific oligonucleotides (ASO) and by restriction fragment length polymorphic (RFLP) analysis. In addition, in hematopoietic cells expressing hemoglobin, the protein is analyzed for the presence of normal hemoglobin with allele-specific antibodies. The development of a transgenic mouse model that contains and expresses human sickle cell anemia cDNA and mRNA, respectively, made it possible to assess if the mutation can be corrected in vivo. The mouse can also be assayed for the presence of the normal human hemoglobin. These studies are intended to ultimately lead to development of a small fragment homologous replacement (SFHR) strategy for the treatment of sickle cell anemia in humans. The strategies and analyses in this in vitro system will be directly transferable to in vivo studies.

Another disease which can be treated by homologous recombination using small fragments in xeroderma pigmentosum, a disease of skin. Xeroderma pigmentosum is a rare, disfiguring syndrome inherited as an autosomal recessive trait.

FIG. 21 shows the Xeroderma pigmentosum group G (XP G) gene containing 573-bp of known genomic sequence restriction map surrounding the exon that contains the mutation defined as one cause of the XP G phenotype, the exon is 245-bp and contains a deletion of an A in a run of AAA at bp 19–21 of the exon. A unique Kpn I restriction site was placed into the therapeutic fragment by introducing silent mutations at bp 97 (C>T) and 100 (T>C) into the exon.

Table 6 lists DNA sequences primers used for generation of short homologous fragments.

TABLE 6

Xeroderma Pigmentosum (XP) Group G PCR Primers

| PRIMERS | SEQUENCE | |
|---|---|---|
| XP1(+) | 5'-AGCATTTTTCAGGTTCCTCCAG-3' | SEQ ID NO. 40 |
| XP2(-) | 5'-AACCTACTTAACCTGGCTTCCT-3' | SEQ ID NO. 41 |
| XP3(+) | 5'-GGCTTGTTTTGAAGTTACAGGC-3' | SEQ ID NO. 42 |
| XP4(-) | 5'-AAGCCATCAGCAACCACAAGA-3' | SEQ ID NO. 43 |
| Allele-Specific primers | | |
| XP6AS(-) (N) | 5'-CCTCATCACTAATCACACTTTG-3' | SEQ ID NO. 44 |
| XP6B(-) (XP) | 5'-TCCTCATCACTAATCACACTTG-3' | SEQ ID NO. 45 |
| XP7A(+) (N) | 5'-GAAGTTTCATTGAAGTGCAAAG-3' | SEQ ID NO. 46 |

TABLE 6-continued

Xeroderma Pigmentosum (XP) Group G PCR Primers

| | SEQUENCE | |
|---|---|---|
| XP7B(+) (ZXP) | 5'-GGAAGTTTCATTGAAGTGCAAG-3' | SEQ ID NO. 47 |

Primers for the generation of therapeutic DNA fragments 397-bp (XP1/XP2) and the fragment for PCR analysis of SFHR 572-bp (XP3/XP4). Allele-specific analysis of the wild-type (N) sequences of the XP group G gene is detected by amplification with either XP3/XP6A (237-bp) and XP7A/XP4 (374-bp). The XP G mutation (AAA>AA) was assayed by amplification with XP3/XP6B (237-bp) and XP7B/XP4 (374-bp). Sense=(+), antisense=(−).

Primers XP1 (bp 104, 22-bp) and XP2 (bp 479, 22-bp) are used to generate a 397-bp therapeutic fragment. Primers XP3 (bp2, 22-bp) and XP4 (bp 551, 22-bp) are used for PCR analysis to generate a 572-bp fragment that comprises the homologous region and flanking sequences. Allele-specific primers XP6A and XP7A detect normal (N) sequences and XP6B and XP7B detect the XP-G mutation. XP6A and XP6B are used in conjunction with XP3 to generate a fragment of 237-bp, while XP7A and XP7B are used with XP4 to give a product of 374-bp. Because the 374-bp fragment contains a Kpn I cut site, cleavage results in 97-bp and 277-bp restriction fragments.

FIG. 21A depicts the restriction enzyme cleavage sites at 153 (Bin 1 153), 249 (Eco R1 249) and 295 (Kpn I) bp amplification product. FIG. 21B is a schematic representation of the region of gene XP-G 721–1300 undergoing homologous replacement.

The homologous recombination for correction of sickle cell anemia mutation, for xeroderma pigmentosum is performed in the same manner as the one described for cystic fibrosis. In the same manner, all other genetic diseases are corrected.

V. In vivo Method

Another embodiment of this invention is an in vivo method of altering a DNA fragment in a subject's target cells. Typically, this is achieved by direct administration of the exogenous small DNA fragments bearing the normal DNA sequence. The clinical protocol for such in vivo treatment is described in Example 19.

In vivo method is intended for correction of genetic defects in humans and animals.

VI. Ex Vivo Method

Also embodied in this invention is an ex vivo which is also an in vitro method for genetically altering a DNA sequence in a subject's target cells. The ex vivo method involves obtaining cells which contain mutated DNA fragment from a mammalian subject as well as obtaining a small DNA fragment comprising a normal wt DNA sequence.

The normal DNA fragment is delivered into the cells under conditions effective for homologous replacement to occur. The resulting genetically altered cells can then be delivered to the subject in need of gene correction. This ex vivo alteration of cells and their transplantation into an afflicted individual comprises another mode of delivery of the exonous DNA fragment, as opposed to direct introduction of the fragments in vivo.

The foregoing ex vivo method may be used to remove the subject's own cells, alter the DNA of those cells and subsequently return the altered cells to the subject. The method may also be used to alter related transformed cells from a subject or from established cell lines. The established cells lines are modified to suppress their malignant characteristics, and the like, and then the altered cells are placed into the subject. By performing homologous replacement outside of the subject's body, this method has the advantage of permitting different transfection methods and conditions that would not be feasible or easy to implement with an in vivo method.

In one aspect, the method is applied to altering stem cells which have the potential to repopulate, such as haematopoietic stem cells. However, other somatic cells may be altered by homologous replacement if that particular cell type has the potential to repopulate in the subject. Other cell types may also be altered if upon homologous replacement, their accumulated cell function is sufficient to overcome the disease condition.

To practice the ex vivo method for gene therapy of a disease associated with a defective DNA sequence, the target cells may be obtained from a mammalian subject, including a human, afflicted with the disease. Cells may be obtained as discussed above, either from a bodily fluid, specific tissues carrying somatic cells, and the like. An artisan would know what specific cells are desired and how to extract them from a subject.

In the case of ex vivo methods, microinjection is especially preferred as a transfection techniques for its high rate of homologous replacement. The small number of target cells required by this technology may overcome its labor intensive nature.

The isolation of embryo and germ cells as well as the different manipulations involved in the application of the transfection methods are known in the art and exemplified herein.

VIII. Non-nuclear DNA

The foregoing method may also be used to alter DNA sequences in non-nuclear DNA whether present in the cell as mitochondrial DNA, viruses, bacteria, plasmids, or hybrid vectors. In addition, this method also provides a means for altering DNA sequences which do not result in the expression of altered gene products. These sequences include defective regulatory genes, intron sequences and the substitution of redundant codon sequences, among others.

Other alterations may be undertaken by practicing the above method, such as the insertion of sequences other than normal wild type DNA which permit quasi-normal cell function or any other desired cellular function.

IX. Cell Lines

In another embodiment, the present method may be applied to immortalized mammalian cell lines to manufacture cell lines carrying a defect associated with a specific disease. The thus constructed cell line may be utilized for testing drugs intended for use against such disease, or for other purposes. Construction of such cell lines is illustrated in Example 1.

Also disclosed herein is the creation of a novel immortalized human cell line, ΣCFTE29o-, that originated from cells of a CF human patient with two ΔF508 alleles. The ΣCFTE29o- cell line was transformed in vitro to become immortalized. This cell line is thus homozygous for the ΔF508 mutation, the most common genetic defect found in cystic fibrosis patients. This cell line has been deposited with the ATCC in Rockville, Md., and has been given an Accession No 11151.

The establishment of the above immortalized cell line carrying a genetic defect physiologically resembling the human error allows generation of the technology necessary to correct genetic defects associated with different diseases.

The mammalian cell whose DNA sequence is to be altered may be obtained from immortalized or non-transformed cells of a specific mammalian strain or species, including single species mammalian cells including human cells, among others. The latter may by utilized for the in vitro experimental manipulation of cells to produce variant or hybrid cells having a genetic defect associated with a certain disease. In addition, if the cells are embryonic or germ cells, they may be utilized for the production of transgenic animals. In addition, the cells may be extracted from an animal or human, by for example a spinal tap, a venous or arterial injection, from a specialized tissue, and the like. When precursor cells are utilized, the modifications incorporated into these cells will eventually produce cells of a certain specificity. This is the case of many blood cells, where stem cells are being modified.

In an additional embodiment of the above method, the mammalian cell comprises immortal and non-transformed cells, and amongst them germ line cells, embryo cells, and the like, or somatic cells such as stem cells and the like. Preferred cells are human cells, and among the human cells are non-transformed cells.

Genetic alterations in accordance with this invention may be attained with transformed cell lines and non-transformed cells, and among them with both germ line cells and somatic cells in vivo and in vitro.

This invention further includes a mammalian cell line obtained by the above method, wherein the altering DNA sequence contains a faulty sequence associated with one of the diseases listed above, for example, cystic fibrosis. The cell may be made to contain two cystic fibrosis alleles and thus be homozygous for cystic fibrosis.

The production by the method of this invention of cell lines carrying defective genes associated with CF and other diseases is also contemplated herein. Thus, mammalian, for example, human cell lines may be obtained by the present method carrying genetic defects associated with specific diseases as described above. Particularly preferred cells are those having physiological and/or biochemical characteristics associated with CF, sickle cell anemia, Fanconi's anemia, retinitis pigmentosa, Xeroderma pigmentosa, ataxia telangiectasia, Bloom's syndrome, retinoblastoma, Duchenne's muscular dystrophy, and Tay-Sachs disease. These alterations are introduced in the chromatin of the cell and are thus under the regulatory control of the cellular promoter/enhancer corresponding to the gene effecting a correction of the genetic defect.

X. Transgenic Animals

In another embodiment, the present technology is applied to the ex vivo production of transgenic animals as further described below.

A transgenic mouse (or a larger animal) is made with the mutant β-gal plasmid to test and optimize the efficiency of SFHR in vivo. The same principles are used for the animal model system as those described above for the in vitro cell culture system. The animal is made by injecting the mutant plasmid into fertilized oocytes or embryonic stem cells. Progeny animals are assessed by genomic Southern hybridization and by PCR analysis. The region of genome containing the integrated plasmid is sequenced to insure that no new mutations have been introduced into the β-gal gene.

The method for production of transgenic animals bearing certain genetic trait comprises homologous replacement using short homologous fragments of the DNA sequence desired to be introduced the mammalian cells. The desired DNA sequence is obtained using the method of the invention. First the primers are produced with sequences homologous to the region containing gene sequences desired to be changed. Large amounts of DNA fragments are then produced. These fragments are delivered into a germ or embryo cell of a mammal, as described before. When the homologous replacement is achieved and confirmed according to the invention, gestation is allowed to proceed to term to produce a transgenic non-human mammal conferring on the transgenic animal desired genetic traits.

The method for producing a transgenic animal provided herein permits the insertion of a desired gene or portions of a gene having a desired characteristic from other species or other strains of the same species. In one aspect of this method, different DNA fragments targeted to more than one gene may simultaneously be incorporated into the cellular DNA by homologous replacement. The present method thus enables the insertion of multiple genes and, therefore, the transfer of novel biological or biochemical functions to a new species.

Development of a mouse model for cystic fibrosis has provided important information regarding the pathology of CF. However, the models that have been developed contain a disruption of the CFTR gene and not a naturally occurring CFTR mutation. The SFHR technique has a marked advantage over the classical approach to homologous gene targeting in that it is straight-forward method to introduce specific mutations into endogenous genes rather than inactivate the genes by disruption of exons with selectable marker genes. Thus, using the method of the invention, it will be possible to generate animal models with naturally occurring mutations. To advance the understanding of the role that naturally occurring CF mutations play in CF pathology, the SFHR method was used to introduce the ΔF508 mutation into mouse embryonic stem (ES) cells.

Mouse ES cells were transfected with fragments of DNA homologous to the mouse CFTR (mCFTR). The fragments were generated by PCR amplification of a plasmid containing the exon 10 region of the mouse CFTR with a plasmid containing the exon 10 region of the mouse CFTR with a pathogenic CF mutation and a silent mutation that creates a novel restriction enzyme site. Primers used for homologous replacement in mouse are seen in Table 7.

TABLE 7

Mouse CFTR Primers for Homologous Recombination

| | DNA SEQUENCE | |
|---|---|---|
| PRIMERS | | |
| mCF1 (S) | 5'-GCCTAGAAAAGTCCCTGTATCATG-3' | SEQ ID NO. 48 |
| mCF2 (A) | 5'-GACACAAGTAGCTAACACAATCAGC-3' | SEQ ID NO. 49 |
| mCF3 (A) | 5'-CCCTTTTCAAGGTGAGTAGTCAAG-3' | SEQ ID NO. 50 |
| mCF4 (S) | 5'-CACTCATGTAGTTAGAGCATAGGG-3' | SEQ ID NO. 51 |
| mCF-508 (A) | 5'-GTACTCATCATAGGAAACACCGAT-3 | SEQ ID NO. 52 |
| mCF-N (A) | 5'-ACTCATCATAGGAAACACCAAA-3' | SEQ ID |

TABLE 7-continued

Mouse CFTR Primers for Homologous Recombination

| | DNA SEQUENCE | |
|---|---|---|
| | | NO. 53 |
| mCF6 (A) | 5'-GAATTCATACAGACTTTTGGTTTGT-3' | SEQ ID NO. 54 |
| mCF7 (A) | 5'-CTGTCTGCTTCCTGACTATGGATA-3' | SEQ ID NO. 55 |
| mCF15 (A) | 5'-GGGGTCCTTGACATGTTTACAT-3' | SEQ ID NO. 56 |
| PRIMERS (cDNA) | | |
| mCF9 (S) | 5'-GGGAATTACTGCAGAAAGCACAAC-3' | SEQ ID NO. 57 |
| mCF10 (A) | 5'-TAAAGAAATCCTTGCACGCTGACC-3' | SEQ ID NO. 58 |

Table 7 lists sequences of mouse CFTR PCR primers and corresponding sequencing seen in FIG. 18. A=antisense (3'), S=sense (5'). Primers mCF-508 anf mCF-N are allele-specific and are specific for ΔF508 CFTR and wild-type CFTR, respectively. Primers mCF9 and mCF10 are for the detection of CFTR mRNA via RT-PCR.

The strategies for the generations and analysis of the mouse CFTR is indicated in FIGS. 22 and 23. The primers used for the generation of the various DNA fragments that were used in the transfections and those used in the PCR analysis of the ES cell genomic DNA in the region of CFTR exon 10 are indicated in Table 6. After transfection by electroporation with double stranded DNA (dsDNA) fragments, the cellular DNA was analyzed by PCR amplification.

FIG. 22 is a schematic representation of the PCR analysis of genomic DNA derived from transfected embryonic stem (ES) cells. Cells were initially transfected by electroporation with a 432 bp fragment containing the ΔF508 mutation and a unique Kpn I restriction site that had been introduced by site directed mutagenesis as a silent mutation. The fragment was generated by PCR amplification of plasmid DNA containing homologous mouse CFTR with the ΔF508 mutation and the Kpn I restriction site. The primers used were mCF1/mCF3. Homologous replacement was determined by allele-specific amplification with primers mCF4/mCF508 or nonallele-specific amplification with primers mCF4/mCF2. After digestion with Kpn I, allele specific amplification products should yield fragments that are 42 and 440 bp, while the nonallele-specific amplification products should yield 127 (ΔF)/130 (N) and 440 bp restriction fragments.

FIG. 23 is a schematic representation of the PCR analysis of genomic DNA derived from transfected embryonic stem cells.

Subsequent transfection to those seen in FIG. 22 were carried out with fragments that were 1081 or 783 bp. Analyses were carried out such that at least one primer was outside the region of homology defined by the incoming transfected fragment.

Initial results indicated that within a pooled population of transfected ES cells there was a subpopulation that contained exogenously introduced mutant DNA at the appropriate genomic locus. Results are seen in FIG. 24.

Figure 24:
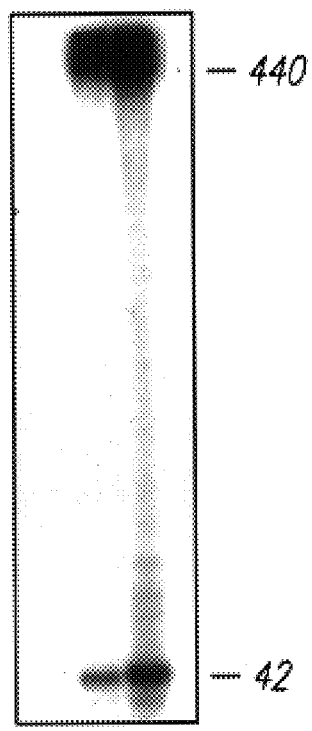
FIG. 24 shows an autoradiogram of PCR products from mouse ES cell DNA transfected with 432 bp fragments digested with Kpn I.

FIG. 24 is an autoradiographic analysis of PCR products that were digested with Kpn I. PCR amplification of DNA from pooled ES clones was first carried out with primers mCF4/mCF2 and then with primers mCF4/mCF508. Kpn I digestion was carried out on the second round amplification products. After allele specific amplification and Kpn I digestion of the second round products, the expected 440 bp and the diagnostic 42 bp band were observed as indicated.

Isolation of a clone 67 of ES cells followed by PCR analysis of clone 67 indicated that this clone contained genomic DNA with a unique restriction enzyme site (Kpn I) and the ΔF508 mutation originally found in the transfected DNA fragment.

Figure 25:
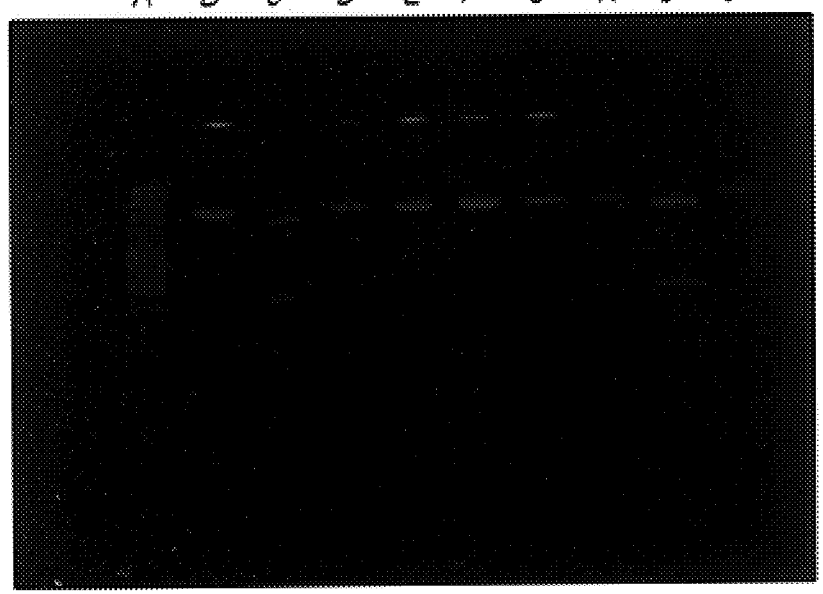
FIG. 25 is a photograph of analysis of individual clones following transfection with the 432 bp fragments.

FIG. 25 is an analysis of individual clones, following transfection with the 432 bp fragments, suggested that an ES cell clone that had the ΔF508 DNA was obtained. The size of the restriction fragments were comparable to those seen following Kpn I digestion of a PCR fragment generated from plasmid DNA that contained the mouse CFTR DNA with a ΔF508 mutation and a unique Kpn I restriction site (lane i). No digestion was observed using normal ES cell DNA (lane j). Subsequent analysis of ES cell DNA following transfection with 783 bp and 1081 bp fragments indicated that the larger dsCFTR DNA fragments result in higher efficiency of homologous replacement. The analysis of ~200 pools of 10 clones each indicated that there were at least 3 clones that contained ΔF508 CFTR following amplification with mCF4/mcF508. This transfection used 783 bp fragments.

Figure 26:
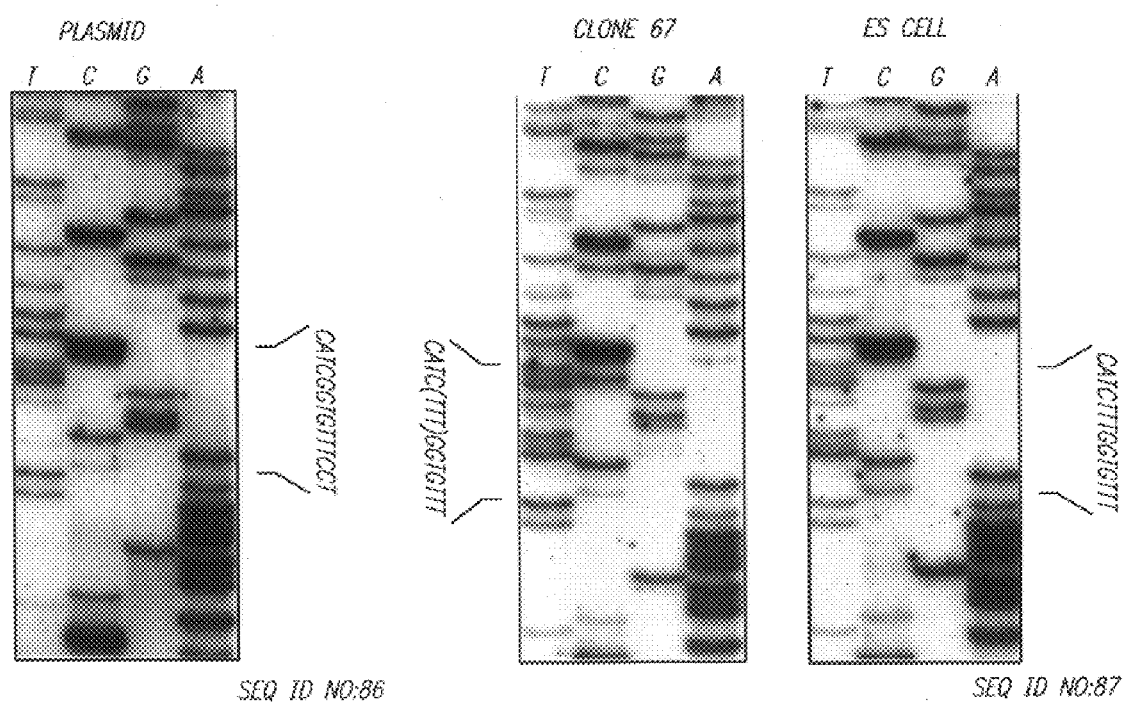
FIG. 26 is a sequence analysis of a PCR product from a mCF4/mCF2 amplification from clone 67 (SEQ ID NOS:86–87).

Sequence analysis of the PCR product further confirmed that the product contained both the ΔF508 mutation and the restriction enzyme site, seen in FIG. 26.

FIG. 26 is a sequence analysis of a PCR product from a mCF4/mCF2 amplification from clone 67. The results of these studies indicate that there is a significant population of DNA amplification products that were derived from the appropriate genomic locus and contain a ΔF508 mutation. When compared to endogenous normal mouse CFTR sequences, there is a 3 bp (TTT) deletion that is observed in both the plasmid derived DNA as well as in the PCR product derived from the transfected ES cells (clone 67). There was also a significant level of normal sequence that in this clonal isolate, suggesting that the clone was not a pure population of cells, and/or that there was a differential amplification of the mutant and wild-type sequences, and/or that this difference is an artifact of the sequencing procedure. Equal amounts of mutant and wild-type CFTR DNA were expected since the transfection effectively creates a heterozygote situation. The Kpn I restriction site was also indicated in sequencing gel. Subsequent analysis of additional transfection indicated that efficiency of homologous replacement could be as high as $10^{-2}$.

XII. An Assay System for Assessment of the Frequency of Homologous Replacement

To detect the frequency of homologous replacement according to the method of the invention, an assay system was developed. The new assay utilizes either the neomycin resistance (neo$^r$) selectable marker gene or reporter gene systems. The β-galactosidase (β-gal) gene was used as a reporter gene. The gene for green fluorescent protein (GFP) was used as a reporter gene. These selectable/reporter gene systems have been mutated at specific points within their coding region and the function of the gene was reconstituted following small fragment homologous replacement.

A description of the primers used to generate therapeutic fragments and to analyze small fragments homologous replacement in these systems is included in Table 8.

TABLE 8

Primers for Selection or Reporter Genes

| PRIMERS | SEQUENCE | |
|---|---|---|
| Neo (pCDNA3) | | |
| NY1 (+) | 5'-GAACAAGATGGATTGCACGCAG-3' | SEQ ID NO. 59 |
| NY2 (-) | 5'-CGCCAAGCTCTTCAGCAATATC-3' | SEQ ID NO. 60 |
| NY3 (+) | 5'-ATTCGGCTATGACTGGGCACAA-3' | SEQ ID NO. 61 |
| NY4 (-) | 5'-GCCACAGTCGATGAATCCAGAA-3' | SEQ ID NO. 62 |
| GFP (pGFP-N1) | | |
| GF1 (+) | 5'-TTTCTGTCAGTGGAGAGGGT-3' | SEQ ID NO. 63 |
| GF2 (-) | 5'-TGGTTGTCTGGTAAAAGGAC-3' | SEQ ID NO. 64 |
| GF3 (+) | 5'-GGGTAAAGGAGAAGAACTTT-3' | SEQ ID NO. 65 |
| GF4 (-) | 5'-ATGCCATGTGTAATCCCAGC-3' | SEQ ID NO. 66 |
| β-gal (pZeoSVLacZ) | | |
| BG1 (+) | 5'-CGGCACGCTGATTGAAGCAG-3' | SEQ ID NO. 67 |
| BG2 (-) | 5'-TGGACCATTTCGGCACAGCC-3' | SEQ ID NO. 68 |
| BG3 (+) | 5'-TCGCGTCACACTACGTCTGAA-3' | SEQ ID NO. 69 |
| BG4 (-) | 5'-CGCCTGCCAGTATTTAGCGAA-3' | SEQ ID NO. 70 |
| BG5 (+) | 5'-CCGCTGGATAACGACATTGG-3' | SEQ ID NO. 71 |
| BG6 (-) | 5'-GTTGCTGTTGACTGTAGCGG-3' | SEQ ID NO. 72 |
| BG7 (+) | 5'-TCTGACCACCAGCGAAATGGA-3' | SEQ ID NO. 73 |
| BG8 (-) | 5'-CCGTCGATATTCAGCCATGTG-3' | SEQ ID NO. 74 |
| BG9 (+) | 5'-GAAAATGGTCTGCTGCTGCTG-3' | SEQ ID NO. 75 |
| BG10 (-) | 5'-CGGGCAAATAATATCGGTGGC-3' | SEQ ID NO. 76 |
| BG11 (+) | 5'-TGTTGCAGTGCACGGCAGATA-3' | SEQ ID NO. 77 |
| BG12 (-) | 5'-GATGTTGAACTGGAAGTCGCC-3' | SEQ ID NO. 78 |

Table 8 lists sequences of PCR primers of the generation of therapeutic DNA fragments and for PCR analysis of SFHR. Therapeutic DNA was amplified from the wild-type (wt) plasmids indicated. Plasmid pcDNA3 contains the gene for neomycin resistance (neo$^r$), plasmid pGFP-N1 contains the gene for green fluorescent protein (GFP), and pZeoSV- LacZ contains the β-galactosidase gene (β-gal), Lac Z. The (+) indicates sense and (−) indicates antisense primers, respectively.

Schematic representation of the genes and the primers is seen in FIGS. 27–29.

FIG. 27 shows neomycin resistance gene (Neo) cDNA sequence (782-bp) inserted into the pcDNA3 plasmid. The gene has several unique restriction enzyme cleavage sites that can be used to introduce a mutation. The Kas I and the Bss HII have been used in initial studies. Because of the 4-bp 5' overhang (3' recessed end), it is possible to introduce a frame-shift mutation into the Neo gene that will inactivate the protein. The fill-in of the overhang will eliminate the Kas I site and create other restriction sites (Bss HII, Bst UI, Cac 8, Hha I). The fill-in of the Bss HII does not eliminate the Bss HII site, however, it does create several new sites (Bst UI, Cac 8, Hha I). The presence of the mutation can therefore be assessed by analysis with these new restriction sites.

Primers NY1 (bp 7, 22-bp), NY2 (bp 679, 22-bp), NY3 (bp 57, 22-bp), and NY4 (bp 609, 22-bp) seen in Table 8 are used for analysis of SFHR and generation of the therapeutic DNA fragment, respectively. Primers NY3/NY4 are used to generate the therapeutic fragment (574-bp) and primers NY1/NY2 are outside the region of homology define by NY3/ NY4 and yield a 694-bp fragment.

FIG. 28 shows the insert of the green fluorescent protein (GFP) cDNA (731-bp) in plasmid pGFP-N1. The unique Brs GI has a 4-bp 5' overhang (3' recessed end) that was filled in and resulted in a frameshift that inactivated the protein. The Brs G1 site is eliminated and replaced by other sites (Bsa I, Mae II, Rsa I, Sna Bl). Any of these enzymes are advantageous to assay for the presence of the mutation at the appropriate site. Primers GF1 (bp 758, 20-bp bp), GF2 (bp 1255, 20-bp), GF3 (bp 681, 20-bp), and GF4 (bp 1357, 20-bp) are used to generate the therapeutic fragment or for analysis of SFHR, respectively. Primers are listed in Table 8.

FIG. 29 shows the wtLacZ cDNA insert (3057-bp) in plasmid pZeoLacZ encoding for the β-galactoside (β-gal) gene. Two unique restriction sites, Bcl 1 and Bsi W1, give a 4-bp 5' overhang (3' recessed end) can be modified by fill-in to cause a frameshift mutation. The Bsi W1 is the site chosen initially because the Bcl 1 is methylation sensitive and is less straight forward to manipulate. Modification of the Bsl WI site results in other restriction sites (Bsa Al, Bsi W1, Mae II, Rsa I, Sna Bl). The Sna Bl enzyme is used for secondary analysis of the therapeutic DNA fragments and of the PCR analysis. Primers BG9 (bp 1386, 21-bp), BG10 (bp 1857, 21-bp), BG11 (bp 2839, 21-bp), and BG12 (bp 3231, 21-bp) are used to generate therapeutic fragments. BG9/ BG10 gives a 492-bp fragment and BG11/BG12 gives a 413-bp therapeutic fragment. Primers BG1 (bp 1331, 20-bp), BG2 (bp 1913, 20-bp), BG3 (bp 1235, 21-bp), BG4 (bp 2019, 21-bp), BG5 (bp 2736, 20-bp), BG6 (bp 3254, 20-bp), BG7 (bp 2591, 21-bp), and BG8 (bp 3317, 21-bp bp) are used in the PCR analysis of the homologous regions surrounding each region of homology defined by the frame-shift mutation. BG1/ BG2 and BG3/ BG4 give 602-bp and 805-bp fragments, respectively. BG5/ BG6 and BG7/ BG8 give 538-bp and 747-bp fragments, respectively.

Three different reporter/selectable genes were developed that serve as the basis for in vitro and in vivo model systems for quantifying the efficiency of homologous replacement. These system are also used to optimize the conditions for efficacious homologous replacement.

The frequency of homologous replacement is assessed as a restoration of gene (neo$^r$, β-gal, and GFP) function. With the neo$^r$ selection system, the frequency of homologous replacement is assessed by the appearance of neo$^r$ colonies. The fraction of neo$^r$ colonies is based on the total number of cells transfected with exogenous DNA fragments contain wt neo$^r$ gene sequences.

The β-gal reporter system indicates correction by the appearance of blue cells following X-gal treatment. Only the cells with a functional β-galatosidase gene are blue. The fraction of blue cells within the population of transfected cells is readily determined by cell counting.

The GFP reporter gene system has the advantage of retaining the viability of the cells during the process of defecting GFP gene function. Functional GFP will be assessed following illuminating the cells with blue or ultraviolet light and defecting green fluorescence either with a microscope or by flow cytometry. Relative numbers of fluorescing cells are then determined.

The systems involve the use of plasmids that contain the bacterial lac Z (β-galactosidase) β-gal gene or the neomycin resistance (aminoglycoside phosphotransferase) gene. Either gene is under the regulation of a eukaryotic promoter/enhancer. The genes (β-gal and neo$^r$) are mutated by the obliteration of a unique restriction enzyme site in the interior of the gene by either a fill-in-reaction or by enzymatic chew-back. The resultant mutant gene is now without the original restriction site and/or has a new restriction site in the mutated sequence. The restriction enzymes chosen to develop these mutant genes were such that the resultant fill-in or chew-back causes a frameshift in the coding sequence. This frameshift results in either the introduction of stop codons into the open reading frame (ORF) or a change in the amino acid sequence comprising the protein from the point of the mutation.

One such plasmid was made with a mutated lac Z gene.

Studies in cultured human airway epithelial cells have indicated that, whereas the wild-type β-galactosidase is expressed, the mutant form of the β-gal is nonfunctional. The cells were exposed to X-gal (a substrate for the β-gal), and those expressing the wild-type β-gal stained blue. Cells transfected with mutant β-gal or nontransfected control cells showed no blue cells, indicating the lack of a functional protein. The transfection efficiency appeared to be in the range of $10^{-3}$ to $10^{-2}$.

The cells containing the mutant β-gal are used to assess the rate of homologous replacement. They are under antibiotic selection so that clones of cells with the mutated plasmid can be isolated. The clonal populations is then be transfected with small DNA fragments that carry the wild-type β-gal sequences. Correction of the β-gal mutation by SFHR is assessed by the appearance of blue cells following X-gal exposure.

In parallel studies using a plasmid containing a neomycin resistance (neo$^r$) gene, a specific mutation was introduced through the elimination of a unique restriction enzyme site. The plasmid with the mutant neo$^r$ gene was cotransfected into cultured cells with another plasmid containing the hygromycin β-resistance gene. The cells were then selected with hygromycin B. Clones containing both the hygromycin resistance gene and the mutated neo were screened by genomic Southern hybridization and PCR analysis.

Transient expression of the neo$^r$ gene can also be assessed by immunocytochemistry with an antibody directed toward the neo$^r$ gene product. In this way, it is, therefore possible to determine the frequency of converting the mutant neo$^r$ gene to the wild-type by antibody staining. Additional studies will also be carried out in vivo with transgenic animals that have been transfected with the mutant neo$^r$ plasmid. The efficiency of SFHR is determined immunocytochemically. Cell cultures under G418 selection are established from various transfected organs to further indicate the efficacy of SFHR for correction of the neo gene mutation.

XIII. Composition

Further included in the invention is a composition comprising the small normal DNA fragment uncoated or coated with a recombinase enzyme. Examples of recombinase enzyme are UVSX, Rec A, Rad51 yeast recombinase, human recombinase including DMC and HPP1, although other enzymes are also suitable. The recombinase is preferably present in a ratio of about 1 protein molecule to every 3 bases. Other ratios, however, may also be used. When the DNA fragment is double-stranded the DNA is, preferably denatured prior to contacting it with the recombinase. The foregoing recombinases have been shown by the prior art to promote pairing of single-stranded DNA to double-stranded homologous DNA but not of two double-stranded oligonucleotides. These proteins are thus useful to increase the frequency of pairing between the altering DNA fragment and the cellular DNA fragment to be altered. The enhanced pairing by recombinases is especially useful where the frequency of recombination is low. The use of recombinases may also be beneficial to boost the frequency of targeted replacement where biologically effective therapy requires the alteration of a high percentage of target cells.

The administration to the subject of the normal DNA fragment is done by means of a composition comprising the normal DNA fragment and a pharmaceutically-acceptable carrier and/or other agents such as recombinase enzymes, a lipid agent, a lipid and protein agent, and the like.

Typically, the carrier may comprise solid, liquid or gaseous carriers. Examples of carriers are aqueous solutions, including water, buffered, aqueous solutions and the like.

While it is possible for the DNA fragment to be administered alone it is preferable to administer it as a pharmaceutical formulation.

Each carrier must be pharmaceutically acceptable, that is, being compatible with the other ingredients of the formulation and not injurious to the patient. Formulations include those suitable for oral, nasal, topical (including buccal and sublingual), rectal, vaginal and parenteral (including subcutaneous, intramuscular, intravenous and intradermal) administration.

Formulations suitable for parenteral administration, which is preferred, include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending and/or thickening agents. The formulation may be presented in unit dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

In addition, the above compounds according to the invention and their pharmaceutically acceptable derivatives may be employed in combination with other therapeutic agents for the treatment of the indicated conditions. Examples of such further therapeutic agents include agents that are effective for treatment of associated conditions. However, other agents that contribute to the treatment of the disease and/or its symptoms, such as inhibitors of neutrophyl function, retinoic acid, anti-inflammatory agents, adenosine agonists, and the like, are suitable.

In another preferred embodiment of the present composition, the altering DNA fragment is enveloped by a lipid layer, encapsulated by a lipid and a protein layer, or is complexed to dendrimer. The choice of the foregoing preparations will vary depending on the cell type used, the in vitro or in vivo conditions and the inherent limitations of each transfection method. Preferred conditions for enveloping the altering DNA fragment with a lipid layer are as follows. The altering DNA fragment is admixed with a lipid such as dioleophosphatidyl ethanolamine, dipalmitoylphosphatidylethanolamine (dipalmitoyl PtdEtn), palmitoyloleoylphosphatidylethanolamine (palmitoyloleoyl PtdEtn), dioleoylphosphatidylcholine (PtdCho), dimyristoylphospatidylethanolamine (dimyristoyl PtdEtn), diphytanoylgycero-phosphatidylethanolamine (diphytanoyl PtdEtn), N-monomethyl PtdEtn, and N-dimethyl PtdEtn in a proportion of about 1 $\mu$g: 1 nmole to 1 $\mu$g: 500 nmoles, in an aqueous solution. Other components and proportions are discussed below when this technology is applied to the in vivo method. The pH of the solution may be adjusted to about 8 to 10, and more preferably about 9. In addition to the above, ingredients such as a buffer and other known components may also be added to this composition. The amounts in which these components may be added are standard in the art and need not be further described herein.

In another preferred embodiment of the invention, the DNA sequence to be altered of the above composition comprises a DNA sequence encoding the cystic fibrosis transmembrane conductance regulator (CFTR) protein and the altering DNA sequence comprises a genomic region of the functional (normal) allele of the CFTR gene. Thus, a wild type allele may be utilized herein.

The above composition may also be compounded to alter simultaneously more than one cellular DNA sequence. For example, a majority of individuals with CF mutations have been localized to exon 10. Using available DNA libraries and the normal CFTR gene sequence functional wild-type DNA fragments homologous to CF mutations can be prepared.

The delivery of the normal DNA fragment into the cell may be conducted by a variety of techniques discussed above. These encompass providing the altering DNA fragment enveloped by a lipid layer, complexed with a protein and a lipid or adendrimer. The conditions for contacting any of these compositions with the cells to be altered were described above.

Suspensions of the altering DNA fragment may be prepared using pharmaceutically-acceptable/carriers, utilizing glycerol, liquid polyethylene glycols, oils and mixtures thereof with or without surfactants, wherein the carrier is capable of suspending powdered preparations of one or more components of the composition or suspending insoluble liquid dispersions (droplets) containing one or more components of the composition. Such suspensions may also contain surfactants, dispersing agents, gelling agents, thickening agents and compounds that may or may not be suitable to maintain physiological osmolarity, pH and isotonicity. Suspensions containing the composition or components thereof may thus be formulated into a fluid.

The method also comprises the administration of the composition of the invention by an intranasal or inhalation route. For intranasal or inhalation administration the DNA agent is compounded with an inert pharmaceutically-acceptable diluent wherein the diluent forms a solution or suspension using as a diluent a solvent or suspension medium containing, e.g., water, ethanol, polyols, oils and other similar compounds capable of aerosol formation. Such aerosol solution or medium may or may not contain compounds suitable to maintain physiological osmolarity, pH and isotonicity.

The foregoing method may be applied to a human afflicted with a genetic disease including, but not limited to, Fanconi's anemia, cystic fibrosis, retinitis pigmentosa, Xeroderma pigmentosa, ataxia telangiectasia, Bloom's syndrome, retinoblastoma, Duchenne's muscular dystrophy and Tay-Sachs' disease.

The complexing the DNA with lipid, lipid-protein, or dendrimer is especially applicable to in vivo transfection since less cell lethality is encountered, the DNA is protected from DNase degradation and the method is compatible with intracorporeal injection or administration.

One concern about the direct intravenous delivery of genes in vivo is the ability of the polynucleotide to survive in circulation long enough to arrive at the desired cellular destination.

In this respect, the coating or masking of the polynucleotide is of extreme utility. The utilization of liposomes, a lipoproteic, or a dendrimer coating is extremely useful. In addition, a successful liposome system uses the cationic lipid reagent dioleyloxytrimethalammonium (DOTMA). DOTMA may be mixed with phosphatidyl ethanolamine (PE) to form the reagent Lipofectin$^R$. When this reagent is utilized to carry the polynucleotides the liposomes are mixed with the DNA and readied for administration.

In addition to the above, efficient gene transfer requires the targeting of an altering DNA fragment to the cell of choice. This can be attained by procedures based upon receptor mediated endocytosis according to *J. Biol. Chem.*, 262:4429(1987); *J. Biol.Chem.*, 263:14,621 (1988)). This technology utilizes a cell-specific ligand-polylysine complex bound to the polynucleotide through charge interactions. This complex is taken up by the target cells. The successful transfection of a similar hepatoma cell line resulting in stable expression of enzymatic activity was reported following insulin-directed targeting *Biochem. Pharmacol.*, 40:253 (1985)). *PNAS*, (USA), 87:3410 (1990) and *PNAS*, (USA) 88:4255 (1991) utilized a transferrin-polycation to attain the delivery of a plasmid into a human leukemic cell line and observed expression of the encoded luciferase gene. These proteins require attachment to the polynucleotide via, for example, a polylysine linker.

Moreover, in many receptor-mediated systems as chloroquine or other disrupters of intracellular trafficking may be required for high levels of transfection. Adenovirus, for instance, has been used to enhance the delivery of polynucleotides in receptor-mediated systems (*PNAS* (USA), 88:8850 (1991)).

Alternatively, the DNA may be masked through association with lipids. In one embodiment, the DNA is encased in standard liposomes as described, for example, in U.S. Pat. No. 4,394,448, the relevant portion of the specification of which is hereby incorporated by reference. In another embodiment, the DNA is incubated with a synthetic cationic lipid similar to those described in U.S. Pat. No. 4,897,355 to Eppstein et al. The above-described synthetic cationic lipid effectively mask the DNA when associated therewith.

The cell recognition element is a molecule capable of recognizing a component on the surface of a targeted cell, covalently linked with a DNA-associating moiety by conventional methods. Cell recognition components include antibodies to cell surface antigens, ligands for cell surface receptors including those involved in receptor-mediated endocytosis, peptide hormones, etc. Specific ligands contemplated by this invention include carbohydrate ligands such as galactose, mannose, mannosyl 5-phosphate, fucose, sialic groups, N-acetylglucosamine or combinations of these groups as complex carbohydrates such as those found on glycolipids of the blood groups or on various secreted proteins. Other ligands include folate, biotin, various peptides that can interact with cell surface or intracellular receptors such as the chemoattractants peptide N-formyl-met-leu-phe, SEQ. ID. No.: 79 peptides containing the arg-asp-glycine sequence SEQ. ID. No.: 80 or cys-ser-gly-arg-glu-asp-val-trp SEQ. ID. NO.: 82 peptides, peptides that contain a cystine residue or that interact with cell surface protein such as the human immunodeficiency virus GP-120, and peptides that interact with CD-4. Other ligands include antibodies or antibody fragments. The specificity of the antibodies can be directed against a variety of epitopes that can be expressed on cell surfaces including histocompatibility macromolecules, autoimmune antigens, viral, parasitic or bacterial proteins. Other protein ligands include hormones such as growth hormone and insulin or protein growth factors such as GM-CSF, G-CSF, erythropoietin, epidermal growth factor, basic and acidic fibroblast growth factor and the like. Other protein ligands would include various cytokines that work through cell surface receptors such as interleukin 2, interleukin 1, tumor necrosis factor and suitable peptide fragments from such macromolecules.

The membrane-permeabilizing element of this system is a molecule that aids in the passage of a polynucleotide across a membrane. The liposomes, synthetic cationic lipids, lipid-proteins, and dendrimer described above as DNA-masking components also may function as membrane-permeabilization components.

Additional membrane-permeabilizing components that will facilitate this invention also include polycations that neutralize the large negative charge on polynucleotides. Polycations of this invention include polylysine, polyarginine, poly (lysine-arginine) and similar polypeptides, and the polyamines and the polycationic dendrimers.

The membrane-permeabilizing component that facilitates this invention may be an amphipathic cationic peptide. Amphipathic cationic peptides are peptides whose native configuration is such that the peptide is considered to have a cationic face and a neutral, hydrophobic face. In a preferred embodiment, the peptide is a cyclic peptide. Examples of the amphipathic cationic cyclic peptides of this invention are gramicidin S, and tyrocidines. The peptide may also contain some or all of the amino acids in the D configuration as opposed to the naturally occurring L configuration.

In a particularly preferred embodiment, the membrane-permeabilizing element includes, in addition to the amphipathic cationic cyclic peptides, a lipid, a dendrimer, or a simple polyamine or a combination of the above.

Other lipids utilized to facilitate the invention are amphipathic molecules which are capable of liposome formation, and are substantially non-toxic when administered at the necessary concentrations either in native form or as liposomes. Suitable lipids generally have a polar or hydrophilic end, and a non-polar or hydrophobic end. Suitable lipids include without limitation egg phosphatidylcholine (EPC), phosphatidylethanolamine, dipalmitoylphosphatidylcholine (DPPC), cholesterol (Chol), cholesterylphosphorylcholine, 3,6,9-tri-oxaoctan-1-ol-cholesteryl-3e-ol, dimyristoylphosphatidylcholine (DMPC), and other hydroxy-cholesterol or aminocholesterol derivatives. The lipid is preferably added in the form of liposomes. The added polyamine is preferably spermine or spermidine.

The membrane permeabilizing elements, i.e., the cyclic peptide and optional phospholipid and polyamine, may be added to the composition simultaneously or consecutively. Preferably, the cyclic peptide is added first, and the phospholipid or polyamine is added later. The molar ratio of added cyclic peptide to added polyamine is preferably from about 1:1 to about 1:3. The molar ratio of added cyclic peptide to added phospholipid is preferably from about 1:1 to about 1:20. The subcellular-localization element of this system is a molecule capable of recognizing a subcellular component in a targeted cell, covalently linked with a DNA-associating moiety by conventional methods. Particular subcellular components include the nucleus, ribosomes, mitochondria, and chloroplasts. In a preferred embodiment of this invention, the subcellular-localization component is a nuclear-localization component. The nuclear-localization components include known peptides of defined amino acid sequences, and longer sequences containing these peptides. One known peptide sequence is the SV40 large T antigen heptapeptide pro-lys-lys-lys-arg-lys-val SEQ. ID. NO.: 82. Other peptides include the influenza virus nucleoprotein decapeptide ala-ala-phe-glu-asp-leu-arg-val-leu-ser, SEQ. ID. NO.: 83, and the adenovirus E1a protein sequence lys-arg-pro-arg-pro. Other sequences may be discerned from *TIBS*, 16:478–481(1991).

In another embodiment, the DNA-associating moiety is a nonspecific DNA binder such as a polycation. Polycations include polylysine, polyarginine, poly (lysine-arginine) and similar polypeptides, and the polyamines and the polycationic dendrimers.

Utility

The current invention is useful for correction of genetic disorders. While the invention was proven to work for cystic fibrosis, almost all genetic diseases can be corrected according to the invention.

The direct administration of small ssDNA fragments, advances previous homologous replacement because it shows that homologous replacement with small genomic DNA fragments is successful to correct naturally occurring genomic CFTR mutations in CF epithelial cells in sickle cells and skin cells. In addition, SFHR has an advantage over vector based homologous recombination strategies reported before in *Nature*, 346:847 (1990) because intron sequences are not disrupted by selectable marker gene sequences. This eliminates the possibility of interference of marker gene transcription with that of the targeted gene. The SFHR approach also presents also presents an advantage over cDNA gene therapy strategies, because the corrected gene continues to be regulated by endogenous genomic enhancers and promoters rather than a heterologous enhancer and promoter in the vector. Thus, homologous replacement increases the probability that the corrected gene, whether CFTR or another gene, is expressed in the appropriate cells at the appropriate levels.

The foregoing method may also be used to alter DNA sequences in non-nuclear cellular DNA, present in the cell as mitochondrial DNA or as a virus, bacteria, plasmid or a hybrid vector.

It will be apparent to a person skilled in the art that this method also provides a means for altering DNA sequences which do not express a gene product, including alterations in regulatory sequences, intron sequences, and the substitution of redundant codon sequences. Other possible corrections include the insertion of functional DNA sequences other than normal wild-type DNA, which permit at least quasi-normal function and have an at least beneficial therapeutic effect on the subject. Generally, the altering DNA sequence need only be of at least sufficient size and of a sequence such that, after homologous replacement, it will provide a heterozygote cell having a genetic DNA capable of functional gene expression.

In a more preferred embodiment, the method of the invention is applied to the alteration of the genetic defect associated with CF disease. The method may also be applied to cells with other genetic defects for which the wild-type or otherwise normal DNA sequence is known. Also within this invention is the alteration of DNA sequences associated with genetic diseases in animals other than humans. These genetic diseases can either be induced as in the case of transgenic animals, or they can be corrected as in the case of gene therapy.

EXAMPLE 1

A Method and Conditions for Culturing Cells

This example illustrates procedure and conditions used for culturing cells.

The airway epithelial cells were grown either in serum free MLCH-8e (In Vitro *Cell Dev. Biol.*, 36:411 (1990) or in the case of transformed cells, Eagle's minimal essential medium (MEM) supplemented with 10% FBS, 4 mM glutamine, and antibiotics. Tissue culture plates were coated with fibronectin (FN), collagen (C) and bovine serum albumin (BSA). The growth medium was replaced with fresh medium every other day and the stock cultures were subcultured on reaching 80–100% confluence by trypsinization at a split ratio of between 1:2 to 1:4.

Tracheal epithelial cells were isolated and cultured as described. Non-transformed cells were grown in modified serum-free LHC-9 medium (MLHC-8e) on tissue culture plates that had been precoated with fibronectin, collagen, and bovine serum albumin according to *J. Tissue Culture Methods*, 9:43 (1985).

EXAMPLE 2

Development of Cell Line ΣCFTE29o-

This example illustrates procedure and conditions used for development of ΣCRTE29o- cell line. Examples 2–7 are published in *Am. J. Respir. Cell Mol. Biol.*, 8:52259 (1993).

Pure cultures of epithelial cells were transfected as described in *PNAS* (*USA*), 85:5951–5955 (1988); *PNAS* (*USA*), 89:5171–5175 (1992). The cells were grown in 100-mm precoated tissue culture dishes to 70–80% confluence and transfected with the linearized pSVori- vector obtained from Dr. John Murnane, a plasmid containing a replication deficient SV40 genome, via calcium phosphate precipitation PNAS 8515951-5955 (1988). The transfected cultures were grown in MLHC-8e medium at 37° C. under 5% $CO_2$ in air until cells with altered growth characteristics appeared (*BioTechniques*, 5:740–749(1987). Cell transformants were isolated by trypsinization and all the colonies were pooled and designated ΣCFTE29o-.

To enhance the ability of the cells to survive a crisis that generally occurs at about 15 passages post-transfection, the cells were transferred before the crisis occurred to Eagle's minimum essential medium supplemented with 10% fetal bovine serum (FBS) and an antibiotic at passage 5–7 post-transfection. The cells entered crisis at passage 17–18 post-transfection. The ΣCFTE29o-transformants were continuously grown post-crisis in supplemented MEM as described above.

EXAMPLE 3

Immunocytochemical Staining

This example illustrates a method used for immunocytochemical staining.

Cells grown on well slides (Lab-Tek, Naperville, Ill.) to various stages of confluence were washed three times with ice-cold phosphate-buffered saline (PBS) and then fixed with −20° C. acetone/methanol (2:3). After drying in air at room temperature, cells were rehydrated in PBS.

The primary antibodies used in these studies were L19 monoclonal antibody against the SV40 T-antigen (diluted 1:5). AE1/AE3 anti-cytokeratin antibody (diluted 1:10) (Boehringer Mannheim, Indianapolis, Ind.), and E9 monoclonal antibody against the junctional complex adhesion protein (diluted 1:10), cell CAM 120/80 described in *Cell Biochem*, 34:187–202(1987). The slides were washed with three changes of PBS containing 1% normal goat serum (30 min) before exposure to the secondary antibody (goat anti-mouse Ig/G-fluorescein isothiocyanate conjugate) diluted 1:40 in the buffer described above and viewed with a Zeiss fluorescence microscope (*PNAS*, 85:5951–5955 (1988)). SV40 T-antigen is expressed only in successfully transformed cells and cytokeratin and cell CAM 120/80 are expressed only in epithelial cells.

EXAMPLE 4

Fluorescence in Situ Hybridization (FISH)

This example illustrates a fluorescence in situ hybridization method.

Chromosomal analysis by FISH was carried out as described in *Proc. Nat. Acad. Sci.* (*USA*), 83:2934–2938 (1986); and in *Cancer Res.*, 51:3807–3813 (1991)).

Briefly, cells were grown on single chamber well slides (LAB TEK) to confluence, washed twice with PBS, and fixed with acetic acid:ethanol (1:3). Slides were covered with 70% formamide, 2×SSC, pH 7.0, the cellular DNA was denatured by heating at 70° C. for 2 min. Regions of the slide were selected for chromosome analysis. Cells were then dehydrated sequentially by dipping the slide in 70%, 85%, and 100% ethanol for 3 min. each at room temperature. The slide was air-dried and warmed at 37° C. for application of the hybridization mix having the following.

7 μl, Master Mix #2.1 obtained from Pharmacia, 5.5 ml formamide, 1 g dextran sulfate, sodium salt; 0.5 ml 20×SSC, pH 7.0, final volume 7 ml; 0.5 μl carrier DNA (100 μg/ml), 1 μl biotinylated repetitive probe (p$^\alpha$ter) specific for chromosome 7 centromere and 1.5 μl dd H$_2$O.

The hybridization mix was denatured by heating to 70° C. for 5 min and applied immediately to the prepared slides. The slides were covered with glass coverslips and edges were sealed with rubber cement. The hybridization reaction was carried out in a humidified chamber overnight at 37° C.

Following the hybridization, the coverslip was removed and the cells were washed 2 times at 3 minute intervals with changes of washing solution containing 50% formamide, 2×SCC, pH 7.0, in PN buffer containing 0.1 M NaH$_2$PO$_4$, 0.1 M Na$_2$HPO$_4$, pH 8.0 and 1% Nonidet P-40, prewarmed to 45° C. at room temperature. The slides were then stained with 5 μg/ml FITC-avidin in PNM buffer containing 25 gm nonfat dry milk powder in 500 ml PN buffer at room temperature for 20 min under a coverslip.

The cells were then washed with 2 changes of PN buffer for 3 min at room temperature and incubated with biotinylated anti-avidin (5 μg in PNM solution) at room temperature for 20 min under a coverslip. The slides were washed with two changes of PN buffer, 3 min. each, at room temperature and the cells stained with FITC-avidin (5 μg/ml in PNM solution) at room temperature for 20 min under a glass coverslip. The slides were again washed 2 times, 3 min each, with PN buffer at room temperature. Prospidium iodide (2 μg/ml) was then added and the slides were viewed by fluorescence microscopy. The number of copies of chromosome 7 per cell was determined by counting fluorescent dots per nucleus.

EXAMPLE 5

Isolation and Purification of DNA and RNA

This example illustrates isolation and purification of DNA and RNA.

Cellular RNA and DNA was isolated as previously described in *Nucleic Acids Res.*, 10:4609–26 (1982), and in *Molecular Cloning: a Laboratory Manual*, Cold Spring Harbor Press, Cold Spring Harbor, N.Y., 1989).

Cells were washed twice with cold phosphate buffered saline (PBS) and then trypsinized at room temperature to obtain a single cell suspension. The single cell suspension was added to an equal volume of medium containing 10% fetal calf serum and centrifuged at 1000 g. The fetal calf serum serves to inhibit the trypsin and minimizes rupturing of the plasma membrane.

The pellet was washed twice with ice-cold PBS and the cells were then resuspended in Lysis Buffer I containing 0.65% NP40, (a detergent), 10 mM Tris, pH 7.8; 150 mM NaCl; and 1.5 mM MgCl$_2$.

The suspension was vortexed on and off for 10 min on ice. This suspension was centrifuged and the cytoplasmic supernatant separated from the nuclear pellet. The mRNA-containing supernatant was diluted with an equal volume of urea buffer containing 7 M urea, 10 mM Tris, pH 7.5, 10 mM ethylenediaminetetraacetic acid (EDTA), 350 mM NaCl, and 1% sodium dodecyl sulfate (SDS).

After one extraction with an equal volume of phenol, the RNA was precipitated with 100% ethanol at −20° C. overnight. The RNA pellet was then resuspended in diethyl pyrocarbonate (DEP)-treated H$_2$O and stored at −70° C. for further analysis. PolyA$^+$ RNA was isolated with a commercially available kit obtained from Pharmacia, N.J.

The nuclear pellet was resuspended in Lysis Buffer II containing 0.1% SDS, 100 mM NaCl, 40 mM Tris, pH 7.5, and 20 mM EDTA for DNA extraction.

The DNA lysate was incubated overnight at 50° C. in the presence of 100 mg/ml proteinase K. After a gentle extraction with an equal volume of phenol, the DNA was precipitated overnight at −20° C. in 300 mM sodium acetate, pH 4.8, with 2 volumes of 100% ethanol. The DNA pellet was washed one time each with 70% and 100% ethanol, and slowly resuspended in TE (10 mM Tris, 1 mM EDTA PH8.6) buffer. The DNA concentrations were determined spectrophotometrically and the samples were stored at −20° C.

EXAMPLE 6

Determination of ΣCRTE29o- Phenotype by Chloride Flux

The chloride ion transport was measured with radioactive $^{36}$Cl efflux according to Cell, 66:1027–36 (1991), and N. Eng. J. Med., 323:1685(1990). The cells were grown to confluence in MEM with 10% FBS and the cultures were then rinsed twice with 2 ml efflux buffer. The efflux buffer contained 140 mM NaCl, 3.3 mM $KH_2PO_4$, 0.83 mM $K_2HPO_4$, 1 mM $CaSO_4$, 1 mM $MgSO_4$, 10 mM HEPES, pH 7.4, and 10 mM glucose.

1 ml fresh efflux buffer with 2 $\mu$Ci/ml $^{36}$Cl was added to each dish, and then cells were incubated for 2 hrs at 37° C. The dishes were washed by dipping each one into 200 ml of efflux buffer for 8–10 seconds.

Following washing, 1 ml efflux buffer was added, and the cells were again incubated at 37° C. Samples were removed at 1 min intervals and replaced with fresh buffer. At 3 min, efflux buffer was added. The efflux buffer contained 10 $\mu$M isoproterenol available from Sigma, St. Louis, Mo., 500 $\mu$M 8-(4-chlorophenylthio)-adenosine-3',5'-cyclic monophosphate (CPT-cAMP) available from Boehringer-Mannheim, Indianapolis, Ind., 10 $\mu$M forskolin available from Sigma), or 0.5 $\mu$M ionomycin (Sigma).

Samples containing agonist were removed and replaced at 1 min intervals. The cells were extracted with 0.1 N HCl (1 ml) overnight at 4° C. and the $^{36}$Cl remaining in the cells was determined.

The samples were counted in scintillation cocktail and the % efflux/1 min time point calculated as follows % efflux/min=(cpm sample/average cpm in cells for that minute).

The average cpm/1 min time interval is $(cpm_t+cpm_{t-1})/2$, where $cpm_t$ are the cpm for the sample at min (t) and $cpm_{t-1}$ are the cpm for the sample at the previous min.

EXAMPLE 7

Determination of ΣCRTE29o- Phenotype by Whole-cell Patch Clamp

This example illustrates determination of phenotype in ΣCRTE29o- cells by using the whole-cell patch clamp.

The cells were observed 2–3 days after plating on FN/C/BSA coated glass coverslips. Whole cell patch clamp measurements were conducted as described previously in Pflugers Arch., 391:85–100(1981) at 23° C. using a Warner patch clamp amplifier (Hamden, Conn., USA). The average seal resistance was 1.2±0.1 GΩ. The membrane voltage was clamped to a holding voltage of 0 mV and stepped in 10 mV increments using P clamp 5.51 software (Axon Instruments; Foster City, Calif.). The currents were stored on a Everex AT computer, filtered at 1–5 kHz and analyzed by P clamp 5.51 software. Current magnitude was measured during the last 20 ms of an 140 ms voltage pulse. Whole cell capacitance (Cp) was calculated by exponential fit of the RC decay of the transient capacitance spike as described ibid, supra; or in Am. J. Physiol., 258:F562–F567 (1990)).

The Cp values (in pF) were as follows.

9HTEo-, 6.5±2.3 (n=9);

ΣCFTE29o-, 15.3±1.5 (n=9); and

2CFSMEo-, 16.5±1.7 (n=6).

The pipette solution contained 140 mM N-methyl-D-glucamine Cl, (NMDG-Cl), 1 mM $MgCl_2$, 5 mM HEPES, and 100 nM $Ca^{2+}$ (buffered with 1 mM EGTA), pH 7.4. The bath solution contained 140 mM NMDG-Cl, 1 mM $CaCl_2$ 5 mM HEPES, and 60 mM sucrose pH 7.4.

These solutions were used to prevent a volume induced chloride current because these solutions did not contain $K^+$ or Na+, the observed whole cell currents are referable primarily to Cl$^-$. CPT-cAMP and ionomycin were added to the bath solution to assay for cAMP- and Ca-dependent Cl$^-$ currents in the 9HTEo- and the ΣCFTE29o- cells. The Cl$^-$ channel blocker used was 4, 4'-diisothiocyanatostilbene-2, 2'-disulfonic acid (DIDS, Sigma). P values were calculated using paired Students' t- test, unless otherwise indicated.

EXAMPLE 8

Preparation of the Wild-type 491 Base Pair DNA and Primers

This example illustrates preparation of the wt 491 bp DNA and primers.

The 491 bp fragment was generated using the T6/20 plasmid described in Science, 245:1059–1065(1989), (ATCC, NJ). The identity of the plasmid was verified by restriction enzyme mapping and further amplified as previously described. After digestion with Eco RI and Hind III, an 860 bp DNA was separated following electrophoresis in 0.8% Seaplaque agarose gel. The fragment obtained contained exon 10 as well as 5' and 3' intron sequences as verified by the restriction enzyme cleavage Genomics, 10:214–228(1991)). A 50 ng aliquot of the DNA fragment was amplified by the polymerase chain reaction (PCR) (US Pat. No. 4,965,188) using primers CF1 and CF5.

The amplified fragment was analyzed on a 1% agarose gel, and then amplified in bulk in 20 separate PCR amplifications each containing 50 ng. The 491 bp fragments were purified by phenol:chloroform:isoamyl alcohol (25:24:1) extraction, and precipitated with 100% ethanol at −70° C. for 30 min. The DNA was centrifuged in an Eppendorf microcentrifuge at 14,000 rpm, for 10 min at 40° C. The pellet was washed once with 70% ethanol and then with 100% ethanol. After drying, the DNA was resuspended in dd $H_2O$ at a concentration of 1 $\mu g/\mu l$.

Primers and probes were prepared on automated DNA Synthesizers (Models 390B and 394, Applied Biosystems, Foster City, Calif.).

The sequences of the primers and probes were selected from the CFTR gene sequence published in Genomics, 10:214–228 (1991). The sequences of the primers are shown in Table 1.

EXAMPLE 9

PCR Conditions

This example describes condition used for amplification of primers by PCR.

The PCR conditions for individual primers are as follows:

CF1/CF5 (491 bp fragment)

10 ng DNA, 10–30 pmole primer, 1.5 mM $Mg^{+2}$.

Cycle: denaturation 94° C. for 1 min, annealing 53° C. for 30 sec, extension 72° C. for 30 sec with a 4 sec increase in the extension time per cycle for 40 cycles.

CF1/CF6 primers (684/687 bp fragment)

0.5 $\mu$M primers, DNA 1–2 $\mu$g, 1.5 mM $Mg^{+2}$.

Cycle: denaturation, 94° C. for 1 min, annealing, 53° C. for 45 sec; extension, 72° C. for 90 sec with a 4 sec/cycle increase in extension time for 40 cycles.

CF6/CF7/8 (404/407 bp fragment)

1:500 dilution of DNA from CF1/CF6 amplification, 1 µM primers, 0.8 mM $Mg^{+2}$.

Cycle: denaturation 94° C. for 30 sec, annealing 49° C. for 20 sec extension 72° C. for 20 sec with a 4 sec/cycle increase in extension time for 35 cycles.

CF17/22 (470 bp fragment CFTR gene 1338-1811),

CF9/CF14 (627 bp fragment, CFTR gene 622-1248)

DNA amplified from 1 µg RNA (35 cycles), 1 µM primers, 0.8 mM $Mg^{+2}$.

Cycle: denaturation 94° C. for 30 sec, annealing 55° C. for 30 sec, extension 72° C. for 20 sec increasing 3 sec/cycle for 40 cycles.

CF17/oligo N/oligo ΔF

DNA amplified from 1 µg RNA (35 cycles), 1 µM primer, 1.5 mM $Mg^{+2}$.

Cycle: denaturation 94° C. for 1 min, annealing 51° C. for 1 min extension 72° C. for 20 sec with a 4 sec/cycle increase in extension time for 40 cycles.

C16B/C16D 2 to 5 µg DNA, 1 µM primer, 1.5 mM $Mg^{+2}$.

Cycle: denaturation for at 94° C. for 1 minute, annealing for 45 sec at 62° C., and extension at 72° C., starting with 120 sec and increasing to 7 min over 28 cycles.

CF1B/CF6:768/771-bp N or ΔF product, respectively were as follows:

Primers, 0.4 µM; DNA, 50–100 ng; denaturation, 95° C. for 60 s; annealing, 56° C. for 45 s; extension, 72° C. for 90 s for 30 cycles; and $Mg^{+2}$ 1.5 mM.

CF7B/CF6 and CF8B/CF6: 414- and 411-bp fragments, respectively; primers, 0.5 µM; DNA, 50–100 ng; denaturation, 95° C. for 60 s, annealing 56° C. for 60 s, 72° C. for 120 s; 35 cycles with an 8 min extension on the last cycle; and $Mg^{+2}$ mM.

CF1B/CF7C (N) and CF1B/CF8C (ΔF):392- and 389-bp fragments, respectively. Conditions were as follows: primers, 0.5 µM;DNA, 50–100 ng; denaturation, 95° C. for 60 s, annealing 59° C. for 60 s, 72° C. for 90 s; 35 cycles with an 8 min extension on the last cycle; and $Mg^{+2}$ 2 mM.

CF17/CF7C-8C: 330-bp (N) AND 327-bp (ΔF), primers, 1 µM; denaturation, 94° C. for 30 s; annealing, 57° C. for 30 s; extension, 72° C. for 30 s for 35 cycles with a 5 min extension on the last cycle; and $Mg^{+2}$, 2.0 mM.

CF39/C16D: 485-bp, primers, 5 µM; denaturation, 94° C. for 20 s; annealing, 58° C. for 60 s; extension, 72° C. for 90 s for 30 cycles with a 5 min extension on the last cycle; and $Mg^{+2}$, 2.0 mM.

CF40/CF41: 1057-bp, primers, 5 µM; denaturation, 94° C. for 20 s; annealing, 58° C. for 60 s; extension, 72° C. for 90 s for 30 cycles with a 5 min extension on the last cycle; and $Mg^{+2}$, 2.0 mM.

SC1/SC2: 990-bp, primers, 5 µM; denaturation, 94° C. for 30 s; annealing, 60° C. for 30 s; extension, 72° C. for 60 s for 35 cycles with a with a 5 min extension on the last cycle; and $Mg^{+2}$, 2.5 mM.

SC3/SC4: 743-bp, primers, 5 µM; denaturation, 94° C. for 20 s; annealing, 60° C. for 20 s; extension, 72° C. for 60 s for 35 cycles with a with a 5 min extension on the last cycle; and $Mg^{+2}$, 2.5 mM.

SC5/SC6: 357-bp (DNA PCR) 227-bp (RT-PCR), primers, 5 µM; denaturation, 94° C. for 20 s; annealing, 58° C. for 60 s; extension, 72° C. for 60 s for 35 cycles with a with a 5 min extension on the last cycle; and $Mg^{+2}$, 2.5 mM.

SC3/SC6: 460-bp, primers, 5 µM; denaturation, 94° C. for 20 s; annealing, 60° C. for 20 s; extension, 72° C. for 60 s for 35 cycles with a with a 5 min extension on the last cycle; and $Mg^{+2}$, 2.5mM.

CF17/CF22: 470-bp (ΔF) and 473-bp (N) fragments. Conditions were as follows: primers, 0.5 µM; DNA, 5–100 ng; denaturation, 94° C. for 30 s, annealing 56° C. for 30 s, 72° C. for 30 s; 30 cycles with an 8 min extension on the last cycle; and $mg^{+2}$ mM.

NY1/NY2: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^{+2}$ 2 mM.

NY3/NY4: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^{+2}$ 2 mM.

GF1/GF2: Conditions were as follows: primers, 0.5 µM; DNA, 5–100 ng; denaturation, 94° C. for 20 s; annealing 60° C. for 20 s, 72° C. for 60 s; 20 cycles with an 8 min extension on the last cycle; and $Mg^{+2}$ 2 mM.

GF3/GF4: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^{+2}$ 2 mM.

BG1/BG2: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^{+2}$ 2 mM.

BG3/BG4: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^2$ +2 mM.

BG5/BG6: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^2+$ 2 mM.

BG7/BG8: Conditions were as follows: primers, 0.5 µM; DNA, 5–100 ng; denaturation, 94° C. for 20 s, annealing 60° C. for 20 s, 72° C. for 60 s, 20 cycles with an 8 min extension on the last cycle; and $Mg^{+2}$ 2 mM.

BG9/BG10: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle; and $Mg^2+2$ mM.

BG11/BG12: Conditions were as follows: primers, 0.5 µM; DNA, 5–100 ng; denaturation, 94° C. for 20 s, annealing 60° C. for 20 s, 72° C. for 60 s; 20 cycles with an 8 min extension on the last cycle: and $Mg^{+2}$ 2 mM.

EXAMPLE 10

Hybridization of Probes

This example illustrates the conditions for hybridization of probes.

The hybridization was carried out according to method described in Example 7 above. Fragments were separated by agarose gel electrophoresis. The gels with the fragments were incubated in 0.4 N NaOH containing 0.6 M NaCl for 30 min to denature DNA and then washed one time with 1.5 M NaCl, 0.5 M Tris-HCl for 30 min.

The DNA was transferred to a Gene Screen Plus membrane (NEN-Dupont) by capillary blot and again denatured with 0.4 N NaOH for 1 min followed by neutralization with 0.2 M Tris-HCl. The membranes were prehybridized for 1 hour at 37° C. in 6×SSC, 5×Denhardt's, 1% SDS, and 100 μg/ml of denatured salmon sperm DNA.

The oligonucleotide probes (oligo N or oligo ΔF; 10 ng) were radiolabelled by reaction with 20 units of T4 kinase and 40 μCi $^{32}$P-γ-ATP for 30 min at 37° C. Unincorporated nucleotides were removed by centrifugation of the reaction mix through a minispin column.

Hybridization was carried out overnight at 37° C., the membranes were washed 2 times for 5 min each in 2×SSC at room temperature, 2 times for 30 min in 2×SSC, 0.1% SDS at 45° C., and 1 time in 0.1×SSC for 30 min at room temperature. Autoradiographic emulsion was applied to the membranes after washing.

EXAMPLE 11

Preparation of Denatured DNA for Transfection and Homologous Recombination

This example describes conditions used for preparation of denatured DNA for transfection and homologous replacement.

The 491 bp fragment was prepared as described, denatured by heating to 95° C. for 10 min and then rapidly cooled on ice. 5 μl of the DNA were then added to a buffer solution. The buffer contained 20 mM Tris acetate, 10 mM Mg acetate, 70 mM potassium acetate, 1 mM dithiothreitol, and 100 μg/ml bovine serum albumin-fraction V, 0.5 mM ATP-γ-S followed by the addition of UvsX: 20 μl of a 1.4 mg/ml solution according to *J. Biol. Chem.*, 261:6107–6118 (1985); UvsY: 36 μl of a 0.5 mg/ml solution J. Biol. Chem., 268:15096–15103(1990); and T4 G p32: 100 μl of a 5.2 mg/ml solution according to *J. Biol. Chem.*, 263:9427–9436 (1987) to a final volume of 250 μl.

The ratio of UvsX molecules to DNA bases to UvsY molecules to T4Gp32 molecules was 4:64:1:17. The fragments were then coated with UvsX by incubating the solution for 10 min at 37° C. and then kept on ice for 10 min before transfection.

EXAMPLE 12

Identification of ΔF508 Deletion in Genomic DNA by Allele Specific Southern Blot hybridization This example describes conditions used for identification of Δ deletion in genomic DNA.

The presence of a ΔF508 mutation in the cellular DNA was tested as described in *Science*, 245:1073–1080(1989)). The presence of the ΔF508 deletion was determined by preparing genomic DNA by PCR. Using Southern blot hybridization, the PCR amplified DNA was exposed to probes with normal or ΔF508 specific radiolabelled oligonucleotides.

DNA from CF cells known to be heterozygous for the ΔF508 mutation (2CFSMEo-) and from normal cells (16HBE14o-) were used as controls.

Genomic DNA was prepared from transformed epithelial cell lines and amplified by PCR using the GeneAmp kit (Perkin Elmer Cetus, Emeryville, Calif.). Oligonucleotide primers C16B and C16D described in *Science*, 245:1066:73 (1989) were used for amplification of the CFTR region around the Exon 10 ΔF508 deletion site.

The PCR products were separated on 1.4% agarose gels and transferred to Gene Screen Plus membranes (NEN Dupont, Wilmington, Del.). Oligonucleotide probes (10 ng each) for the normal CFTR DNA (5'-CACCAAAGATGATATTTTC-3') SEQ. ID. NO:14 and for the ΔF508 deletion (5'-AACACCAATGATATTTTCTT-3') SEQ. ID. NO.:15 were labeled with -γ-[$^{32}$P]ATP.

The filters were hybridized overnight at 37° C. with a labeled oligonucleotide probe in a 6×SSC solution (1×SSC contains 150 mM NaCl, 15 mM trisodium citrate, 1% SDS, 1 g/l ficoll, 1 g/l bovine serum albumin fraction V, 1 g/l polyvinylpyrrolidone$^{600}$ W , and 100 mg/ml sonicated salmon sperm DNA). The membranes were washed twice with 2×SSC at room temperature for 5 min, twice at 45° C. in 2×SSC, 0.1% SDS for 30 min, and once at room temperature in 0.1×SSC for 30 min. Bands hybridizing to radioactive probes were identified autoradiographically.

EXAMPLE 14

Determination of CFTR mRNA Expression This example describes procedure used for determination of CFTR mRNA expression.

Cytoplasmic RNA from $10^6$ to $10^8$ cells was isolated as described above and the concentration was determined spectrophotometrically. Total cytoplasmic RNA (1 μg) was denatured by heating to 95° C. for 2 min, and reverse transcribed using the RT-PCR GeneAmp kit (Perkin Elmer Cetus, Emeryville, Calif.). The first-strand cDNA was PCR-amplified from exon 9 to 11 (fragment A) or from exon 5 to 7 (fragment B) according to *PNAS* (*USA*), 89:5171–5175 (1992), using oligonucleotides that span intron-exon boundaries. This procedure eliminates amplification of genomic DNA.

The amplification of fragment A using primers CF17 (sense) and CF22 (antisense) yielded a 474 bp product (nucleotide positions 1338-1811 of the CFTR gene).

The amplification of fragment B with primers CF9 (sense) and CF14 (antisense) yielded a predicted 627 bp product (nucleotide positions 622-1248 of the CFTR gene). The PCR products were separated by electrophoresis on 1% agarose gels and stained with ethidium bromide.

EXAMPLE 15

Formation of DNA-Lipid-Protein Complex and Cell Transfection

This example illustrates formation of DNA-lipid complex and cell formation.

A DNA protein complex encapsulated by lipid was prepared as described in Legendre (Legendre, PNAS (USA) 90:893–897 (1993).

Dioleoylphosphatidylethanolamine (DOPE) was used for the preparation of the liposomes. Liposomes were prepared by drying 4 μM of DOPE under nitrogen at room temperature. The lipid film was rehydrated with 4 ml of 30 mM Tris HCl buffer, pH 9, and then sonicated for 15 min under argon.

The DNA-protein complex was prepared by diluting 20 μg of DNA (UvsX coated or uncoated) in 30 mM Tris HCl (pH 9) from 20 mg/ml solution in dimethyl sulfoxide. The gramicidin S (40 μg) was added to the DNA and rapidly mixed. Then, the lipids prepared above were added and the mixture of 175 μl (175 nmoles) was slowly and gently mixed.

Cells (ΣCFTE29o-) at 70–80% confluence were incubated in the presence of the lipid-gramicidin S-DNA complex (5 μg per dish) in serum-free MEM for 5 hrs at 37° C. under oxygen with 5% $CO_2$. The transfection/ incubation medium was then replaced with growth medium. Growth medium consisted of MEM supplemented with 10% FCS, 100 µg/ml streptomycin and 100 U/ml penicillin. The cells were then grown until harvest with daily replacement of medium.

EXAMPLE 16

DNA Transfection by Electroporation Leading to Homologous Replacement

This example describes procedure used for DNA transfection by electroporation leading to subsequent homologous replacement.

Transfection by electroporation was carried out on ΣCFTE29o- cells using Rec uncoated DNA prepared as described above.

At confluence, the cells were trypsinized and $10^8$ cells were suspended in 400 µl of medium in the presence of 5 µg of the uncoated DNA. The cell suspension was kept on ice for 10 min then electroporated at 400 V and 400 µF in a BTX electroporator (BTX Corporation, San Diego, Calif.). After electroporation, the cells were kept on ice for an additional 10 min, plated in a T75 flask with an approximate survival of 30–50%, cultured for 5 to 7 days, and then harvested for analysis of DNA and RNA.

EXAMPLE 17

Transfection by Micro-injection Leading to Homologous Recombination Replacement

This example describes procedure used for transfection of cells by microinjection and subsequent homologous replacement.

Microinjection was conducted with an Eppendorf 5242 microinjector connected to a Eppendorf 5170 micromanipulator. Borosilicate pipettes (Brunswick, 1.2 mM OD×1.9 mM ID) were prepared on a Sutter Instruments pipette puller (model p-87). Cells were viewed with an Olympus IMT-2 inverted microscope during injection. The cells were washed 2 times in phosphate buffered saline and injected under non-sterile conditions at room temperature in growth medium. The area of injected cells was marked on the side by 2–5 mm diameter rings. The cells were injected with 1000–10000 Rec A (or recombinase coated) fragments per cell by intranuclear injection with 120 hPa for 0.1–0.3 sec at a volume of 1–10 fl of DNA /nucleus. The cells remained outside the incubator for a maximum of 15 min. After injection, non-injected cells were removed by scraping. The injected cells were grown for 7 days and then harvested for DNA analysis.

EXAMPLE 18

Targeted Replacement of Mutant CFTR DNA: mRNA Expression Ion Transport in CF Epithelial Cells This example describes methods used for targeted replacement of mutant CFTR DNA by homologous recombination, subsequent mRNA expression and regained normal functionality of the treated epithelial cells.

Cells and Culture Conditions

An SV40-transformed CF tracheobronchial epithelial cell line, ΣCFTE29o-, a transformed CF nasal polyp cell line, ΣCFNPE14o-, or the pancreatic adenocarcinoma cell line, CFPAC-1 were used. All cell lines were homozygous for the ΔF508 mutation (ΔF508/ΔF508). The ΣCFTE29o- and ΣCFNPE14o- cell lines were grown in Eagle's minimal essential medium (MEM) supplemented with 10% fetal bovine serum (FBS) antibiotics, while the CFPAC-1 cells were grown in Dulbecco's modified Eagle's/Ham's F12 medium (DME/F12; 1:1). NonCF, 16HBE14o- cells were cultured as indicated for the ΣCFTE29o- cells. All cell lines were grown under humidified conditions in an atmosphere 5% in $CO_2$ at 37° C.

Gene Transfer

A 491-bp fragment was generate by PCR amplification from plasmid T6/20 (2) (ATCC, N.J.). The plasmid was verified by restriction enzyme mapping, propagated, and digested with Eco RI and Hind III. A 860-bp insert was isolated by electrophoresis in 0.8% Seaplaque agarose gel. The 860-bp fragment contained CFTR exon 10, as well as 5' and 3' intron sequences, as defined by the restriction enzyme cleavage sites. A 50 ng aliquot of the DNA fragment was amplified by PCR using primers CF1 and CF5 seen in Table 1 to generate the 491-bp fragment. The conditions for amplification were denaturation, 94° C. for 1 min.; annealing, 55° C. for 30 s; extension, 72° C. for 30 s with a 4 s/cycle increase in the extension time for 30 cycles. The fragment size was confirmed by electrophoresis on a 1% agarose gel, then amplified in bulk in 20 separate PCR amplifications, each containing 50 ng of target DNA. The 491-bp PCR products were extracted with phenol: chloroform: isoamylalcohol (25:24:1) and precipitated with ethanol. DNA precipitates were collected by centrifugation for 10 mins. in an Eppendorf microcentrifuge (14,000 rpm) and resuspended at a final concentration of 1 mg/ml. The 491-bp fragment contained exon 10 (192-bp), as well as 5' (163-bp) and 3' (136-bp) flanking intron sequences, as defined by primers CF1 and CF5. The 491 nucleotide single stranded DNA (ssDNA) fragments used in the homologous replacement studies were either coated with recombinase protein (Pharmacia, Piscataway, N.J.) using the method in *J. Biol. Chem.*, 263:15110 (1988) or left uncoated. For recombinase coating, the 491-bp DNA fragment (5 µg in a 4 µl volume) was denatured at 95° C. for 10 mins., immediately placed in an ice-water bath, then added to a 63 µl of reaction buffer containing 200 µg of recombinase protein, 4.8 mM ATPγS, 2 mM Mg-acetate, and 1.7 µl reaction buffer (100 mM Tris-acetate, pH 7.5 at 37° C.; 10 mM dithiothreitol; 500 mM Na-acetate) (final volume 67 µl) and incubated for 10 mins. at 37° C. Next, the Mg-acetate concentration was increased to 20 mM by adding 7 µl of 200 mM Mg-acetate. Under these conditions, the 491 nucleotide ssDNA fragments were coated with recombinase protein at a molar ratio of 3 bases per 1 recombinase molecule. After coating, the fragments were immediately placed on ice at 4° C. until transfection (10 mins. to 1 hour). Fragments left uncoated were taken through the above protocol in the absence of recombinase.

Electroporation

Electroporation experiments were performed using recombinase-coated 491-mer ssDNA as described above. Approximately $10^7$ exponentially growing cells were suspended in 400 µl of recombinase coating buffer with 5 µg (5 µl) of recombinase-coated DNA. The cell suspension was preincubated on ice for 10 mins. and electroporated at 4° C. with 400 V and 400 µF in a BTX 300 elecroporator (BTX Corporation, San Diego, Calif.). After electroporation, cells were incubated on ice for an additional 10 mins., diluted in Eagle's minimal essential medium (MEM) supplemented as described above, then seeded in a T75 flask. Under these electroporation conditions, approximately 30–50% of the cell survive. Cells were cultured at 37° C. in a humidified CO$_2$ incubator for 5–7 days and then harvested for DNA and RNA.

Liposome and Dendrimer Complexes

Protein-DNA lipid complexes were prepared with dioleoylphosphatidylethanolamine (PtdEtn, DOPE) by drying the lipid under nitrogen at room temperature. The lipid film was rehydrated with 30 mM Tris HCl buffer (pH 9), then sonicated for 15 mins. under an argon atmosphere. The protein-DNA complex was prepared in polystyrene tubes by diluting 20 μg of DNA, either uncoated or rec A-coated, in 30 mM Tris HCl (pH 9) buffer. Protein was added to the DNA and rapidly mixed. Next, 175 μl of the lipid solution (175 nmol of lipid) was added to the protein-DNA mixture to create the protein-DNA-lipid complex.

DNA-dendrimer complexes (*Bioconjugate Chem.* 4:95–93 (1993) were prepared with 4 μg of DNA in rec A coating buffer (45 μl) diluted to a final volume of 300 μl in HEPES buffered saline, 10 mM HEPES, 150 mM NaCl, pH 7.3 (HBS). In a separate polystyrene tube, 25 μg of Starbust™ dendrimer, 6th generation (23) (in 25 μl, 0.1% w/v) was diluted into a final volume of 170 μl with HBS. The dendrimer solution was then added dropwise to the DNA solution. The transfection cocktail (500 μl/flask) was incubated at room temperature for 5–10 minutes and then placed into a T25 flask containing (1 ml) serum-free medium. Cells transfected with protein-DNA lipid or DNA dendrimer complexes were grown to 70–90% confluence and incubated in the presence of protein-DNA-lipid complex (4 μg DNA per dish) in serum-free MEM for 5 hours at 37° C. with a humidified 5% CO$_2$ atmosphere. This culture medium was then replaced with complete MEM containing 10% FBS and antibiotics (ΣCFTE29o-, CFNPE14o-) or with Dulbecco's modified Eagle's/Ham's F12 medium (DME/F12, 1:1) supplemented with 10% FBS and antibiotics (CFPAC-1). Cells were propagated at 37° C. after transfection, with daily replacement of medium for one week.

DNA and RNA Analysis

Genomic DNA and cytoplasmic RNA was isolated and purified from cells. Cellular DNA was PCR-amplified with either CF1B/CF6, CF7b/CF6, CF8b/CF6, CF1B/CF7C or CF1B/CF8C primers (Table 1). CF7B and CF7C are specific for the wtCFTR (N) allele, while CF8B and CF8C are specific for the ΔF508CFTR (ΔF508) allele. Primers CF1B (sense) and CF6 (antisense) are non-allele-specific and outside the 5' and 3' ends of the homologous region, respectively. In addition, CF6 is outside the region defined by the Eco RI/Hind III 860-bp fragment generated from the T6/20 plasmid. This insures that any fragments generated by amplification with CF6 will not detect residual 860-bp DNA carried through from the amplification of the 491-bp fragment. Conditions for PCR amplification with CF1B/CF6 were as follows: 768/771-bp fragments, respectively; primers, 0.4 μM; DNA, 50–100 ng; denaturation, 95° C. for 60 s; annealing, 56° C. for 45 s; extension, 72° C. for 90 s for 30 cycles; and Mg$^{+2}$ 1.5 mM. Direct allele-specific amplification of genomic DNA with CF7B/CF6 and CF8B/CF6 were as follows: 414- and 411-bp fragments, respectively; primers, 0.5 μM; DNA, 50–100 ng; denaturation, 95° C. for 60s, annealing 56° C. for 60 s, 72° C. for 120 s; 35 cycles with an 8 min extension on the last cycle; and Mg$^{+2}$ 2 mM. Amplification conditions with CF1B/CF7C and CF1B/CF8C were similar to those with CF7B/CF8B with CF6, but annealing was 59° C. for 60s and extension was for 90s. DNA fragments were separated by agarose electrophoresis and visualized by ethidium bromide staining.

Homologous DNA replacement was also analyzed by allele-specific Southern hybridization of the CF1B/CF6 fragment with the oligo N or oligo ΔF probes (Table 1). Hybridization was performed as described in Example 10. DNA fragments were separated by agarose gel electrophoresis. DNA was denatured with 0.4 N NaOH and 0.6 M NaCl for 30 mins., then washed once with 1.5 M NaCl and 0.5 M Tris-HCl for 30 mins. DNA was transferred to Gene Screen Plus membrane (NEN-DU Pont) by capillary blot and again denatured with 0.4 N NaOH for 1 min., then neutralized with 0.2 M Tris-HCl (pH 7.0). DNA on membranes was prehybridized for 1 hour at 37° C. in 6×SSC, 5×Denhardt's solution, and 1% SDS containing 100 μg/ml of denatured salmon sperm DNA (Sigma). Oligonucleotide probes (oligo N or oligo ΔF; 10 ng) were $^{32}$P-labeled with 20 units of T4 kinase and 40 μCi $^{32}$P-γ-ATP for 30 mins. at 37° C. Unincorporated nucleotides were removed by centrifugation of the reaction mix through a minispin column (Worthington Biochemical Corp., Freehold, N.J.). Hybridization was performed overnight at 42° C. Membranes were washed twice for 5 minutes each time in 2×SSC at room temperature; twice for 30 min. in 2×SSC, 0.1% SDS at 45° C; and once in 0.1×SSC for 30 mins. at room temperature. After washing, membranes were analyzed autoradiographically by exposure to X-ray film.

Densitometric analysis autoradiographs was carried out with a GS 300 Scanning Densitometer (Hoefer Scientific Instruments, San Francisco, Calif.) to determine the efficiency of homologous replacement. The relative efficiency of hybridization of the oligo N and oligo ΔF probes was determined by comparing the intensity of transmission after hybridization to PCR fragments derived from heterozygote (ΔF/N) lymphocyte controls. Band intensities were normalized such that signals from oligo N and oligo ΔF from the ΔF/N control were equal. DNA from transfected CF cells, amplified with primers CF1B/CF6, should give a hybridization signal for oligo N if wtCFTR sequences are present. The relative frequency of the wtCFTR in the population of 771/768-bp fragments was determined as (DN-DB)/(DN-DB)+DΔF, where DN=the densitometric value for the oligo N hybridization all samples were adjusted to the same ΔF508 hybridization values, DB=the densitometric value for the background hybridization by the oligo N probe, and D$_{ΔF}$=the normalized densitometric value for the oligo ΔF hybridization.

Cytoplasmic RNA was isolated as described in PNAS USA, 89:5171 (1992). RNA was denatured at 95° C. for 2 min., then reverse-transcribed using the reverse transcriptase provided in a PCR RNA Gene Amp kit according to manufacturer's instructions (Perkin-Elmer/Cetus). First-strand cDNA was amplified by using primer CF17 at the 5' end of exon 9 and the allele-specific oligo N or oligo ΔF and CF7C(N) or CF8C(ΔF) primers (Table 1). The respective lengths of the PCR fragments are 322-bp (CF17/oligo N) and 321-bp (CF17/oligo ΔF) or 330-bp (CF17/CF7C) and 327-bp (CF17/CF8C). The conditions for PCR amplifications are CF17/oligo N/ΔF, 322/321-bp fragment; primers, 1 μM; denaturation, 94° C. for 1 min.; annealing, 51° C. for 30 s; extension, 72° C. for 20 s with a 4-s/cycle increase in extension time for 40 cycles; and Mg$^{+2}$, 0.8 mM. The conditions for PCR are: CF17/CF7C-8C; primers, 1 μM; denaturation, 94° C. for 30 s; annealing, 57° C. for 30 s; extension, 72° C. for 30 s for 35 cycles with a with a 5 min extention on the last cycle; and Mg$^{+2}$, 2.0 mM. PCR products from the CF17/CF7C or CF8C were then digested with XhoI. DNA Fragments were visualized after electrophoresis on ethidium bromide-stained 1% agarose gels.

Patch Clamp Analysis

Cells were seeded on coated 35 mm dishes and used for patch clam experiments within 1–4 days after plating. The dishes were mounted on the stage on an inverted microscope (Zeiss, FGR). The bath perfusion rate was approximately 20 ml/min corresponding to a bath exchange rate of twice per second. The standard bath solution contained (in mM): NaCl, 145; $K_2HPO_4$, 1.6; $KH_2PO_4$, 0.4; $CaCl_2$, 1.3; $MgCl_2$, 1; D-glucose, 5. A flowing KCl electrode served as a reference and appropriate corrections for liquid-junction voltages were made. The whole cell (wc) patch clamp method used has been described previously in Ann. Rev. Physiol., 46:455 (1984). The patch pipettes were filled with a solution containing (in mM): CsCl, 125; $Na_2HPO_4$, 1.6; $NaH_2PO_{44}$, 0.4; EGTA, 1; $CaCl_2$, 0.5; $MgCl_2$, 1; D-glucose, 5; ATP, 1. The pH was adjusted to 7.2 and the $Ca^{+2}$ activity in this solution was $\sim 10^7$ M. The data were recorded using a LM EPC-7 patch clamp amplifier (List, Darmstadt, FRG) and continuously displayed by a pen recorder. The access conductance was controlled in each experiment and was in the range of 40–130 nS. The membrane voltage of the cells were recorded continuously using the current clamp mode of the patch clam amplifier and the wc-current was measured in regular intervals by clamping the membrane potential to ±30 mV in steps of 10 mV. The wc-conductance (GCl) was calculated from the measured wc-current (I) and the applied clamp voltage ($V_c$). All experiments were carried out at 37° C. Cl conductance was stimulated either with forskolin (10 $\mu$M), ionomycin ($5 \times 10^{-7}$ M), or by reducing the batch NaCl concentration to 72.5 mM (hypotonic swelling). Experiments with an access-conductance of <40 NS were eliminated from the statistics. Only experiments in which activation of the whole cell current was reversible were used for statistical analysis.

EXAMPLE 19

Gene Therapy for Cystic Fibrosis—Clinical Protocol

This example describes clinical protocol used for in vivo small fragment homologous recombination. Small fragments were prepared as described in Example 17 and encapsulated in liposomes as described in Example 15. Liposomes were administered onto cystic fibrosis patients airway epithelium.

A. Patient Evaluation

Prior to and during the gene transfer protocol, a series of tests are undertaken in order to establish baseline information relevant to the patient's clinical status (severity of CF and non-CF related illnesses) and the magnitude of the transport abnormalities within the nasal epithelium of study participants.

B. Clinical Protocol Pre-treatment Evaluation

Patients enter the study and pre-treatment evaluation is performed 4 weeks prior to gene transfer and at the time of admission. Pre-treatment evaluation involves complete history; physical examination; serum chemistry evaluation; urinalysis; and CF genotype analysis; nasal endoscopy; serum for analysis of antibody to liposomes; pulmonary function tests, including diffusion capacity; arterial blood gases and oximetry; 12-lead EKG, nasal/sinus x-rays; sputum culture and antibiotic sensitivity; and measurement of nasal potential difference.

Gene Transfer Procedures

The patient is placed in a right lateral decubitus position and given mild sedation. Nasal endoscopy is used to define a 3–5 mm region along the inferior surface of the right inferior turbinate suitable for liposomes administration. This area is rinsed with normal saline prior to gene administration. Under direct visualization, a 1 ml volume of liposome suspension formulation is administered using a syringe pump, over 20–30 minute period.

Homologous Replacement Evaluation

Patients are monitored in the hospital for vital signs every 30 minutes for the first two hours following gene administration, then on an hourly basis for the next six hours, every two hours for the next 16–24 hours and finally every 6 hours for the duration of the admission of the hospital. During hospitalization all standard cystic fibrosis therapies continue.

Confirmation of gene correction is by the method of the invention, particularly by its new assay for determination of frequency of homologous replacement.

What is claimed is:

1. A method for in vitro homologous replacement, in target cells, of an exon carrying an endogenous targeted mutant DNA sequence of a gene for Fanconi's anemia, thalassaemias, cystic fibrosis, sickle cell anemia, retinitis pigmentosa, xeroderma pigmentosum, ataxia telangiectasia, Bloom's syndrome, retinoblastoma, Duchenne's muscular dystrophy, or Tay-Sachs disease, with an exogenous replacement DNA fragment comprising 3' and 5' flanking intronic sequences homologous to 3' and 5' flanking sequences of the mutant DNA sequence, said intronic sequences adjacent to an exon carrying a silent mutation that gives rise to a novel restriction enzyme cleavage site not present in the exon carrying the targeted mutant DNA sequence, and the sequence to replace the targeted mutant DNA sequence, said method comprising steps:

(a) identifying the exon containing the targeted mutant DNA sequence to be replaced and 3' and 5' flanking intronic sequences adjacent to said exon;

(b) generating the exogenous replacement DNA fragment comprising homologous 3' and 5' flanking intronic sequences adjacent to the exon having the sequence to replace the targeted mutant DNA sequence and carrying a silent mutation that gives rise to a novel restriction enzyme cleavage site not present in the exon carrying the targeted mutant DNA sequence;
wherein total size of the replacement DNA fragment is from 1 to 2000 bases;
wherein the replacement DNA fragment is a single stranded DNA generated from a double stranded fragment by denaturation or by separation of a biotin labeled complementary strand from a strand comprising the replacement fragment;
wherein the double stranded fragment is comprised of two complementary DNA strands each of which is able to replace one strand of the targeted genomic DNA;

(c) transfecting or delivering the exogenous replacement DNA fragment of step (b) into the target cells containing the targeted mutant DNA sequence, wherein the transfection or the fragment delivery is accomplished by incubating the replacement DNA fragment of step (b) in a transfection cocktail, forming a transfection mix, introducing the incubated transfection mix to the cells of step (c) grown to 70–90% confluence, and incubating the transfection mix in the presence of the cells at about 32 to 40° C. temperature;

(d) propagating the incubated cells in a fresh growth medium for about two days to about two weeks; and (f) determining the extent of homologous replacement by PCR identification of cells within the total cell population which have replaced the endogenous targeted mutant DNA with the exogenous replacement DNA fragment at a target genomic locus.

2. The method of claim 1 wherein said replacement DNA fragment is identified using primers of about 25 bases that are outside of regions of homology defined by the exogenous replacement DNA fragment, or primers that are allele-specific and differentiate between the endogenous targeted mutant sequence and the exogenous replacement DNA fragment, or by Southern hybridization with allele-specific oligonucleotide probes that differentiate between the endogenous targeted mutant sequence and the exogenous replacement DNA fragment.

3. The method of claim 2 wherein said replacement DNA fragment is generated by PCR amplification, oligonucleotide synthesis, plasmid cleavage with restriction endonuclease or by a combination of restriction enzyme cleavage of plasmid inserts and ligation of contiguous insert fragments.

4. The method of claim 3 wherein said replacement DNA fragment is uncoated or coated with a recombinase or complexed with a protein, provided that the recombinase is not recA.

5. The method of claim 4 wherein the exogenous replacement DNA fragment of step (b) is delivered into the target cell by electroporation, microinjection, complexed onto a lipid layer, in a dendrimer or conjugated to polylysine.

6. The method of claim 5 wherein the targeted mutant DNA sequence to be replaced is a DNA sequence present in the cystic fibrosis gene and wherein the primers are selected from the group consisting of primers CF1, CF1B, CF5, CF6, CF7B, CF8B, CF7C, CF8C, CF9, CF14, CF17 and CF22.

7. The method of claim 5 wherein the targeted mutant DNA sequence to be replaced is a DNA sequence present in the sickle cell anemia gene wherein said sequence is replaced with a replacement genomic DNA sequence encoding β-globin, said genomic DNA further containing non-coding sequences flanking the replacement sequence, and wherein the primers are selected from the group consisting of primers SC1(+), SC2(−), SC3(+), SC4(−), SC5(+), SC6(−), SC-BA(−) and SC-BS(−).

8. The method of claim 5 wherein the targeted mutant DNA sequence to be replaced is a DNA sequence present in the gene causing thalassaemias, wherein said sequence is replaced with a replacement genomic DNA sequence in the thalassaemias causing genomic loci, said replacement DNA sequence further containing non-coding sequences flanking the replacement sequence.

9. The method of claim 5 wherein the targeted mutant DNA sequence to be replaced is a DNA sequence present in a gene causing xeroderma pigmentosum, wherein said sequence is replaced with a replacement genomic DNA that contains non-coding sequences flanking the replacement sequence.

10. An immortalized human cell line carrying two alleles of a defective cellular cystic fibrosis DNA, wherein said cell line is identified as ΣCFTE290- and deposited under the ATCC Accession No. CRL 11151.

11. A method for in vitro homologous replacement, in target cells of a subject suffering from a genetic disease caused by a mutated DNA sequence, of an exon carrying a targeted mutant DNA sequence of a gene for Fanconi's anemia, cystic fibrosis, thalassaemias, sickle cell anemia, retinitis pigmentosa, xeroderma pigmentosum, ataxia telangiectasia, Bloom's syndrome, retinoblastoma, Duchenne's muscular dystrophy, or Tay-Sachs disease, with an exogenous replacement DNA fragment comprising 3' and 5' flanking intronic sequences homologous to 3' and 5' flanking sequences of the mutant DNA sequences, said intronic sequences adjacent to an exon carrying a silent mutation that gives rise to a novel restriction enzyme cleavage site not present in the exon carrying the targeted mutant DNA sequence, and the sequence to replace the targeted mutant DNA sequence, said method comprising steps:

(a) identifying the exon containing the targeted mutant DNA sequence to be replaced and 3' and 5' flanking intronic sequences adjacent to said exon;

(b) generating the exogenous replacement DNA fragment comprising homologous 3' and 5' flanking intronic sequences adjacent to the exon having the sequence to replace the targeted mutant DNA sequence and carrying a silent mutation that gives rise to a novel restriction enzyme cleavage site not present in the exon carrying the targeted mutant DNA sequence;

wherein total size of the replacement DNA fragment is from 1 to 2000 bases;

wherein the replacement DNA fragment is a single stranded DNA generated from a double stranded fragment by denaturation or by separation of a biotin labeled complementary strand from a strand comprising the replacement fragment;

wherein the double stranded fragment is comprised of two complementary strands each of which is able to replace one strand of the targeted genomic DNA;

(c) transfecting or delivering the exogenous replacement DNA fragment of step (b) into the target cells containing the targeted mutant DNA sequence wherein a transfection or the DNA fragment delivery is accomplished by incubating the replacement DNA fragment of step (b) in a transfection cocktail, forming a transfection mix, introducing the incubated transfection mix to the cells of step (c) grown to 70–90% confluence, and incubating the transfection mix in the presence of the cells at about 32 to 40° C. temperature; and (d) propagating the incubated cells in a fresh growth medium for about two days to about two weeks;

(e) determining the extent of homologous replacement by PCR identification of cells within the total cell population which have replaced the endogenous targeted mutant DNA with the exogenous replacement DNA fragment at a target genomic locus.

12. A method for in vitro homologous replacement, in target cells, of an endogenous targeted DNA sequence in an exon with a replacement DNA fragment carrying a silent mutation, wherein the targeted DNA sequence is replaced with mutated DNA sequence encoding a gene for Fanconi's anemia, cystic fibrosis, sickle call anemia, thalassaemias, retinitis pigmentosa, xeroderma pigmentosum, ataxia telangiectasia, Bloom's syndrome, retinoblastoma, Duchenne's muscular dystrophy, or Tay-Sachs disease, said replacement DNA fragment comprising 3' and 5' flanking intronic sequences homologous to 3' and 5' flanking sequences of the mutant DNA sequence, said intronic sequences adjacent to the DNA sequence carrying a silent mutation that gives rise to a novel restriction enzyme cleavage site not present in the exon carrying the targeted DNA sequence, and the mutated DNA sequence to replace the targeted DNA sequence, said method comprising steps:

(a) identifying the exon containing the targeted DNA sequence to be replaced and 3' and 5' flanking intronic sequences adjacent to said exon;

(b) generating the exogenous replacement DNA fragment comprising homologous 3' and 5' flanking intronic sequences adjacent to the exon having the mutated DNA sequence to replace the targeted DNA sequence carrying the mutation that gives rise to a novel restriction enzyme cleavage site not present in the exon carrying the targeted DNA sequence;

wherein total size of the replacement DNA fragment is from 1 to 2000 bases;

wherein the replacement DNA fragment is a single stranded DNA generated from a double stranded fragment by denaturation or by separation of a biotin labeled complementary strand from a strand comprising the replacement fragment;

wherein the double stranded fragment is comprised of two complementary DNA strands each of which is able to replace one strand of the targeted genomic DNA;

(c) transfecting or delivering the exogenous replacement DNA fragment of step (b) into the target cells containing the targeted DNA sequence wherein the transfection or the DNA fragment delivery is accomplished by incubating the replacement mutant DNA fragment of step (b) in a transfection cocktail, forming a transfection mix, introducing the incubated transfection mix to the cells of step (c) grown to 70–90% confluence, and incubating the transfection mix in the presence of the cells at about 32 to 40° C. temperature;

(d) propagating the incubated cells in a fresh growth medium for about two days to about two weeks; and (e) determining the extent of homologous replacement by PCR identification of cells within the total cell population which have replaced the endogenous targeted DNA with the exogenous replacement mutant DNA fragment at a target genomic locus.

13. An immortalized mammalian cell line comprising the replacement DNA fragment of claim 12 wherein said replacement fragment is a mutant DNA sequence causing a genetic disease.

* * * * *

SEQUENCE LISTING

<160> NUMBER OF SEQ ID NOS: 87

<210> SEQ ID NO 1
<211> LENGTH: 2908
<212> TYPE: DNA
<213> ORGANISM: human

<400> SEQUENCE: 1

```
gaattccagc cagacgtgat ggcgggtgcc cgtagtccca gctactcggg aggctgaggc      60
aggagaatgg cgtgaaccca ggaggcagaa cttgcagtga gccgagatcg cgccactgca     120
ctctagcctg ggtgacagag tgagactctg tctctaaata aataaataaa taaataaata     180
aataaataaa atcagtgctt tttcttcctc tgctacctcc tttccttcta ctcagtttta     240
gtcagtagta ttatcttttt tcagatttat ctttgtattg ttaaatctgc ttatgcttct     300
attactttat ttattagctt taaatgatac cttttgactt tcagcttttc ttaataaagc     360
aatcagcaaa tttcctttac actccacact tataccccat ttcctttgtt tgtttatttg     420
```

```
gtttttactt ctaactttc ttattgtcag gacatataac atatttaaac tttgttttc        480 aactcgaatt ctgccattag tttaatttt tgttcacagt tatataaatc tttgttcact       540
gatagtcctt ttgtactatc atctcttaaa tgactttata ctccaagaaa ggctcatggg      600
aacaatatta cctgaatatg tctctattac ttaatctgta cctaataata tgaaggtaat     660
ctactttgta ggatttctgt gaagattaaa taaattaata tagttaaagc acatagaaca     720
gcactcgaca cagagtgagc acttggcaac tgttagctgt tactaacctt tcccattctt    780
cctccaaacc tattccaact atctgaatca tgtgcccctt ctctgtgaac ctctatcata    840
atacttgtca cactgtattg taattgtctc ttttactttc ccttgtatct tttgtgcata    900
gcagagtacc tgaaacagga agtattttaa atattttgaa tcaaatgagt taatagaatc    960
tttacaaata agaatataca cttctgctta ggatgataat tggaggcaag tgaatcctga   1020
gcgtgatttg ataatgacct aataatgatg gttttatt ccagacttca cttctaatga    1080
tgattatggg agaactggag ccttcagagg gtaaaattaa gcacagtgga agaatttcat   1140
tctgttctca gttttcctgg attatgcctg gcaccattaa agaaaatatc atctttggtg   1200
tttcctatga tgaatataga tacagaagcg tcatcaaagc atgccaacta gaagaggtaa   1260
gaaactatgt gaaaactttt tgattatgca tatgaaccct tcacactacc caaattatat   1320
atttggctcc atattcaatc ggttagtcta catatattta tgtttcctct atgggtaagc   1380
tactgtgaat ggatcaatta ataaaacaca tgacctatgc tttaagaagc ttgcaaacac   1440
atgaaataaa tgcaatttat ttttaaata atgggttcat ttgatcacaa taaatgcatt   1500
ttatgaaatg gtgagaattt tgttcactca ttagtgagac aaacgtcctc aatggttatt   1560
tatatggcat gcatataagt gatatgtggt atctttttaa aagataccac aaaatatgca   1620
tcttaaaaaa tatactccaa aaattattaa gattattta ataattaa taatactata   1680 gcctaatgga atgagcattg atctgccagc agagaattag aggggtaaaa ttgtgaagat   1740
attgtatccc tggctttgaa caaataccat ataacttcta gtgactgcaa ttctttgatg   1800
cagaggcaaa atgaagatga tgtcattact catttcacaa caatattgga gaatgagcta   1860
attatctgaa aattacatga agtattccaa gagaaaccag tatatggatc ttgtgctgtt   1920
cactatgtaa attgtgtgat ggtggggttca gtagttattg ctgtaaatgt tagggcaggg   1980
caatatgtta ctatgaagtt tattgacagt atactccaaa tagtgtttgt gattcaaaag   2040
caatatcttt gatagttggc atttgcaatt cctttatata atctttatg aaaaaaattg   2100 cagagaaagt aaaatgtagc ttaaaataca gtatccaaaa aaatggaaaa gggcaaaccg   2160
tggattagat agaaatggca attcttataa aaagggttgc atgcttacat gaatggcttt   2220
ccatgtatat actcagccat tcaacagttt tttttttaga gccccatcct tattttttat    2280
acactttgag agcataatga aagaaaagc tacctgcaaa agtttggac ttacctcaaa     2340 gaggatatac tacattcctc aaaaggcctt cttccaggaa tagtatttca taacctggag   2400
gttggaaaaa tctggattag ttacaaaaaa atctgagtgt ttctagcgga cacagatatt   2460
tgtctaggag gggactaggt tgtagcagtg gtagtgcctt acaagataaa tcatgggctt   2520
tatttactta cgagtggaaa agttgcggaa ggtgccttac agactttttt tttgcgttaa   2580
gtatgtgttt tccatagga attaatttat aaatggtggt tgatttcct caagtcaacc    2640 tttaaaagta tatttagcca aaatatagct taaatatatt actagtaata aatttagtac   2700
tgtgggtctc tcattctcga aatgagcatt tactaatttc tgaacactgt gctaggtcct   2760
gggaatacca aattgaataa gacatagtct attttctga agggtttata gcagagtccc   2820
```
ctgtgttaat aatgaaggag tgtgtggtat gtgaatcata tatcaatagg gttgttaaaa  2880
ataatgaaaa aaggagaaga gggaattc                                      2908

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
gcagagtacc tgaaacagga                                               20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
ccttctctgt gaacctctat ca                                            22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
cattcacagt agcttaccca                                               20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 5
ccacatatca ctatatgcat gc                                            22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 6
ccattaaaga aaatatcatt gg                                            22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 7

```
ccattaaaga aaatatcatt gg                                          22
```

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
ataggaaaca ccaaagatga                                             20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
ataggaaaca ccaatgatat                                             20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 10
actttaaagc tgtcaagccg tg                                          22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 11
ctgtattttg tttattgctc caa                                         23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 12
gagggatttg gggaattatt tg                                          22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 13
cttgctaaag aaattcttgc tc                                          22
```

```
<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 14
caccaaagat gatattttc                                                    19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 15
aacaccaatg atattttctt                                                   20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 16
cttttcctgg attatgcctg gcac                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 17
actgtagctg tactaccttc catc                                              24

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 18
gacaattaca atacagtgtg acaag                                             25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 19
gggttcattt gatcacaata aatgc                                             25

<210> SEQ ID NO 20
```

<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 20
cagcttttct taataaagca atcag                                         25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
tgcaattctt tgatgcagag gcaa                                          24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
agaatgagag acccacagta ctaaa                                         25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 23
attcaggtaa tattgttccc atgag                                         25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 24
tattgacagt atactccaaa tagtg                                         25

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 25
taacctttcc cattcttcct cca                                           23

<210> SEQ ID NO 26
<211> LENGTH: 25
<212> TYPE: DNA

```
<213> ORGANISM: Artificial Sequence
<220> FEATURE:
<223> OTHER INFORMATION: Description of Artificial Sequence: synthetic
      oligonucleotide

<400> SEQUENCE: 26
tctactttgt aggatttctg tgaag                                              25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 27
attctctgct ggcagatcaa tgc                                                23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 28
gttttcctgg attatgcctg gcac                                               24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 29
gttggcatgc tttgatgacg cttc                                               24

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 30
gttttcccag tcacgac                                                       17

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 31
caggaaacag ctatgac                                                       17

<210> SEQ ID NO 32
<211> LENGTH: 23
<212> TYPE: DNA
<213> ORGANISM: Artificial Sequence
<220> FEATURE:
```

<223> OTHER INFORMATION: Description of Artificial Sequence: synthetic
      oligonucleotide

<400> SEQUENCE: 32
tagcaatttg tactgatggt atg                                              23

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 33
tatacacaat ttaaggcatt ag                                               22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 34
ccctgtggag ccacaccta gggt                                              24

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 35
aacgatcctg agacttccac act                                              23

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 36
acatttgctt ctgacacaac tgtg                                             24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 37
agggttgccc ataacagcat cag                                              23

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 38
cttctcctca ggagt                                           15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 39
cttctccaca ggagt                                           15

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 40
agcatttttc aggttcctcc ag                                   22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 41
aacctactta acctggcttc ct                                   22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 42
ggcttgtttt gaagttacag gc                                   22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 43
aagccatcag caaccacaag a                                    21

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 44
cctcatcact aatcacactt tg                                             22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 45
tcctcatcac taatcacact tg                                             22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 46
gaagtttcat tgaagtgcaa ag                                             22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 47
ggaagtttca ttgaagtgca ag                                             22

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 48
gcctagaaaa gtccctgtat catg                                           24

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 49
gacacaagta gctaacacaa tcagc                                          25

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 50
cccttttcaa ggtgagtagt caag                                           24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 51
cactcatgta gttagagcat aggg                                        24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 52
gtactcatca taggaaacac cgat                                        24

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 53
actcatcata ggaaacacca aa                                          22

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 54
gaattcatac agacttttgg tttgt                                       25

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 55
ctgtctgctt cctgactatg gata                                        24

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 56
ggggtccttg acatgtttac at                                          22

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 57
gggaattact gcagaaagca caac                                   24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 58
taaagaaatc cttgcacgct gacc                                   24

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 59 aacaagatg gattgcacgc ag                                      22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 60
cgccaagctc ttcagcaata tc                                     22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 61
attcggctat gactgggcac aa                                     22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 62
gccacagtcg atgaatccag aa                                     22

<210> SEQ ID NO 63
<211> LENGTH: 20

<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 63
tttctgtcag tggagagggt                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 64
tggttgtctg gtaaaaggac                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 65
gggtaaagga gaagaacttt                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 66
atgccatgtg taatcccagc                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 67
cggcacgctg attgaagcag                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 68
tggaccattt cggcacagcc                                              20

<210> SEQ ID NO 69
<211> LENGTH: 21
<212> TYPE: DNA
<213> ORGANISM: Artificial Sequence -continued

```
<220> FEATURE:
<223> OTHER INFORMATION: Description of Artificial Sequence: synthetic
      oligonucleotide

<400> SEQUENCE: 69
tcgcgtcaca ctacgtctga a                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 70
cgcctgccag tatttagcga a                                              21

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 71
ccgctggata acgacattgg                                                20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 72
gttgctgttg actgtagcgg                                                20

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 73
tctgaccacc agcgaaatgg a                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 74
ccgtcgatat tcagccatgt g                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: synthetic
``` oligonucleotide

<400> SEQUENCE: 75
gaaaatggtc tgctgctgct g                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 76
cgggcaaata atatcggtgg c                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 77
tgttgcagtg cacggcagat a                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 78
gatgttgaac tggaagtcgc c                                              21

<210> SEQ ID NO 79
<211> LENGTH: 3
<212> TYPE: PRT
<213> ORGANISM: Unknown
<220> FEATURE:
<223> OTHER INFORMATION: Description of Unknown Organism: ligand

<400> SEQUENCE: 79

Met Leu Phe
  1

<210> SEQ ID NO 80
<211> LENGTH: 3
<212> TYPE: PRT
<213> ORGANISM: Unknown
<220> FEATURE:
<223> OTHER INFORMATION: Description of Unknown Organism: ligand

<400> SEQUENCE: 80

Arg Asp Gly
  1

<210> SEQ ID NO 81
<211> LENGTH: 8
<212> TYPE: PRT
<213> ORGANISM: Unknown
<220> FEATURE:
<223> OTHER INFORMATION: Description of Unknown Organism: ligand

<400> SEQUENCE: 81

Cys Ser Gly Arg Glu Asp Val Trp
 1               5

<210> SEQ ID NO 82
<211> LENGTH: 7
<212> TYPE: PRT
<213> ORGANISM: Unknown
<220> FEATURE:
<223> OTHER INFORMATION: Description of Unknown Organism: ligand

<400> SEQUENCE: 82

Pro Lys Lys Lys Arg Lys Val
 1               5

<210> SEQ ID NO 83
<211> LENGTH: 10
<212> TYPE: PRT
<213> ORGANISM: Unknown
<220> FEATURE:
<223> OTHER INFORMATION: Description of Unknown Organism: ligand

<400> SEQUENCE: 83

Ala Ala Phe Glu Asp Leu Arg Val Leu Ser
 1               5                  10

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 84
gattatggga gaactcgagc c                                    21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 85
accctctgaa ggctcgagtt c                                    21

<210> SEQ ID NO 86
<211> LENGTH: 14
<212> TYPE: DNA
<213> ORGANISM: Unknown
<220> FEATURE:
<223> OTHER INFORMATION: Description of Unknown Organism: PCR product

<400> SEQUENCE: 86
catcggtgtt tcct                                            14

<210> SEQ ID NO 87
<211> LENGTH: 14
<212> TYPE: DNA
<213> ORGANISM: Unknown
<220> FEATURE:
<223> OTHER INFORMATION: Description of Unknown Organism: PCR product

<400> SEQUENCE: 87
catctttggt gttt                                            14